United States Patent
Starr et al.

(10) Patent No.: US 7,740,591 B1
(45) Date of Patent: Jun. 22, 2010

(54) APPARATUS AND METHOD FOR MONITORING PRESSURE RELATED CHANGES IN THE EXTRA-THORACIC ARTERIAL CIRCULATORY SYSTEM

(75) Inventors: Eric W. Starr, Allison Park, PA (US); James A. Scull, Durham, NC (US); Eric Ayers, Aliquippa, PA (US); Bernie F. Hete, Kittanning, PA (US); Donald S. Wilczek, Verona, PA (US); Mark H. Sanders, Wexford, PA (US)

(73) Assignee: Ric Investments, LLC, Wilmington, DE (US)

( * ) Notice: Subject to any disclaimer, the term of this patent is extended or adjusted under 35 U.S.C. 154(b) by 1188 days.

(21) Appl. No.: 10/999,186

(22) Filed: Nov. 29, 2004

Related U.S. Application Data

(60) Provisional application No. 60/525,954, filed on Dec. 1, 2003.

(51) Int. Cl.
*A61B 5/08* (2006.01)
(52) U.S. Cl. ............................ 600/534; 600/529
(58) Field of Classification Search .......... 600/529–543
See application file for complete search history.

(56) References Cited

U.S. PATENT DOCUMENTS

| | | | | |
|---|---|---|---|---|
| 5,361,776 | A | * | 11/1994 | Samuelson et al. ........... 600/547 |
| 5,385,144 | A | * | 1/1995 | Yamanishi et al. ........... 600/330 |
| 5,396,893 | A | | 3/1995 | Oberg et al. |
| 5,511,554 | A | * | 4/1996 | Helfenbein et al. ........... 600/519 |
| 5,562,712 | A | * | 10/1996 | Steinhaus et al. ............. 607/20 |
| 6,017,315 | A | | 1/2000 | Starr et al. |
| 6,064,898 | A | | 5/2000 | Aldrich |
| 6,122,535 | A | | 9/2000 | Kaestle et al. |
| 6,129,675 | A | | 10/2000 | Jay |

(Continued)

FOREIGN PATENT DOCUMENTS

WO  WO 03/000125    1/2003

(Continued)

OTHER PUBLICATIONS

Hartert et al., "Use of Pulse Oximetry to Recognize Severity of Airflow Obstruction in Obstructive Airway Disease", Chest Journal, Feb. 1999, pp. 475-481, 115.

(Continued)

*Primary Examiner*—Patricia C Mallari
*Assistant Examiner*—Karen E Toth
(74) *Attorney, Agent, or Firm*—Michael W. Haas

(57) ABSTRACT

A method and apparatus for monitoring changes in the intra-thoracic pressure of a patient due to the patient's respiratory activity or volumetric changes in the extra-thoracic arterial circulatory system due to cardiac function based on the changes in pressure in the patient's extra-thoracic arterial circulatory system as measured by a plethysmography sensor, such as an photoplethysmograph. A frequency spectrum is generated for the plethysmograph signal and the frequencies of interest is isolated from the frequency spectrum by setting appropriate cutoff frequencies for the frequency spectrum. This isolated frequency is used to filter the plethysmograph signal to provide a signal indicative of the patient's respiratory activity or cardiac function. For corrections for breathing frequency roll-off and deviations of the I:E ratio from 1:1.

48 Claims, 45 Drawing Sheets

U.S. PATENT DOCUMENTS

| | | |
|---|---|---|
| 6,325,761 B1 | 12/2001 | Jay |
| 6,485,481 B1* | 11/2002 | Pfeiffer ..................... 604/523 |
| 6,544,192 B2 | 4/2003 | Starr et al. |
| 6,610,018 B1* | 8/2003 | McIntyre ................... 600/485 |
| 6,616,613 B1* | 9/2003 | Goodman ................... 600/504 |
| 6,650,917 B2 | 11/2003 | Diab |
| 6,650,918 B2 | 11/2003 | Terry |
| 6,669,632 B2* | 12/2003 | Nanba et al. ................ 600/300 |
| 6,709,402 B2 | 3/2004 | Dekker |
| 6,783,498 B2 | 8/2004 | Sackner |
| 6,869,402 B2 | 3/2005 | Arnold |
| 7,128,714 B1* | 10/2006 | Antonelli et al. ............ 600/485 |
| 2002/0022785 A1* | 2/2002 | Romano ..................... 600/526 |
| 2002/0029000 A1 | 3/2002 | Ohsaki et al. |
| 2002/0188205 A1* | 12/2002 | Mills .......................... 600/481 |
| 2004/0003813 A1* | 1/2004 | Banner et al. ........... 128/204.21 |
| 2004/0143191 A1* | 7/2004 | Faisandier .................. 600/485 |
| 2004/0162499 A1* | 8/2004 | Nagai et al. ................. 600/529 |
| 2005/0187481 A1* | 8/2005 | Hatib et al. ................. 600/485 |
| 2007/0032732 A1* | 2/2007 | Shelley et al. .............. 600/504 |

FOREIGN PATENT DOCUMENTS

| | | |
|---|---|---|
| WO | WO 03/001180 | 1/2003 |

OTHER PUBLICATIONS

Jay et al., "Analysis of Physician Ability in the Measurement of Pulsus Paradoxus by Sphygmomanometry", Chest Journal, Aug. 2000, pp. 348-352, 118.

Arnold et al., "Estimation of Airway Obstruction Using Oximeter Plethysmograph Waveform Data", Respiratory Research, Jun. 2005.

* cited by examiner

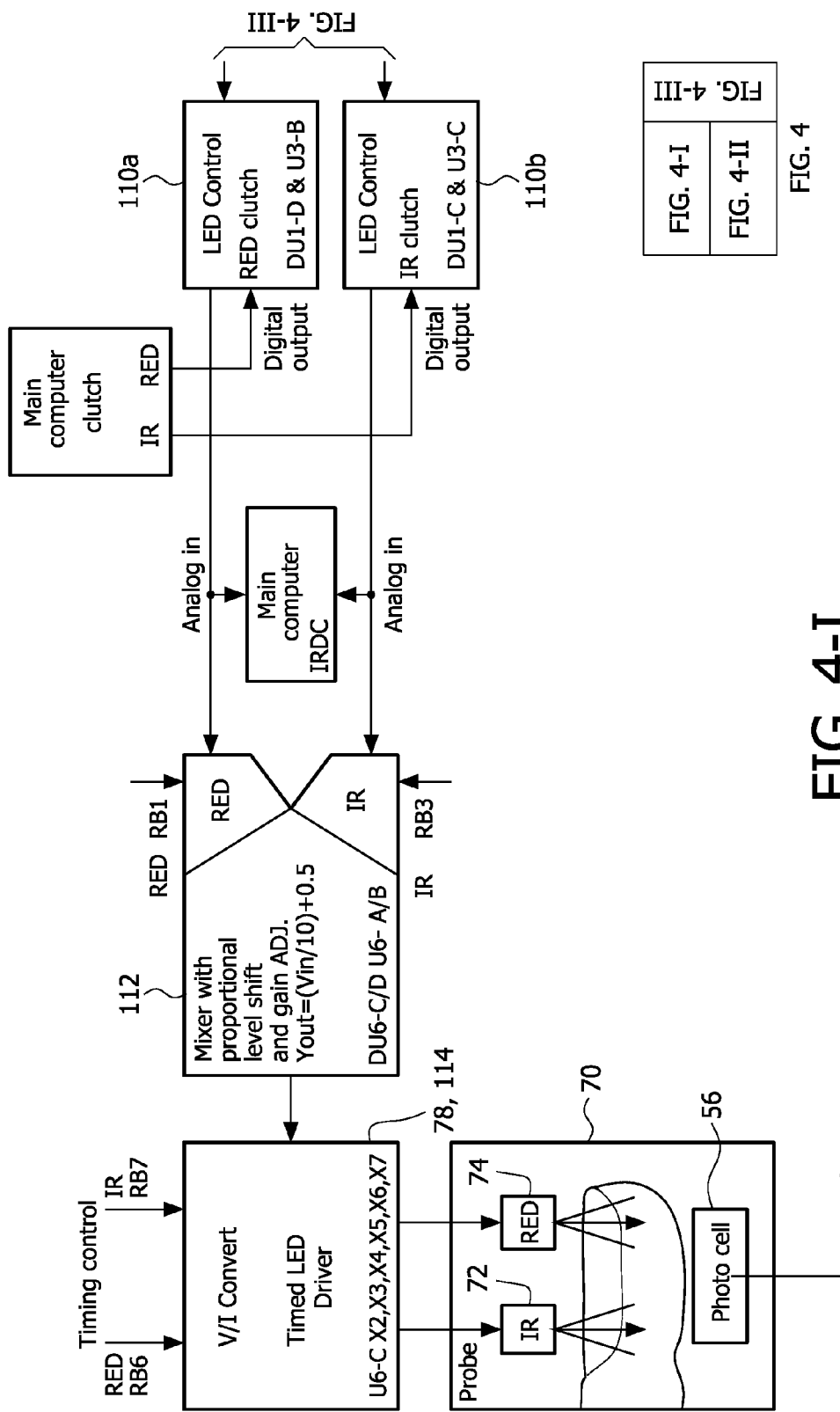
FIG. 4-I

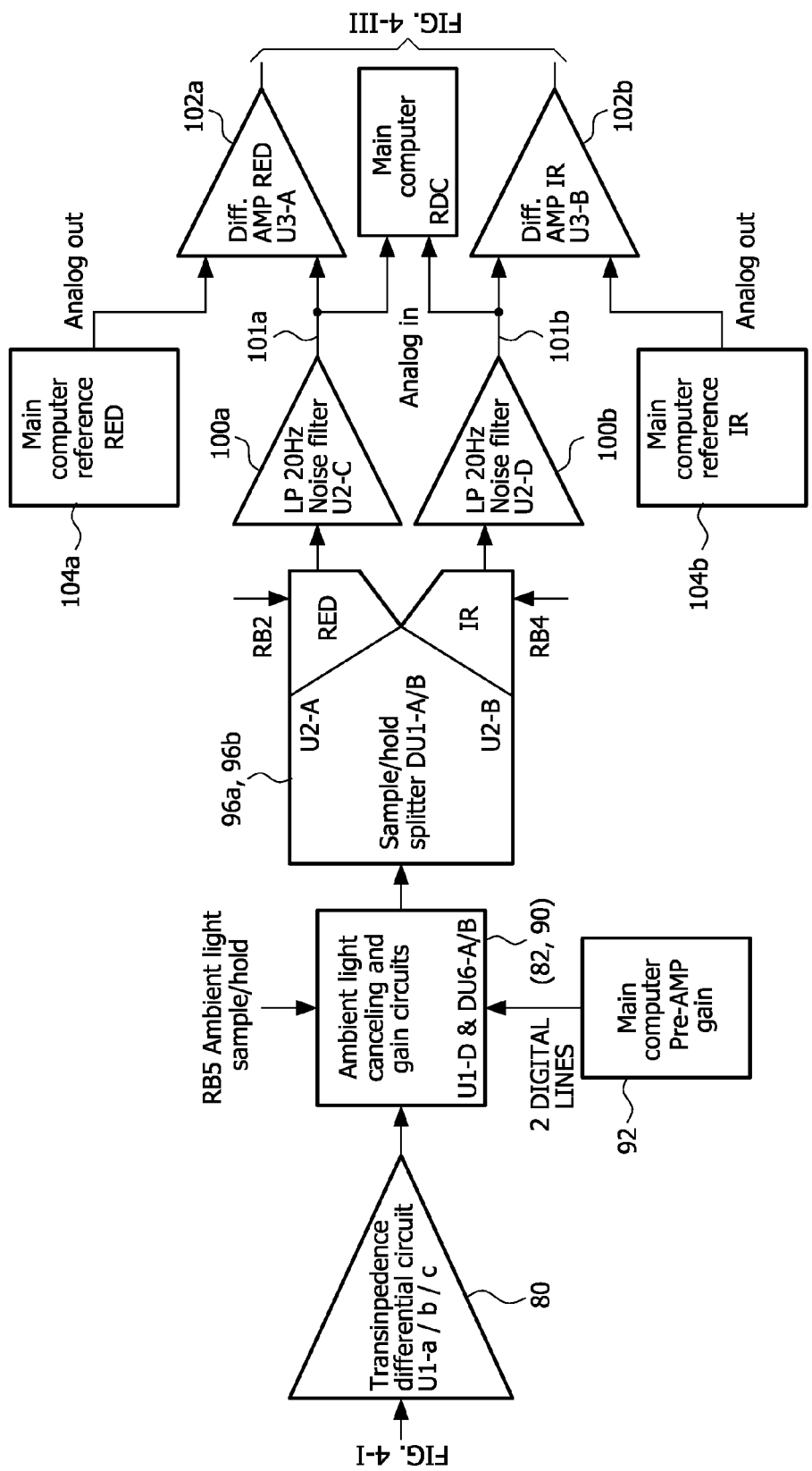
FIG. 4-II

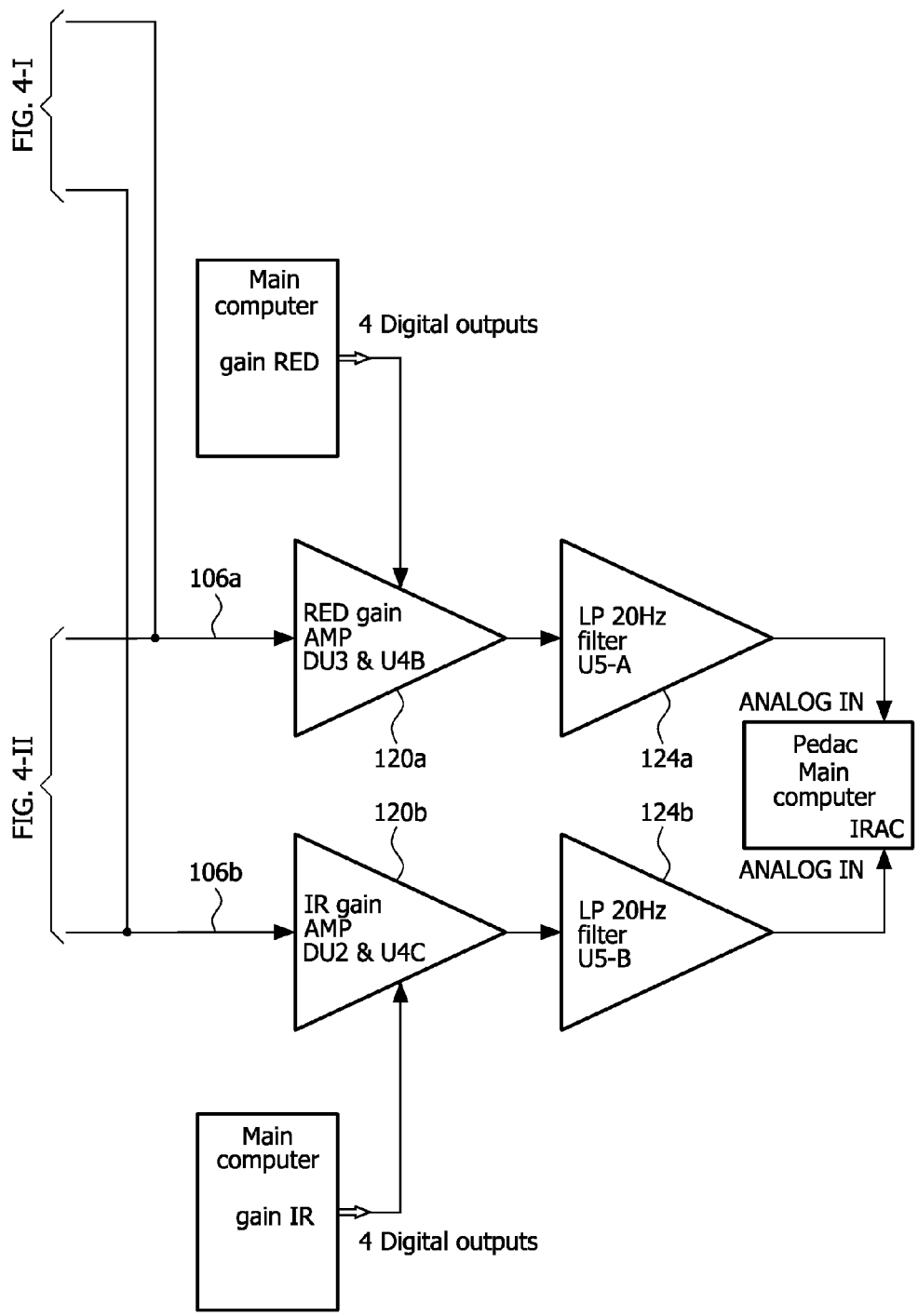
FIG. 4-III

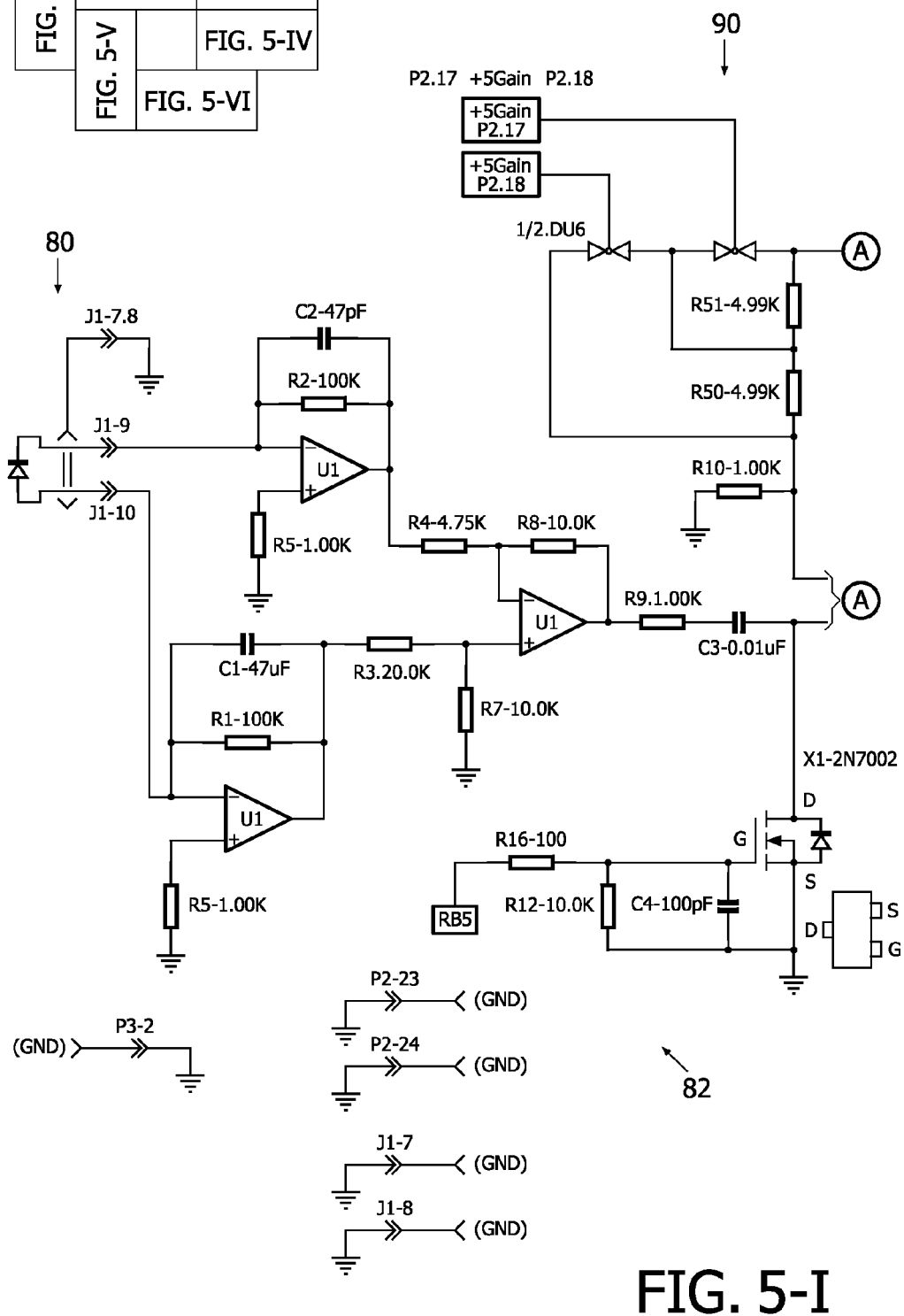
FIG. 5-I

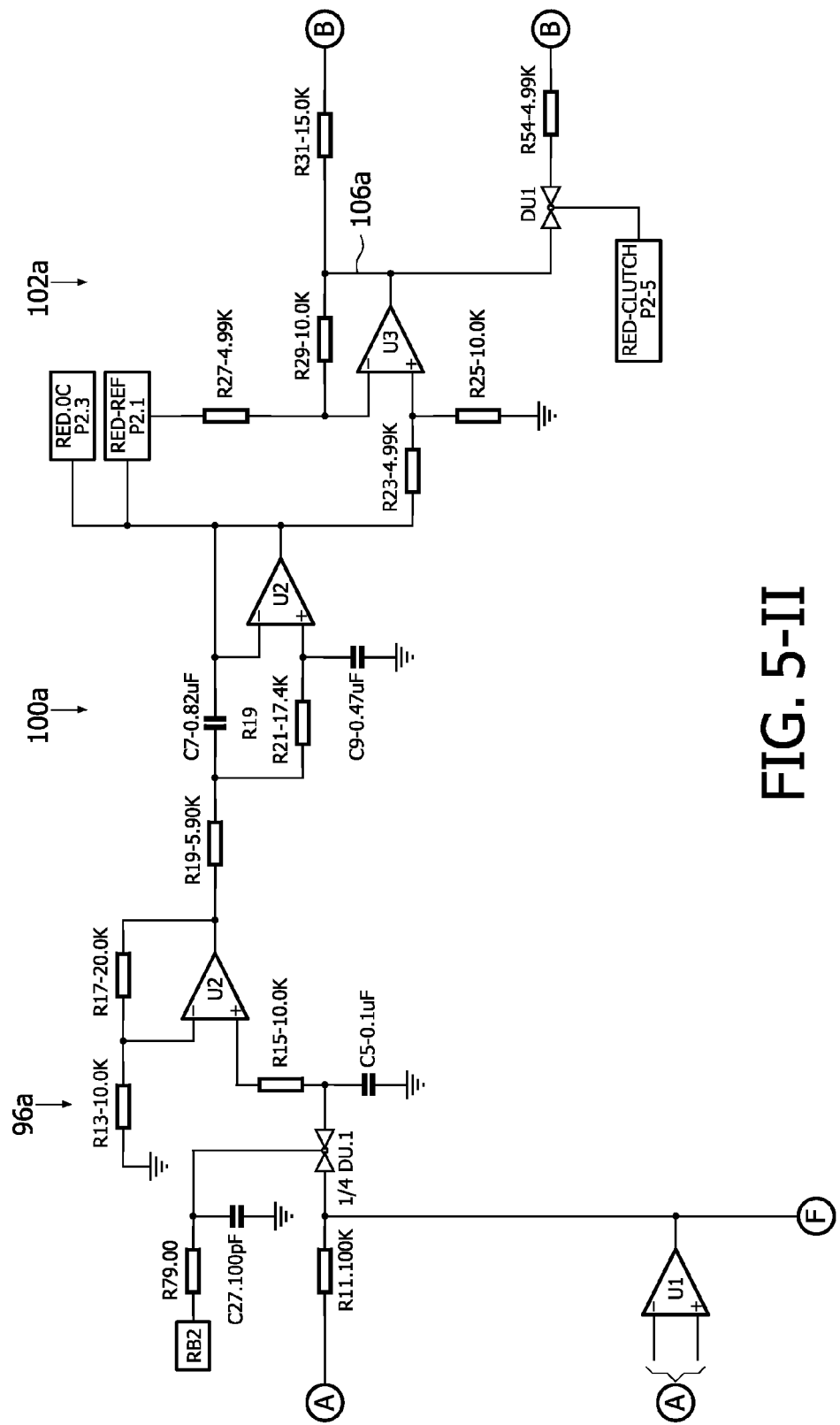
FIG. 5-II

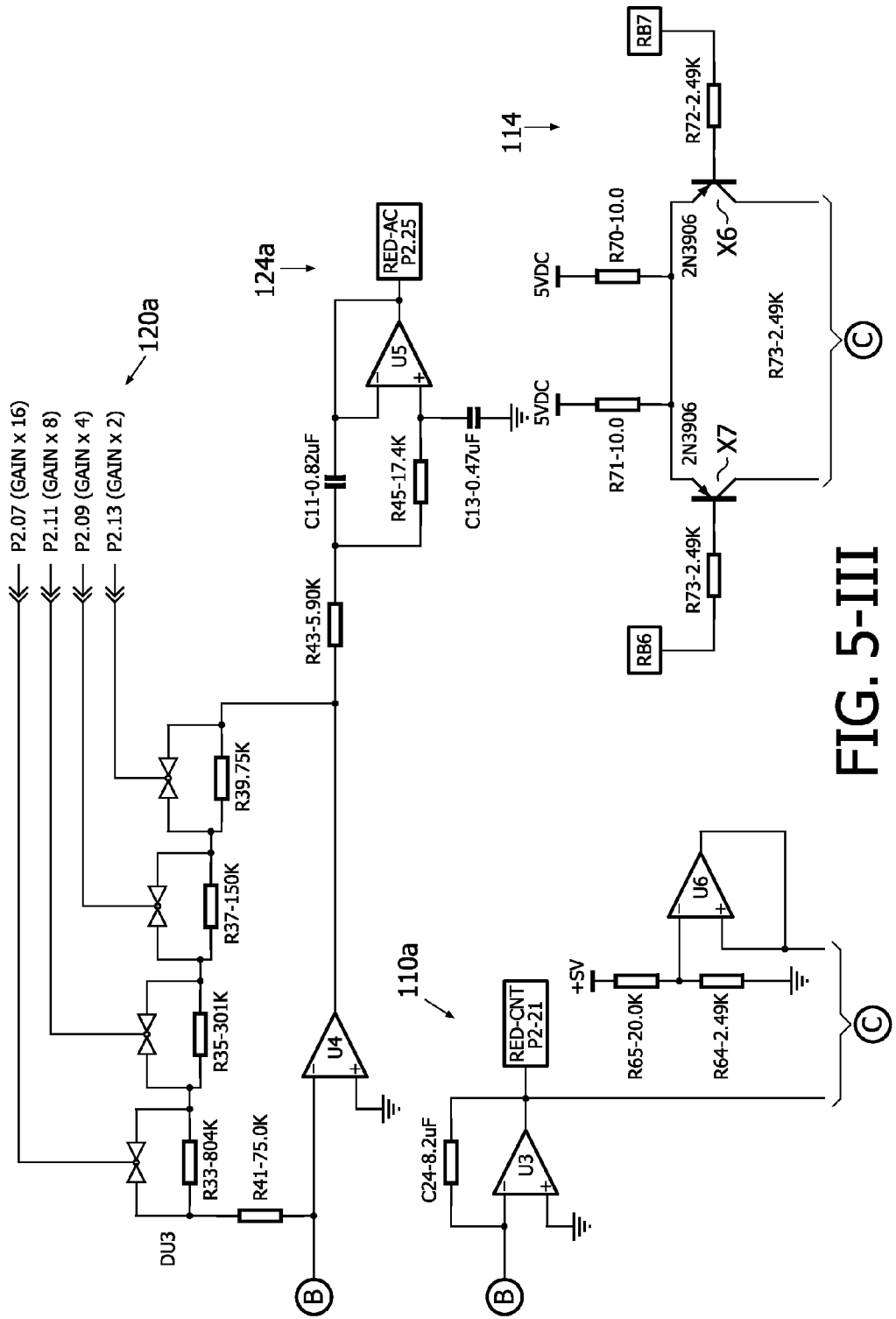
FIG. 5-III

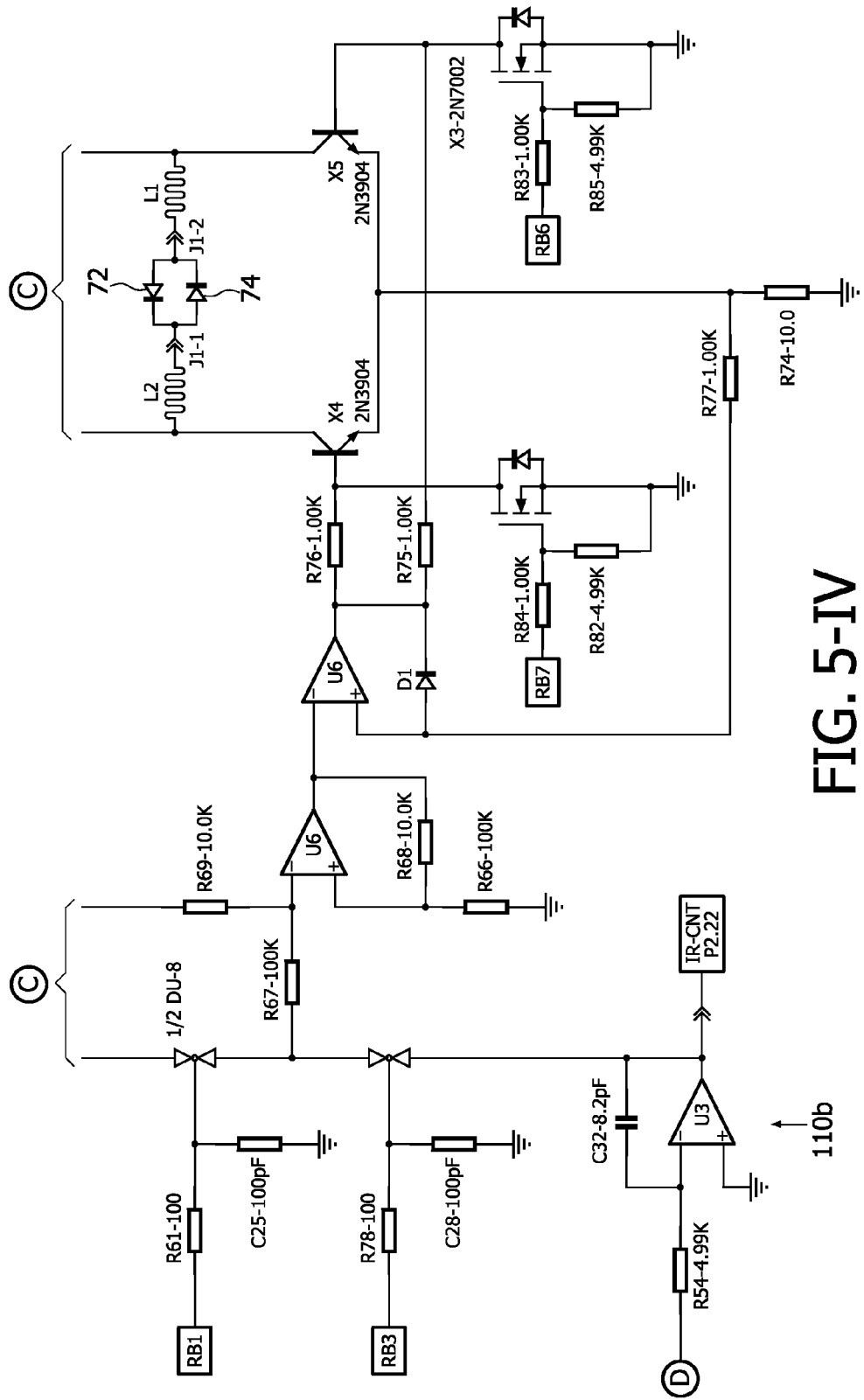
FIG. 5-IV

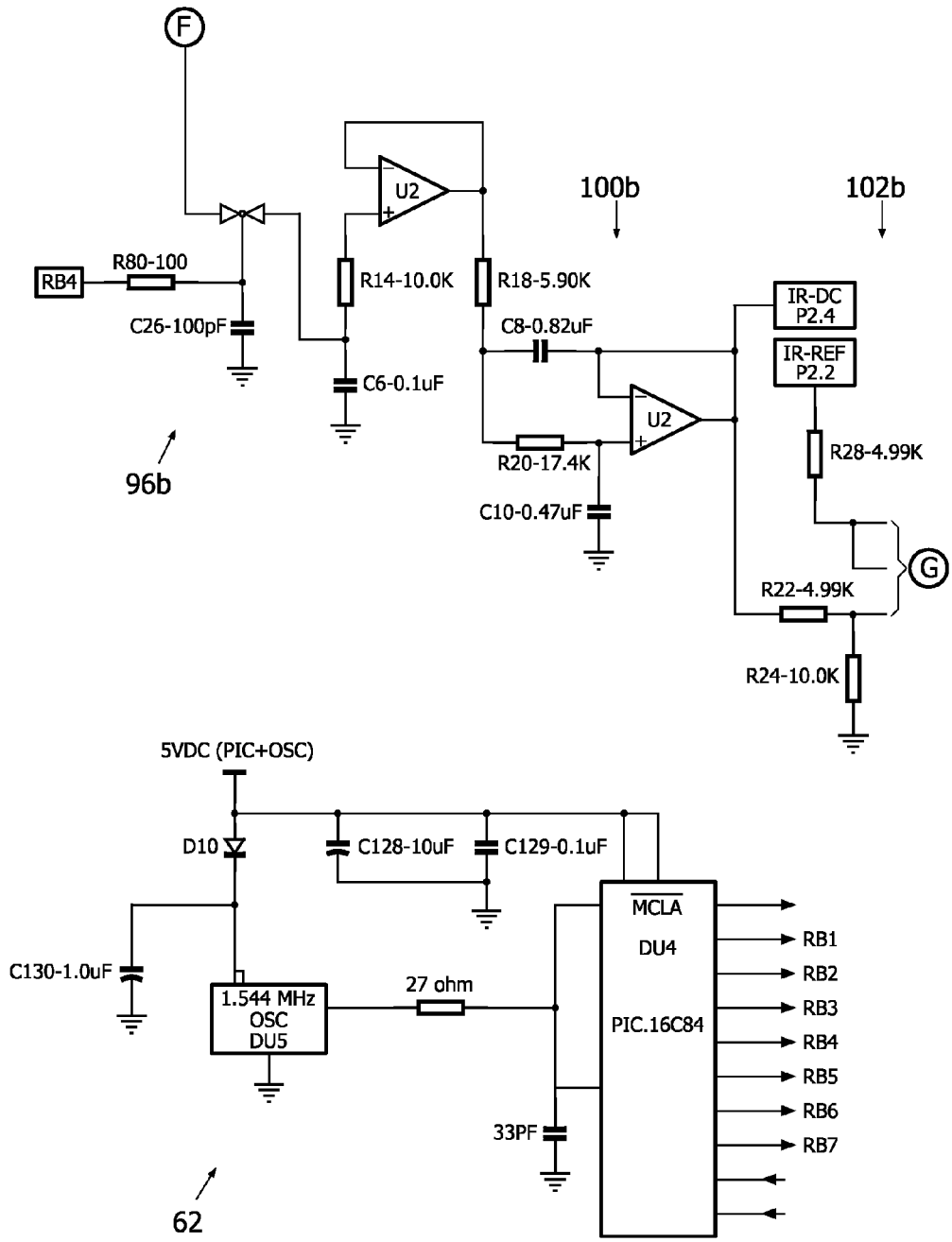
FIG. 5-V

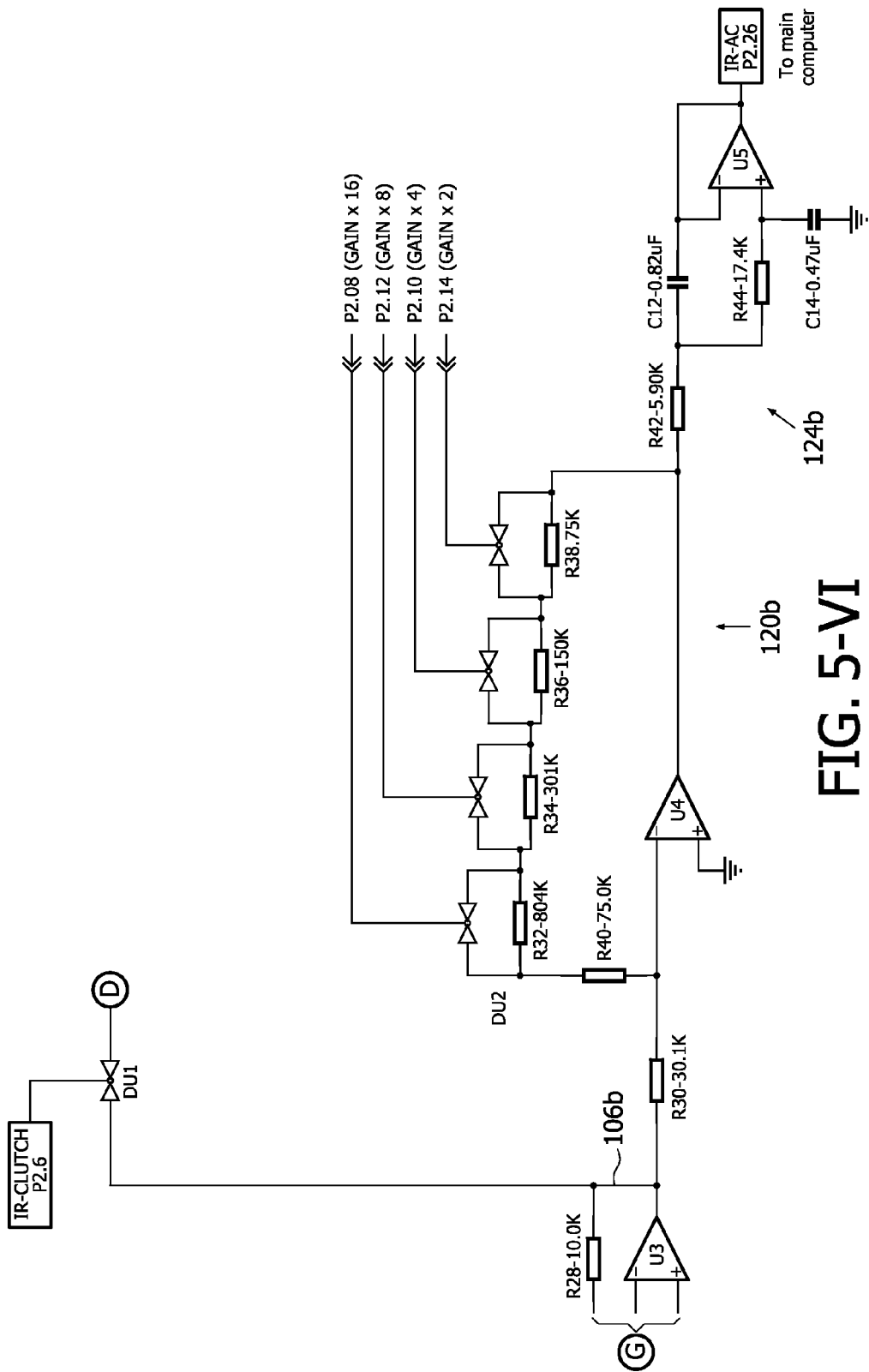
FIG. 5-VI

Summary

| Tidal Vol: | XXXX mL | SpO2: | 91 % |
| --- | --- | --- | --- |
| Peak Q I/E: | XXX/XXX LPM | Pulse Rate: | 117 BPM |
| RR: | XX.X BrPM | Est. Shunt: | Error-no FiO2 |
| I:E Ratio: | XX.X : XX.X | PIP: | XX cmH2O |
| Ve: | XXXX LPM | PEEP: | XX cmH2O |
| RSBI: | XXX | Dyn. Comp: | XX.X mL/cmH2O |
| Sup Flow: | XX.X LPM | Th Delta D: | XXX um |
| FIO2: | XX % | C Delta D': | X.XX % |
| I Slope | XX degrees | | |

FIG. 29

APPARATUS AND METHOD FOR MONITORING PRESSURE RELATED CHANGES IN THE EXTRA-THORACIC ARTERIAL CIRCULATORY SYSTEM

CROSS-REFERENCE TO RELATED APPLICATIONS

This application claims priority under 35 U.S.C. § 119(e) from provisional U.S. patent application No. 60/525,954 filed Dec. 1, 2003, the contents of which are incorporated herein by reference.

BACKGROUND OF THE INVENTION

1. Field of the Invention

The present invention pertains to a method and apparatus for monitoring changes in the intra-thoracic pressure of a patient due to the patient's respiratory activity or cardiac function, and, in particular, to a first technique in which pleural pressure changes due to respiratory effort are monitored based on the changes in pressure in the patient's extra-thoracic arterial circulatory system, and to a second technique in which a patient's vessel distention in the extra-thoracic arterial circulatory system due to respiratory activity or cardiac function are monitored.

2. Description of the Related Art

Numerous patients arrive at a hospital's emergency room each day complaining of a respiratory disorder, such as difficulty breathing, wheezing, shortness of breath, etc. Many of these patient's are incapable of communicating effectively with their physician, for example they may be too young, incapacitated in some way, or have a mental deficiency that prevents effective communication with their caregivers. It would be desirable in such situations if a technique existed for monitoring their respiratory function independent of the patient's ability to communicate, i.e., with regard to the patient's description of the problem. Such a technique would also serve as an objective evaluator of a patient's condition, even if subjective communication were possible.

Conventional methods of assessing respiratory function, including work of breathing, include visually monitoring the respiratory effort of the patient, for example, by observing whether the patient is having difficulty breathing. This provides no objective, measurable indication of the patient's well-being.

A more invasive, yet more objective pulmonary effort measuring technique involves placing an esophageal catheter in the patient's airway and monitoring the pressure within the patient's esophagus. It is also possible to monitor a patient's work of breathing using a mechanical ventilator. However, this requires attaching the patient to the ventilator. These methods are invasive and, therefore, have limited application. For example, when an asthma patient enters the emergency department of a hospital, he or she is usually not on a ventilator, yet work of breathing needs to be assessed and treated immediately. In the ICU, a significant number of patients are at high risk for respiratory failure or have recently been extubated. These patients are not on a ventilator, yet monitoring their work of breathing weighs significantly in the plan of care prescribed for them.

There is also a tremendous need to understand interactions between the heart and lungs of patients in the ICU. For example, any obstructive or restrictive disease, such as chronic obstructive pulmonary disease (COPD) or congestive heart failure (CHF), will result in increased intra-thoracic pressure swings. If the patient's work of breathing is high, blood flow from the heart changes within each breath. To date, a tool does not exist that can illustrate these interactions. Another example occurs when high ventilator pressures are needed. With each ventilator breath, blood flow from the heart changes within each breath. Thus, it is important to determine how low the ventilator pressures need to be to provide adequate ventilation without altering blood flow from the heart. This determination is very difficult to make because the determination will be different for each patient. Without an objective measurement of the hemodynamic effect, this determination cannot be made.

Finally, it is known to monitor the blood pressure of a patient to detect a symptom of a heart disease. For example, it is known to monitor a patient's blood pressure for pulsus paradoxis, which is a greater than normal decrease in systolic pressure and pulse wave amplitude during inspiration. Pulsus paradoxis is associated with circumstances in which respiration is labored and often accompanies such conditions as emphysema, pulmonary embolus, cardiac tamponade, lung cancer, or CHF. Other symptoms of heart disease include:

(1) "waterhammer" pulse, which is associated with aortic insufficiency, and is characterized by a rapid pressure upstroke and rapid fall into diastole;

(2) anacrotic pulse, which is associated with aortic stenosis and characterized by a delayed pulse upstroke;

(3) dicrotic pulse, which is associated with decreased arterial tone and is characterized by an accentuated secondary pulse wave that may feel like heart rate is twice as fast as normal;

(4) pulsus bisferiens, which is associated with combined aortic stenosis and insufficiency and is characterized by double peaks in the pulse waveform; and (5) pulsus alternans, which is usually associated with heart failure and is characterized by a large pulse wave followed by a small secondary wave.

Conventional non-invasive blood pressure monitors are only capable of taking a "snap shot" of the patient's blood pressure, i.e., the peak systole and diastole pressure, each time the blood pressure is measured. Thus, they are not suited to detect the dynamic blood pressure changes associated with these blood pressure related symptoms of heart disease.

It is known to monitor the blood pressure continuously, so that blood pressure related symptoms of heart disease, such as pulsus paradoxis, can be readily detected. However, conventional continuous blood pressure monitors are invasive; requiring locating a pressure sensor within the patient's arterial circulatory system.

SUMMARY OF THE INVENTION

Accordingly, it is an object of the present invention to provide a cardio-pulmonary monitoring system that overcomes the shortcomings of conventional monitoring techniques. This object is achieved according to one embodiment of the present invention by providing an extra-thoracic monitoring system that includes a sensing means to detect a physiological characteristic of a patient associated with pressure changes in such a patient's circulatory system and for outputting a first signal indicative of such pressure changes. The system also includes a processing means to produce a thoracic pressure signal as a measure of such a patient's intra-thoracic pressure due to respiration. This is accomplished in the processing means by isolating breath related pressure variations in the first signal from the sensing means. This enables the patient's respiratory effort to be monitored.

It is yet another object of the present invention to provide a method of monitoring the pulmonary function of a patient that does not suffer from the disadvantages associated with conventional monitoring techniques. This object is achieved by providing a method that includes detecting a physiological characteristic of a patient associated with pressure changes in such a patient's circulatory system and for outputting a first signal indicative of such pressure changes. The method also includes producing a thoracic pressure signal as a measure of such a patient's thoracic pressure due to respiration by isolating breath related pressure variations in the first signal.

It is a further object of the present invention to provide a system and method for measuring a fractional concentration of oxygen inhaled by a patient ($FO_2$). This measurement technique can be used alone or in conjunction with the cardiopulmonary monitoring system discussed above. The $FO_2$ monitoring system includes a patient circuit adapted to communicate a flow of breathing gas to an airway of a patient and a first flow sensor associated with the patient circuit. The first flow sensor quantitatively measures a flow of gas ($Q_T$) inhaled, exhaled, or inhaled and exhaled by a patient. The $FO_2$ monitoring system also includes an oxygen conduit adapted to be coupled to an oxygen source and to the patient circuit to communicate oxygen from the oxygen source to such a patient. A second flow sensor is associated with the oxygen conduit to quantitatively measure a flow of the oxygen ($Q_{O2}$) in the oxygen conduit. A processing system determines the $FO_2$ based on the output of the first flow sensor and the second flow sensor. The processing system is also capable of determining the average fractional concentration of oxygen inhaled by a patient over one breath ($FIO_2$) by identifying the respiratory cycle.

It is yet another object of the present invention to provide a system and method for displaying patient information, which can be used alone or in combination with the pulmonary monitoring system or method and/or the $FO_2/FIO_2$ monitoring system and method discussed above. The patient information display system includes means for determining fractional concentration of oxygen inhaled by a patient during one breathing cycle, means for measuring a pulse oximetry arterial oxygen saturation ($SpO_2$) of such a patient, a display having a display area, and a display controller. This display controller causes a nomogram illustrating a relationship between the measured $SpO_2$, the $FIO_2$, and an estimated shunt, to be displayed in a first field on the display area. The nomogram shows the $SpO_2$ on a first axis, the $FIO_2$ on a second axis, and a plurality of curves. Each curve corresponds to a common estimated shunt percentage. The display controller causes an indicator to be displayed on the nomogram at a location defined by coordinates corresponding to a current value of the $SpO_2$ and the $FIO_2$. This provides a readily visible indication of the estimated shunt based on the measured $SpO_2$ and the $FIO_2$ values.

It is a still further object of the present invention to provide a cardiac monitoring system that overcomes the disadvantages associated with conventional blood pressure monitoring techniques. This object is achieved according to one embodiment of the present invention by providing a non-invasive cardiac monitoring system that includes a photoemitter adapted to direct light into the tissue of a patient and through a portion of the patient and a photodetector adapted to receive light after having been transmitted through or having been reflected from a portion of such a patient. A processor produces a cardiac pressure signal as a measure of the patient's vascular pressure due to cardiac function by isolating cardiac related pressure variations in the first signal. This enables the present invention to monitor changes in the patient's blood pressure non-invasively and substantially continuously for detecting symptoms of cardiac dysfunction. The system of the present invention is also capable of measuring heart rate and monitoring heart rate variations that occur within each breath.

It is yet another object of the present invention to provide a method of monitoring the cardiac function of a patient that does not suffer from the disadvantages associated with conventional blood pressure monitoring techniques. This object is achieved by providing a method that includes: (1) passing light through a portion of the patient, (2) receiving light after having been passed through the patient, (3) outputting a first signal based on the received light, and (4) producing a cardiac pressure signal as a measure of the patient's vascular pressure due to cardiac function by isolating cardiac related pressure variations in the first signal. As noted above, this enables the present invention to monitor the patient's blood pressure non-invasively on a substantially continuous basis for detecting a symptom of a cardiac disorder.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 4 is a schematic diagram of the hardware components of the extra-thoracic monitoring system of FIG. 3;

FIG. 5 is a detailed circuit diagram corresponding to the schematic diagram of FIG. 4;

FIGS. 25-33 are screen shots of visual displays in a user interface for use with the extra-thoracic monitoring system of the present invention.

DETAILED DESCRIPTION OF THE PRESENTLY PREFERRED EMBODIMENTS OF THE INVENTION

Figure 1:
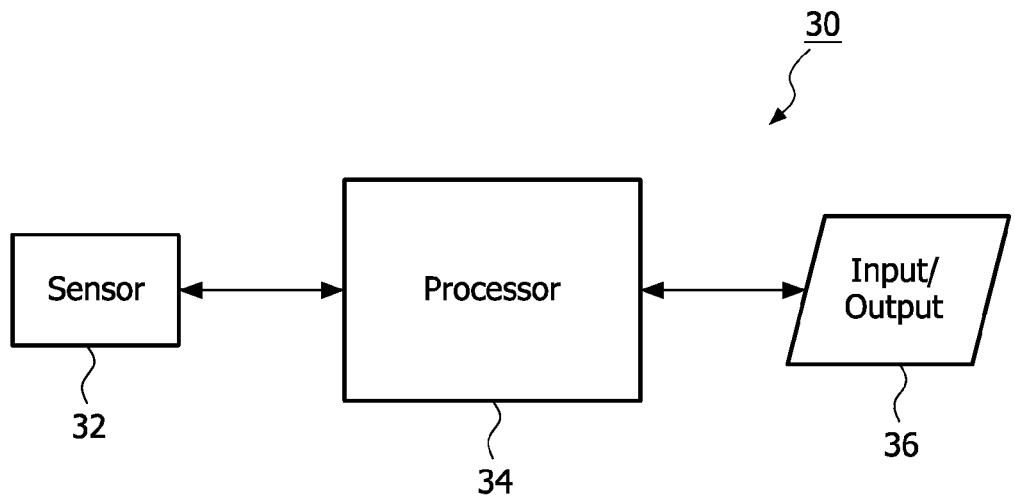
FIG. 1 is a schematic diagram of the basic components of an extra-thoracic monitoring system according to the principles of the present invention.

Mammals displace blood from within the thorax to the extra-thoracic circulation with each heartbeat and with each breath. The displacement of blood from the thorax by the heart is due to the volumetric discharge of blood from the heart into the arterial system, and, in particular, into the aorta. For example, the work of the heart changes the pressure of the blood in the thoracic vessels relative to that in the systemic circulation. In addition, respiration or breathing also causes a pressure change in the thorax, and, hence, displacement of blood from the thorax to the extra-thoracic circulation. For purposes of the present invention, the changes in volumetric discharge of blood from the heart that cause a measurable distention of the extra-thoracic arterial circulation and the pressure changes in the thorax that occur during each heartbeat and during each respiratory cycle that also cause a measurable distention of the extra-thoracic arterial circulation are collectively referred to as an "intra-thoracic pressure" changes.

Volumetric flow is the result of a pressure gradient. Thus, changes in intra-thoracic pressure caused by the heart beating and the lungs breathing are reflected by changes in pressure in the extra-thoracic arterial circulation, which is more commonly known as "blood pressure", and also by changes in the extra-thoracic arterial circulation volume. That is, the amount of blood displaced systemically, as well as the blood pressure, changes with the amount of pressure generated within the thorax due to breathing and with the work of the heart. When there is an increase in the intra-thoracic pressure, the displaced volume of blood from the thorax and the blood pressure increases, causing the extra-thoracic arteries to increase in diameter. This phenomenon is referred to herein as "vessel distention."

The present invention contemplates monitoring intra-thoracic pressure changes due to respiration or cardiac function by monitoring changes in the extra-thoracic arterial circulation resulting from respiratory or cardiac induced intra-thoracic pressure changes. According to one embodiment of the present invention, the patient's intra-thoracic pressure changes that are primarily due to respiration are monitored by monitoring a characteristic of the extra-thoracic arterial circulation that is influenced by the respiratory induced intra-thoracic pressure changes. In essence, this embodiment of the extra-thoracic monitoring system provides an indirect pleural pressure monitor that effectively acts as a surrogate to placing an esophageal pressure monitor in the patient. One potential application for this embodiment of the present invention is to monitor a patient's respiratory effort, also know as work of breathing. The greater the respiratory effort, the greater the change intra-thoracic pressure, which the present invention monitors from the patient's extra-thoracic arterial circulation.

In another embodiment, the patient's intra-thoracic pressure changes that are due to cardiac activity are monitored by monitoring vessel distention in the extra-thoracic arterial circulation. In essence, this embodiment of the extra-thoracic monitoring system of the present invention provides an indication of changes in blood pressure that effectively acts as a surrogate to placing an arterial line in a patient, which is a relatively invasive procedure. Because the present invention allows the monitoring of the cardiac pressure changes to take place non-invasively and substantially continuously, specific cardiac events, such as pulsus paradoxis, can be readily identified.

FIG. 1 is a schematic diagram of the basic components of an extra-thoracic monitoring system 30 according to the principles of the present invention that is capable of monitoring intra-thoracic pressure changes due to respiration or cardiac function by examining changes in the extra-thoracic arterial circulation associated with the intra-thoracic pressure changes. In its most basic form, extra-thoracic monitoring system 30 includes a sensor 32, a processor 34, and an input/output interface 36. It should be noted the monitoring system of the present invention is also referred to in this application as an "extra-thoracic monitoring system."

Sensor 32 is any sensor suitable for detecting a physiological characteristic of a patient associated with pressure changes in the extra-thoracic arterial circulation and for outputting a signal indicative of such physiological characteristic. As noted above, in one embodiment of the present invention, sensor 32 is an optical sensor that monitors vessel distension. It will be better understood upon reviewing the various embodiments of the present invention discussed below, that the types of sensors suitable for use as sensor 32 depends on the embodiment of the invention being practiced.

Processor 34 is a processing element, such as a microprocessor, that receives the output from sensor 32 and processes this data to produce the desired output. For example, the respiratory monitoring embodiment of the present invention contemplates that processor 34 produces a pulmonary pressure signal as a measure of the patient's intra-thoracic pressure due to respiration by isolating breath related pressure variations from the signal from sensor 32. On the other hand, the cardiac monitoring embodiment of the present invention contemplates that processor 34 produces a cardiac pressure signal as a measure of the patient's intra-thoracic pressure due to cardiac function by isolating cardiac related pressure variations from the signal from sensor 32. It is to understood that processor 34 includes the necessary memory and processing capability to implement the features of the present invention.

Input/output interface 36 is any device that provides the output of the processor, such as the thoracic pressure signal or the cardiac pressure signal, in a human perceivable format. In short, I/O interface 36 communicates information or data between a user and processor 34. Examples of common input/output interfaces suitable for this purpose include a keypad, strip chart, and display. Other communication techniques, either hard-wired or wireless, are also contemplated by the present invention. For example, the present invention contemplates providing a smart card terminal that enables data to be downloaded from processor 34 onto the smart card. Other exemplary, I/O interfaces and techniques adapted for use with the pressure support system include, but are not limited to, an RS-232 port, CD reader/writer, DVD reader/writer, RF link, and/or modem (telephone, cable or other). In short, any conventional technique for providing, receiving, or exchanging data with the processor are contemplated by the present invention as input/output interface 36.

I. SYSTEM ARCHITECTURE

As noted above, one embodiment of the present invention contemplates monitoring intra-thoracic pressure changes due to respiration by monitoring changes in the extra-thoracic arterial circulation resulting from the respiratory induced intra-thoracic pressure changes. Thus, for this embodiment, processor 34 receives the output of sensor 32 and produces a pulmonary pressure signal as a measure of a patient's intra-thoracic pressure due to respiration by isolating breath related pressure variations in the first signal. This pulmonary pressure signal is provided to input/output device 34.

Figure 2:
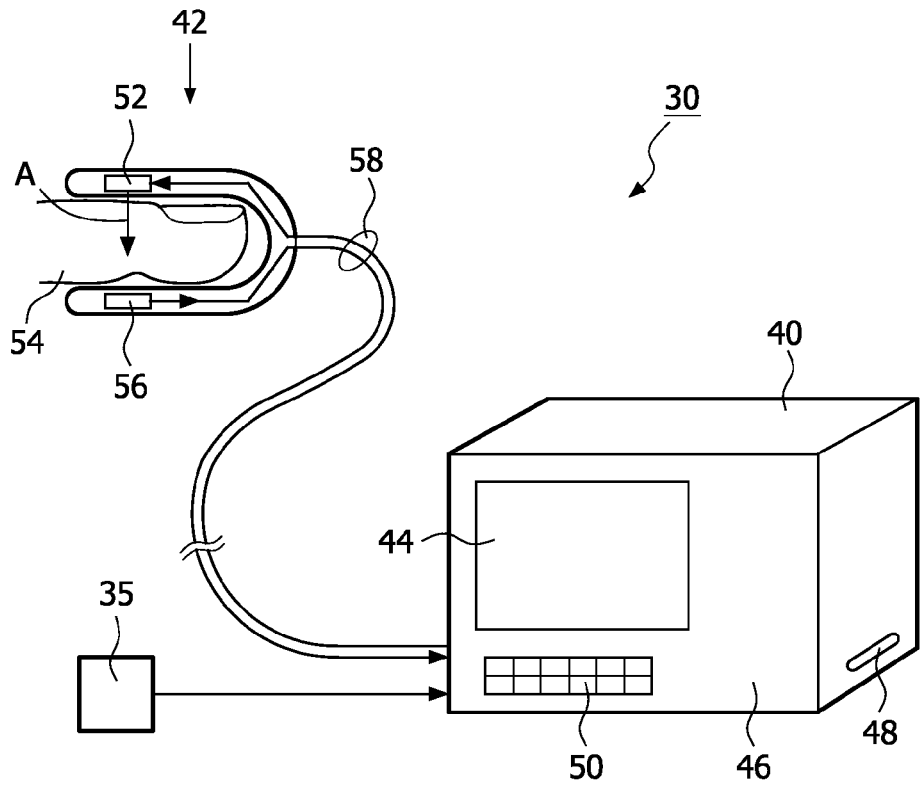
FIG. 2 is a perspective view of the extra-thoracic monitoring system showing the housing and one embodiment of a sensor suitable for use with this monitor.
Figure 3:
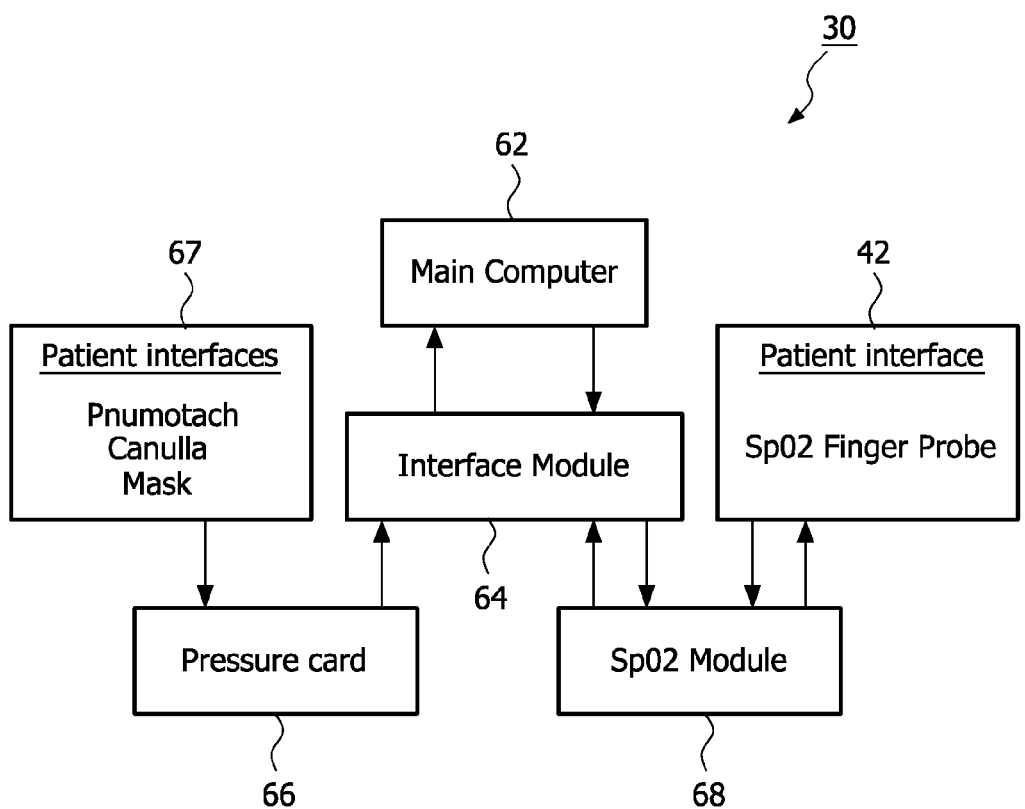
FIG. 3 is a schematic diagram of a first embodiment of the extra-thoracic monitoring system according to the present invention.

FIG. 2 illustrates one embodiment of extra-thoracic monitoring system 30 in greater detail, including a housing 40, which contains processor 34 and input/output interface 36, a respiratory sensing system 35, and an optical system 42. The respiratory and optical systems are suitable for use as sensor 32 from FIG. 1. FIG. 3 schematically illustrates a first embodiment for the components of pulmonary monitoring system 38. Referring to FIG. 2, housing 40 includes a display area 44, such as an LED, LCD, or any other conventional display, a speaker 46, and a connection terminal 48, as examples of output components of the input/output interface. Housing 40 includes a keypad 50 as an example of an input component of the input/output interface. Of course, as noted above, any conventional input/output interface, such as a touch screen or wireless communication device, is contemplated by the present invention as being suitable for interfacing a user or other peripheral device with the processing elements of the monitoring system.

Optical system 42 includes a photoemitter 52, or a plurality of photoemitters, adapted to transmit light through a portion of a patient 54, and a photodetector 56 adapted to receive light after having been passed through the patient, as indicated by arrow A. The processing elements in housing 40 that control emitter 52 and receive the signal from photodetector 56 communicate with the emitter and detector via communication lines 58. The present invention contemplates any conventional technique for communicating between the processor and photoemitter 52 and between the processor and photodetector 56. Although FIG. 2 shows the light being passed through a patient's finger, the present invention contemplates passing the light through any extra-thoracic portion of the patient where the arterial circulation can be monitored, such as the ear, toe, or nasal septum. Optical system 42 in combination with the processing elements constitutes a photoplethysmographic monitoring system that, in this embodiment, monitors the changes in vessel distention resulting from the respiratory action of the patient, spontaneous or otherwise.

In the illustrated embodiment, the optical system is a transmissive type of photoplethysmographic monitor. It is to be understood that the present invention also contemplates that the optical system is a reflective type of photoplethysmographic monitor in which light is directed into the tissue and the photodetector detects the light reflected back out of the patient.

In an exemplary embodiment of the present invention, vessel distention is determined by passing light through the finger or other appendage. As noted above, a change in blood volume causes a change in vessel diameter. The absorbance of light increases and decreases as the vessel diameter increases and decreases. The present invention measures the change in vessel distention by continuously measuring the change in absorbed light.

It should be noted that the present invention contemplates using a reflectance type of photoplethysmographic in place of the transmittance type sensor shown in the figures and described herein. In a reflectance type photoplethysmographic sensor, light is directed into the patient and the amount of light reflected back from the patient is monitored and becomes the photoplethysmographic signal. A transmittance type sensor is believed to provide a stronger signal than a reflectance type sensor.

As noted above, photoemitter 54 in optical system 42 delivers light through a portion of the patient and measures the light passing therethrough. The light signal received by detector 56 in optical system 42 is provided to the processor where it is processed in real time to separate breathing from heartbeats.

Figure 10:
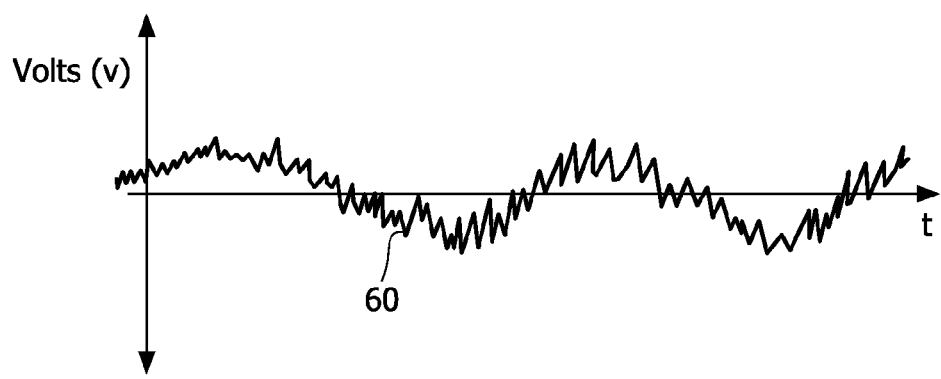
FIG. 10 is a graph of a raw hypothetical plethysmograph signal detected by the plethysmograph monitoring portion of the extra-thoracic monitoring system.

FIG. 3 schematically illustrates the components of a first embodiment of an optical sensor based pulmonary monitor 38, including the components for processing the raw photoplethysmographic signals 60 from detector 56. An example of photoplethysmographic signals 60 is shown in FIG. 10. Photoemitter 52 preferably emits light at a wavelength that is relatively insensitive to an oxygen saturation level of the patient, while relatively sensitive to changes in path length between the photoemitter and photoreceiver. That is, it is preferred that changes in oxygen saturation do not adversely influence the vessel distension measurement. This provides an advantage in that the oxygen saturation of the patient ($SpO_2$) does not have to be factored in when determining the change in vessel distention $\Delta d$. Thus, a single LED, operating, for example, and approximately 800 nm, is capable of performing the vessel distension monitoring.

Respiratory monitoring sensor 35 provides a signal indicative of respiratory rate ($f_{RR}$) or breathing frequency ($f_{breathing}$). This input is needed in some of the embodiments of the present invention to calculate the vessel distension. The present invention contemplates that any device that is capable of identifying the respiratory cycles of the patient can be used as respiratory monitoring sensor 35. For example, an effort belt provides a relatively good quality respiratory signal. Other embodiments of the present invention contemplate using a device that interfaces with a patient's airway to measure the pressure or flow at their airway, such as a nasal canula, mask, or flow sensor (pneumotach). An example of a suitable respiratory monitor is disclosed, for example, in U.S. Pat. No. 6,544,192.

FIG. 3 is a more detailed schematic diagram of a first embodiment of an extra-thoracic monitoring system 30 according to the present invention. Monitoring system 30 operates using a microcomputer system with satellite subsystems. A main computer system 62 utilizes conventional processing techniques and applications, such as Windows 2000®, Visual Basic, and Softwire, to process the received data, display results, and communicate to a interface module 64. Monitoring system 30 includes a pressure card 66 and a photoplethysmograph ($SpO_2$) module 68. Pressure card 66, photoplethysmograph module 68, interface module 64, and processor 62 define the major components of the processing system. In a preferred embodiment, the pressure card 66 and a plethysmograph ($SpO_2$) module 68 are provided as separate circuit boards to provide separate connections to the associated patient interface devices.

Interface module 64 receives and transmits analog and binary signals used to control the $SpO_2$ module and to convert those signals to digital values. In an exemplary embodiment of the present invention, pressure card 66 has four pressure sensors that physically connect to a respiratory monitoring device 35, such as a patient interface device 67, e.g., mask, nasal canula, pneumotach (differential pressure sensor that measures a pressure difference across a flow restriction). The pressure sensors on pressure card 66 that are connected to the patient interface device will depend on the patient interface device being used. The outputs of the sensors are scaled to the input voltage of the interface card for maximum voltage signals at maximum required pressure range. Computer 62 uses the digital values of this signal and calibrates it to display proper levels. The pressure card receives pressures to monitor the following parameters:

$O_2$ flow (oxygen supplied to the patient);

Patient airway pressure (the pressure of the patient airway);

Patient flow (monitored using two pressures from a pneumotach); and

Patient flow measured from a cannula or mask.

The $SpO_2$ Module is used normally to read the $SpO_2$ value or non-invasive blood $O_2$ gas of the patient. The device also conveys delta signals indicative of respiratory effort and cardiac function as well as the % Pulse Paradox at the finger probe. The $SpO_2$ Module connects to a patient interface device, such as optical system 42.

The operation of the electronic components of cardio/pulmonary monitoring system 30 according to an exemplary embodiment of the present invention will now be described with reference to FIGS. 4-7. FIG. 4 is a schematic diagram of the hardware components of the $SpO_2$ module 68 of the cardio/pulmonary monitoring system of FIG. 3, and FIG. 5 is a detailed circuit diagram corresponding to the schematic diagram of FIG. 4. FIGS. 6A-6K illustrate portions of the circuit shown in FIG. 5, and FIG. 7 is a timing diagram for the operation of the circuit shown in FIG. 5. It is to be understood that FIG. 4 and the description of the operation of the embodiment of the invention shown in FIG. 5 and presented below is intended to describe only the operation of the electronics components of the system. Details as to how the system processes the output of the $SpO_2$ module are discussed in other portions of this application.

The description of the operation of the circuit begins at finger probe 70, which also corresponds to optical system 42. Probe 70 preferably has two LED's, a Red 72 and IR (Infrared) 74. Light from the two LED's is transmitted into the finger at timed intervals. A sensor 56 in the form of a photo cell in the probe monitors the light transmitted through the finger. A timing control circuit 78 controls the operation of the LEDs. For example, there is a time period in which both LED's are turned off to measure the ambient light around the sensor. This ambient light can cause problems with the signals and needs to be removed.

Sensor 56 transmits the different levels of the signal created by each light source. (LED's/Ambient light). Transimpedance differential amplifiers 80 amplify this signal and then output it to an ambient light canceling circuit 82. See FIG. 6A.

Figure 6A:
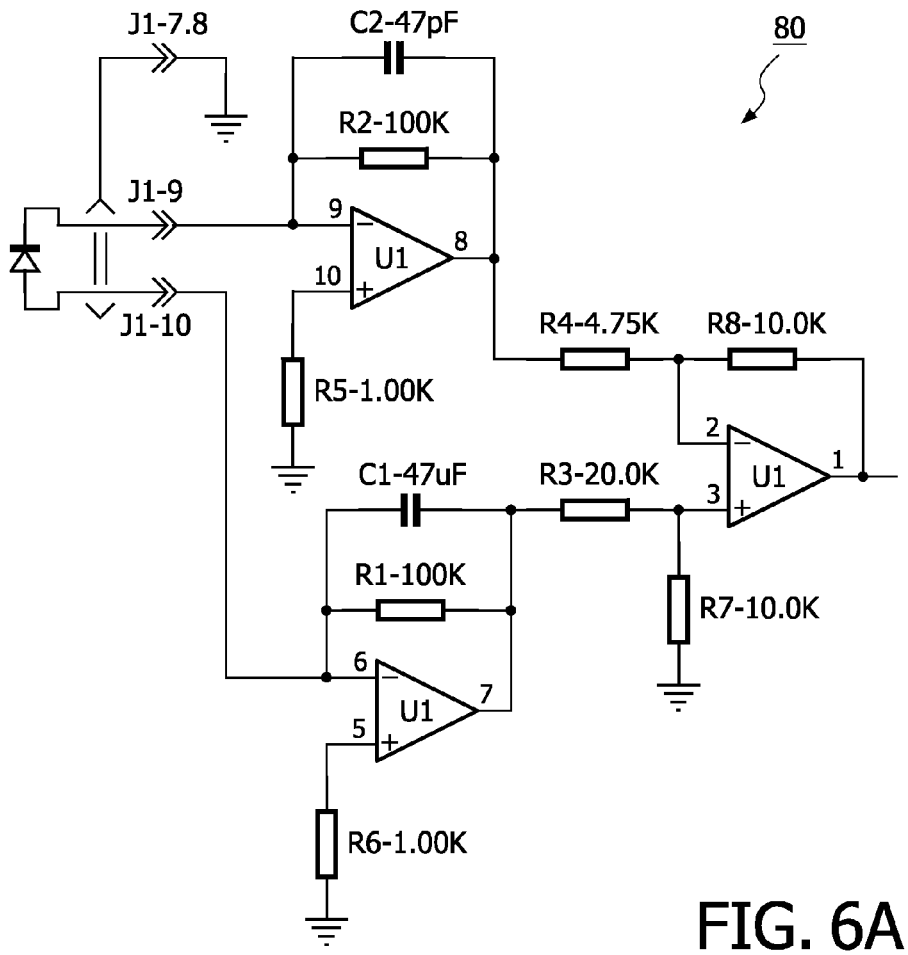
FIGS. 6A-6K illustrate portions of the circuit shown in FIG. 5.
Figure 6B:
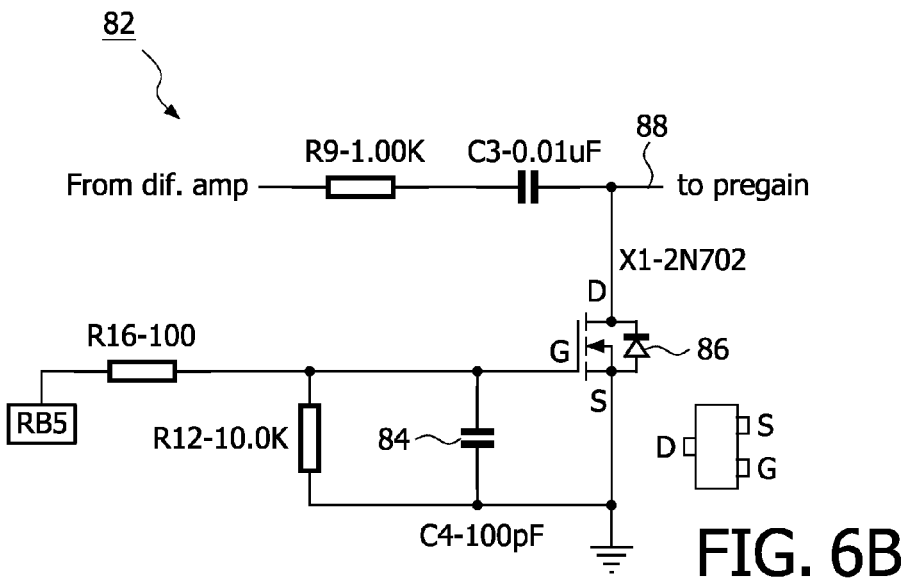
Figure 6C:
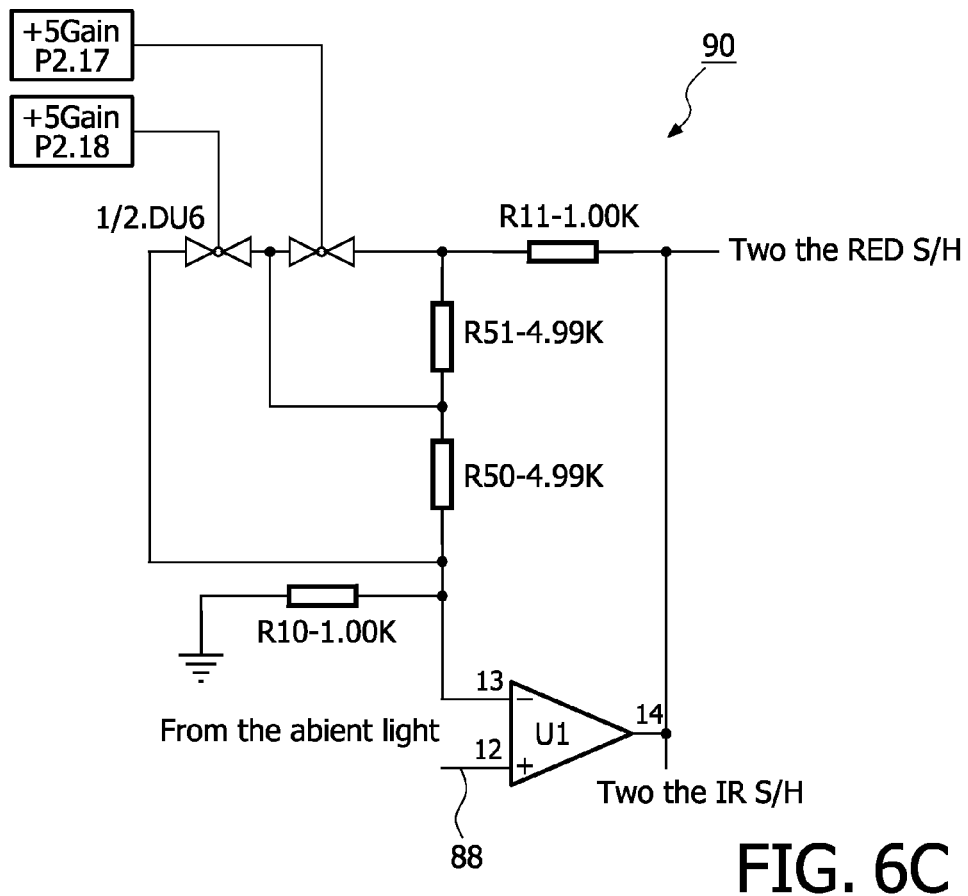
Figure 6D:
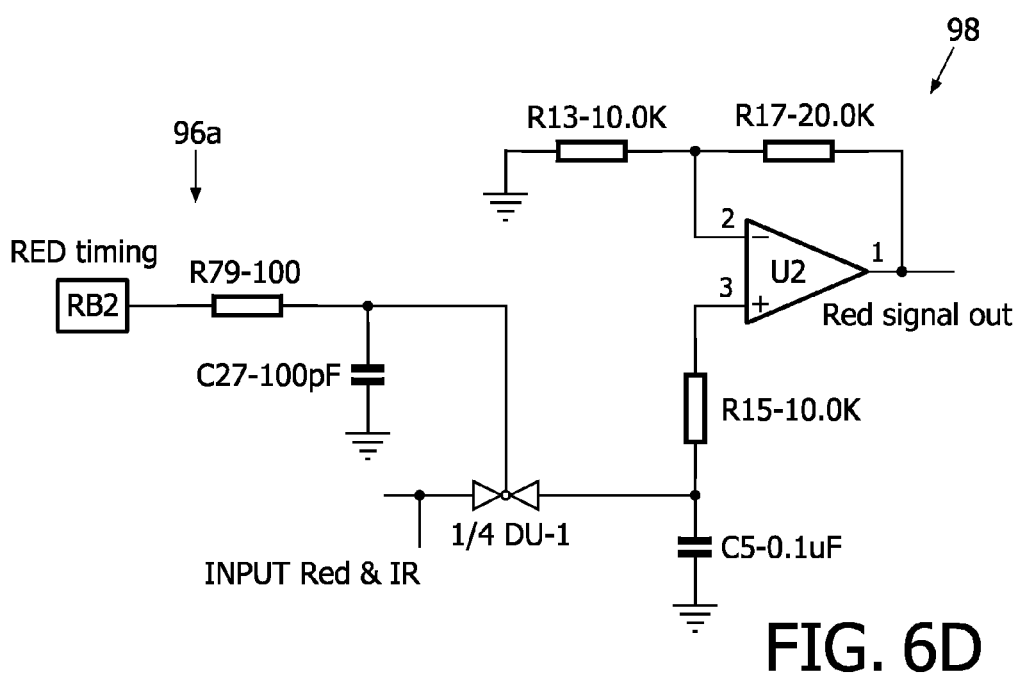
Figure 6E:
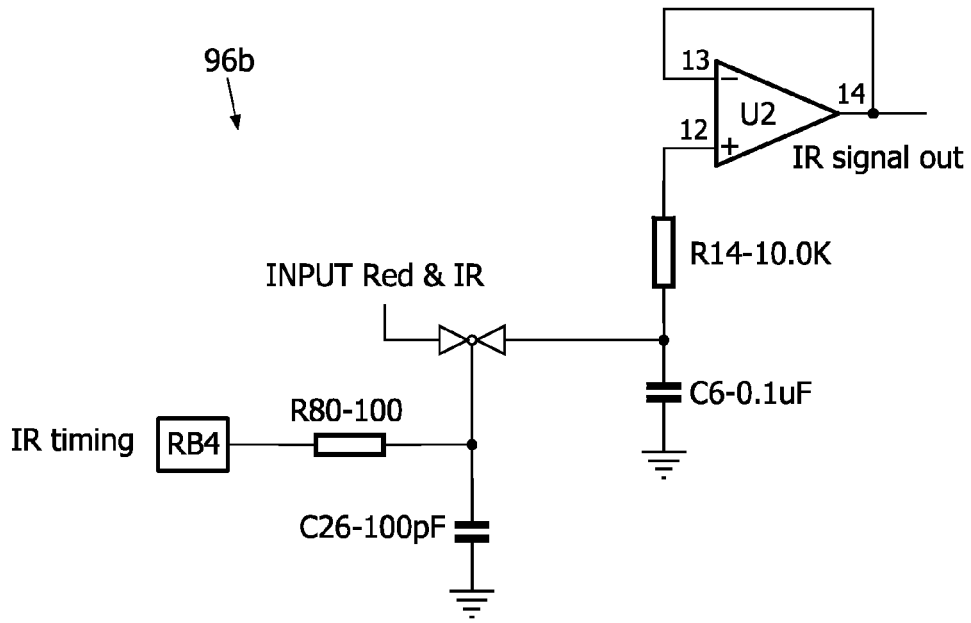
Figure 6F:
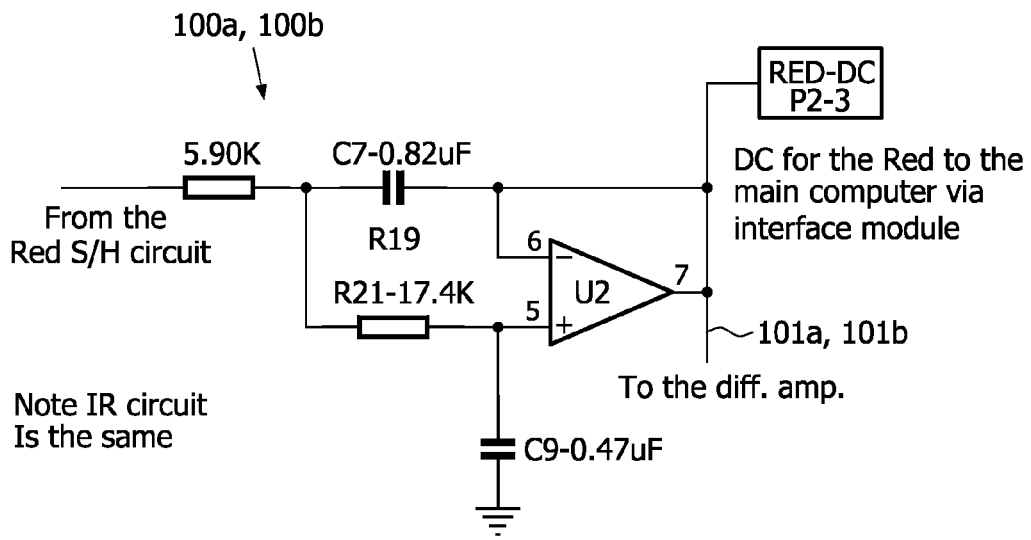
Figure 6G:
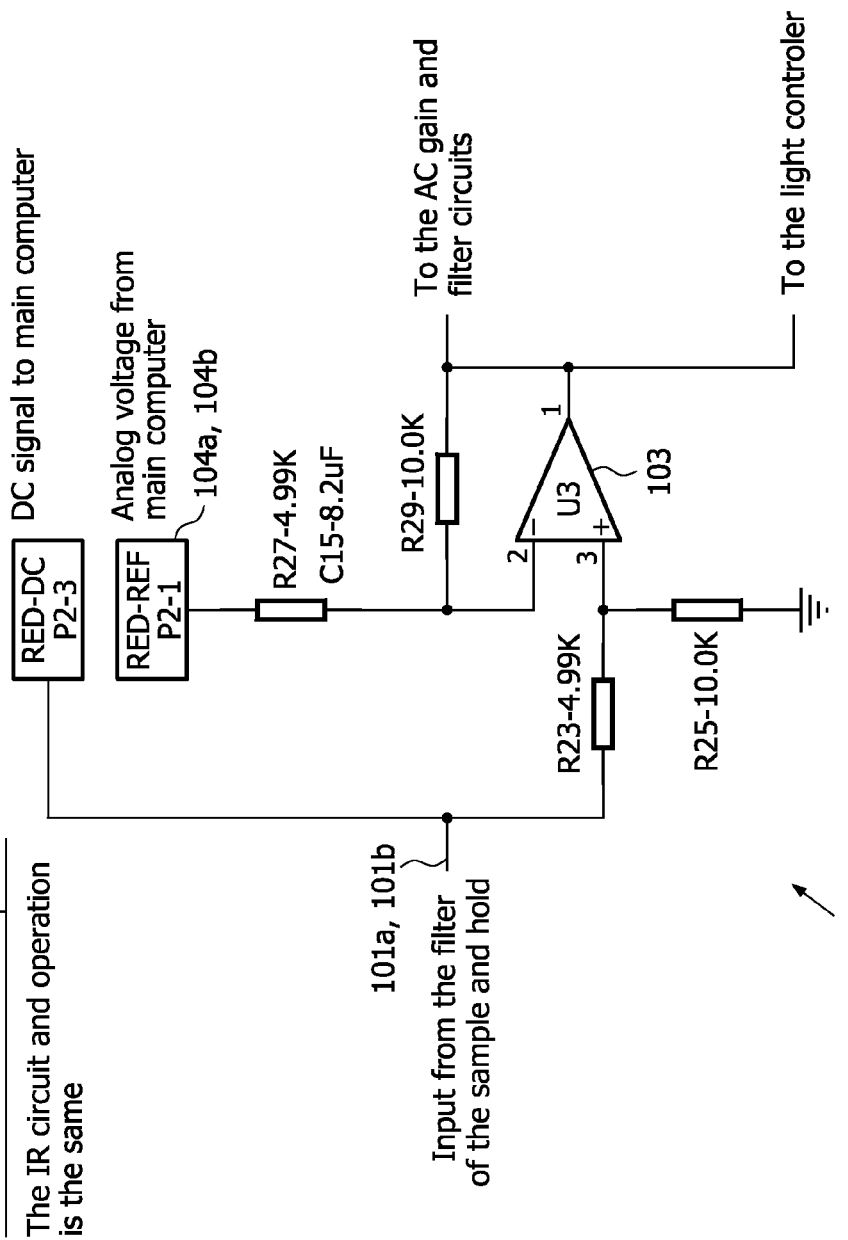
Figure 6H:
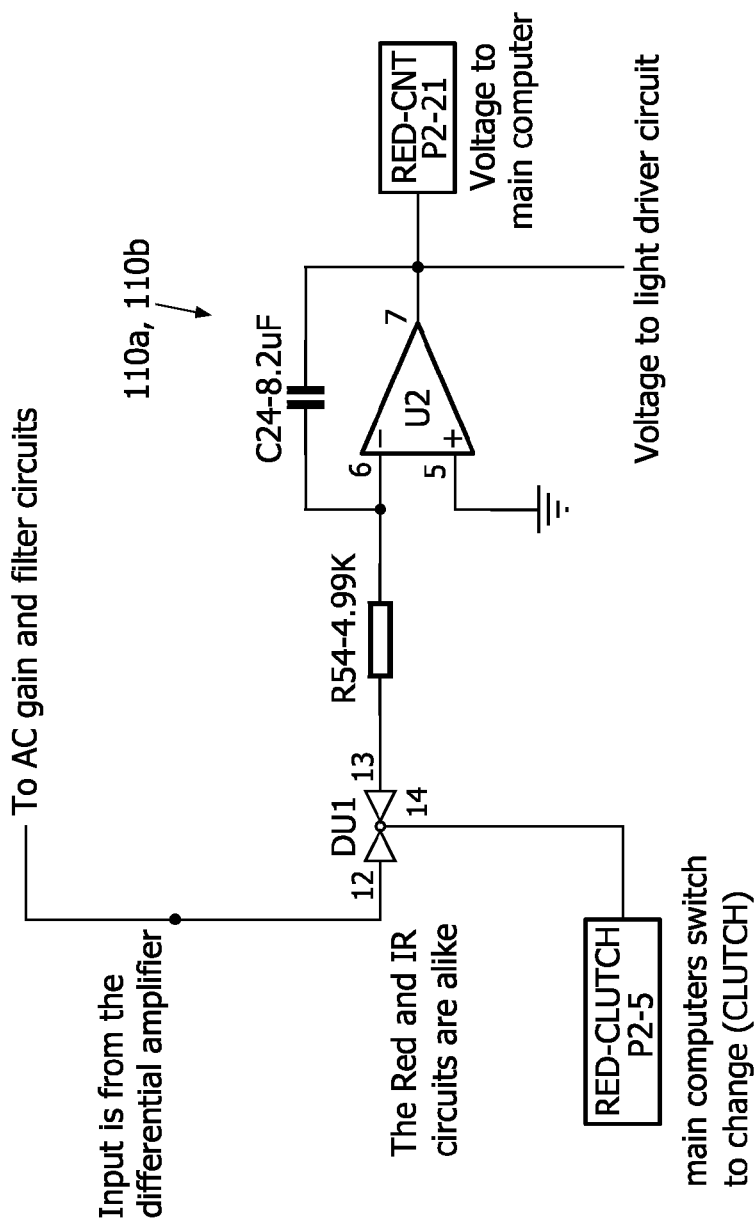
Figure 6I:
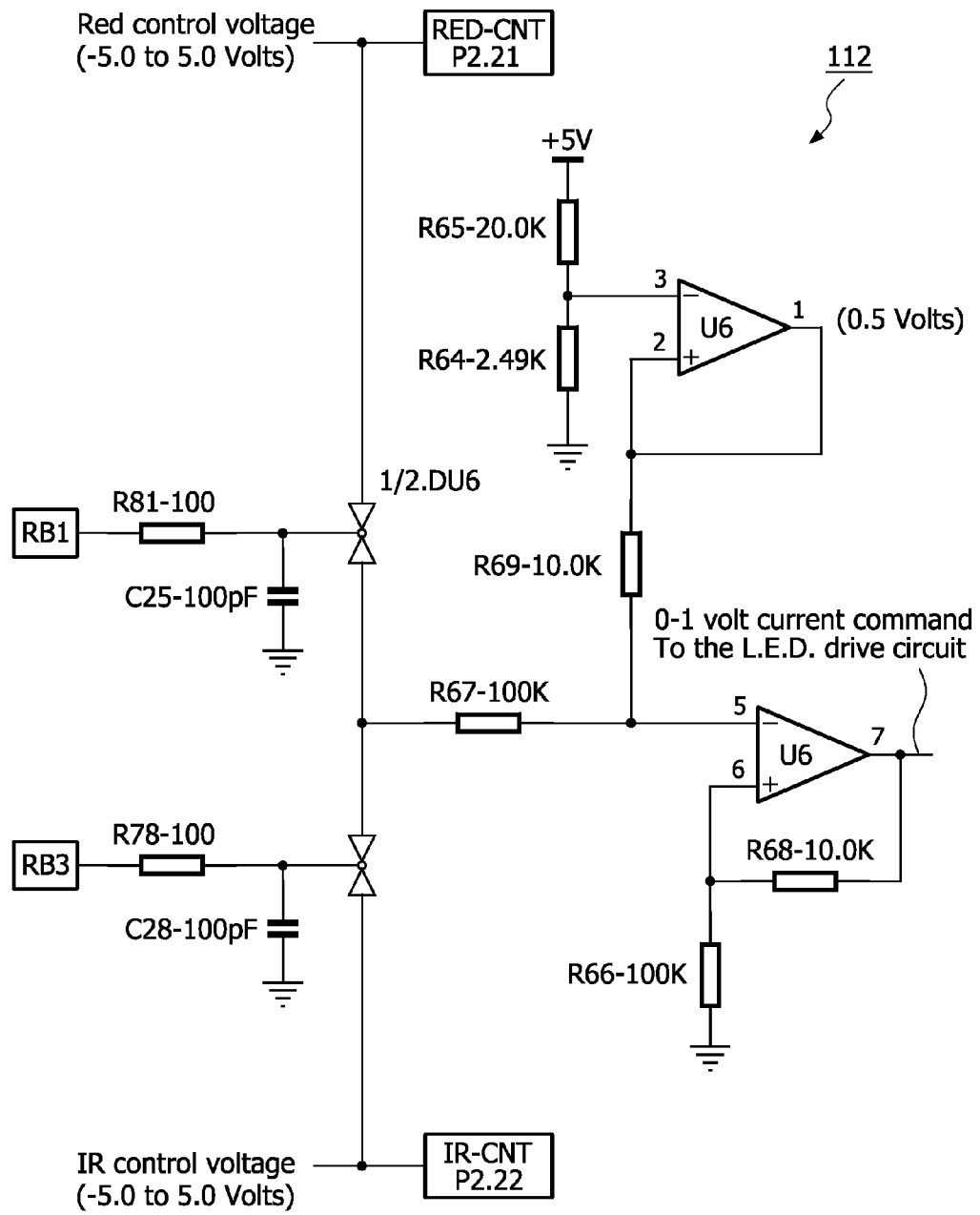
Figure 6J:
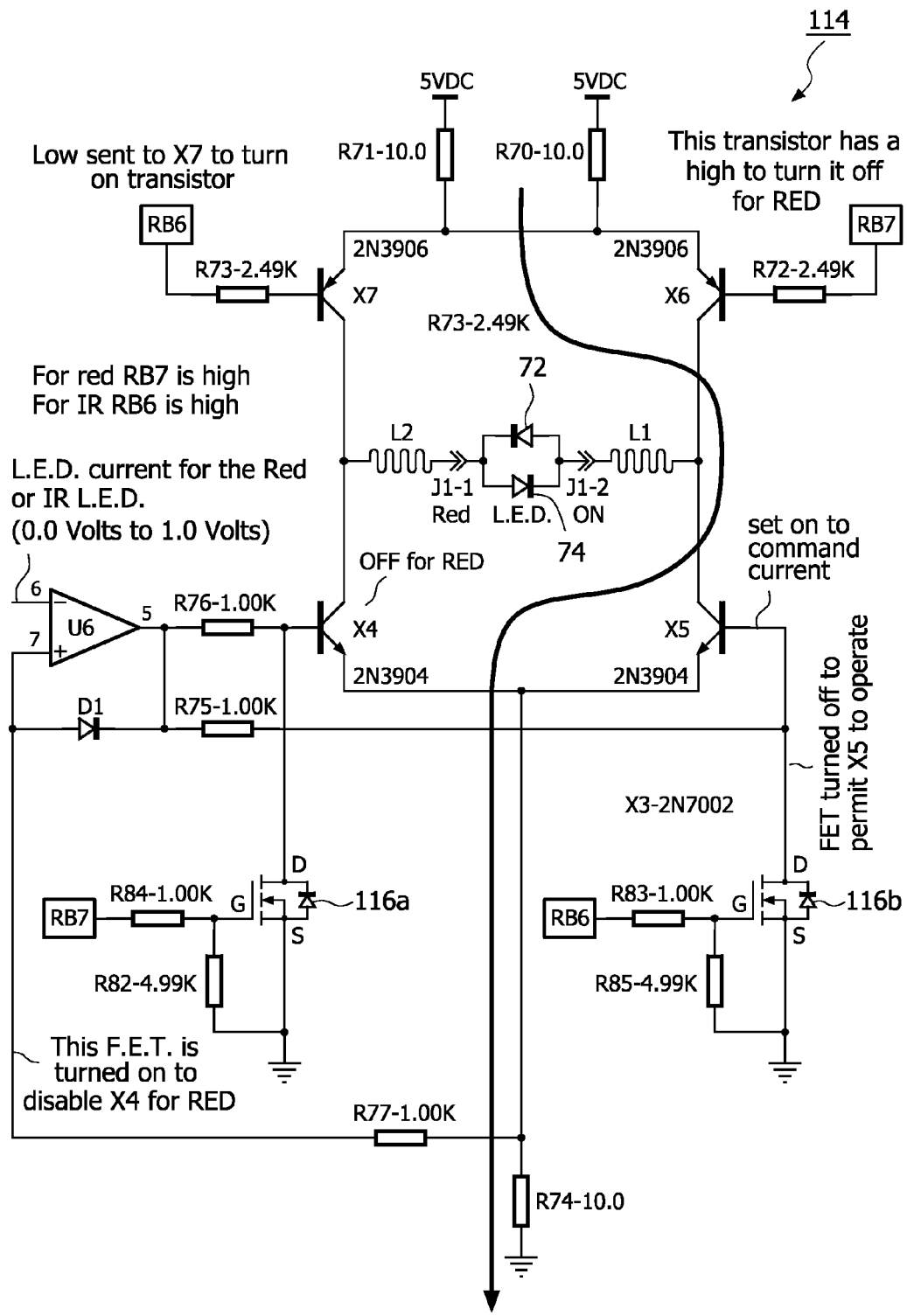
Figure 6K:
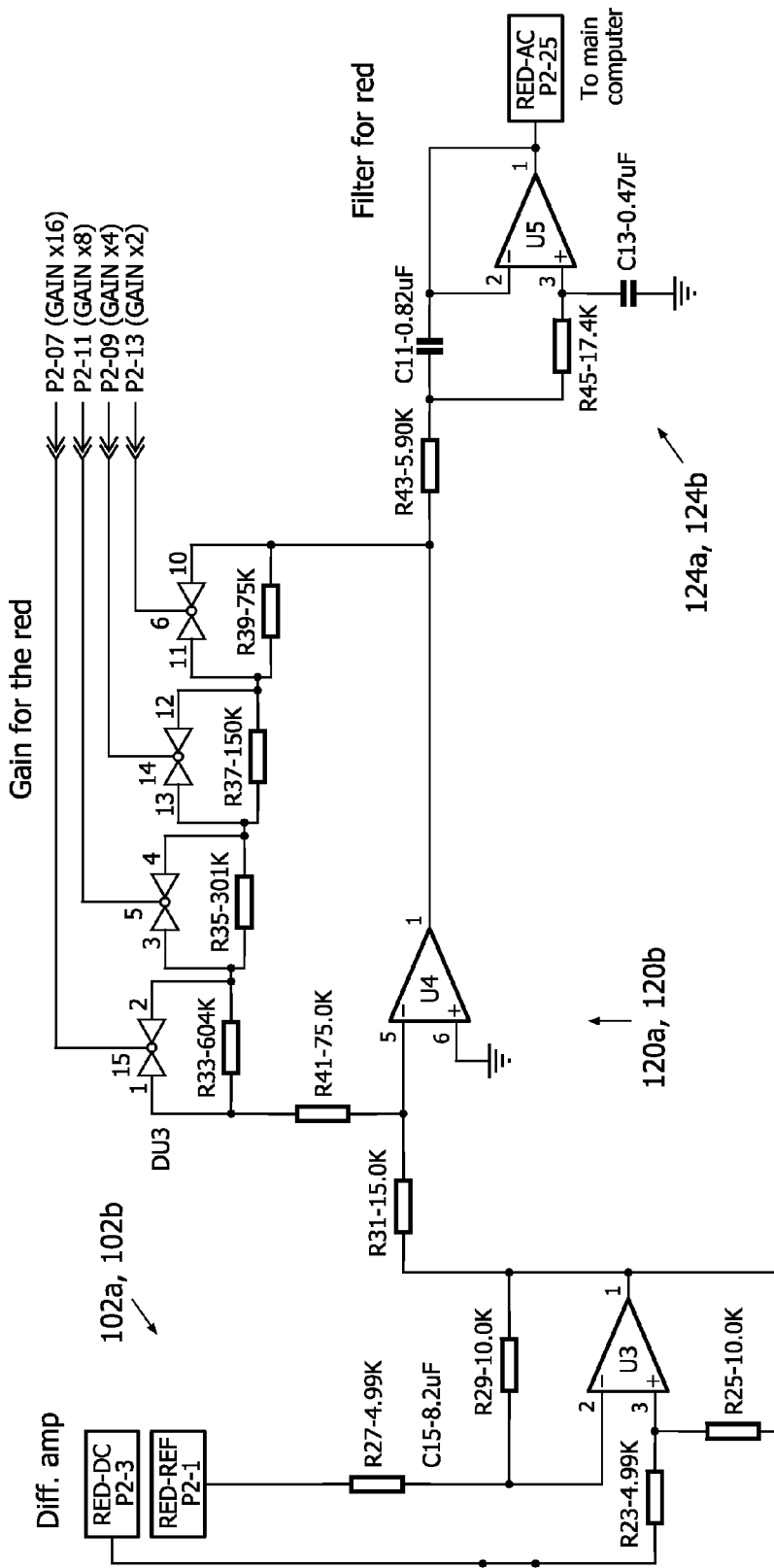
Figure 7:
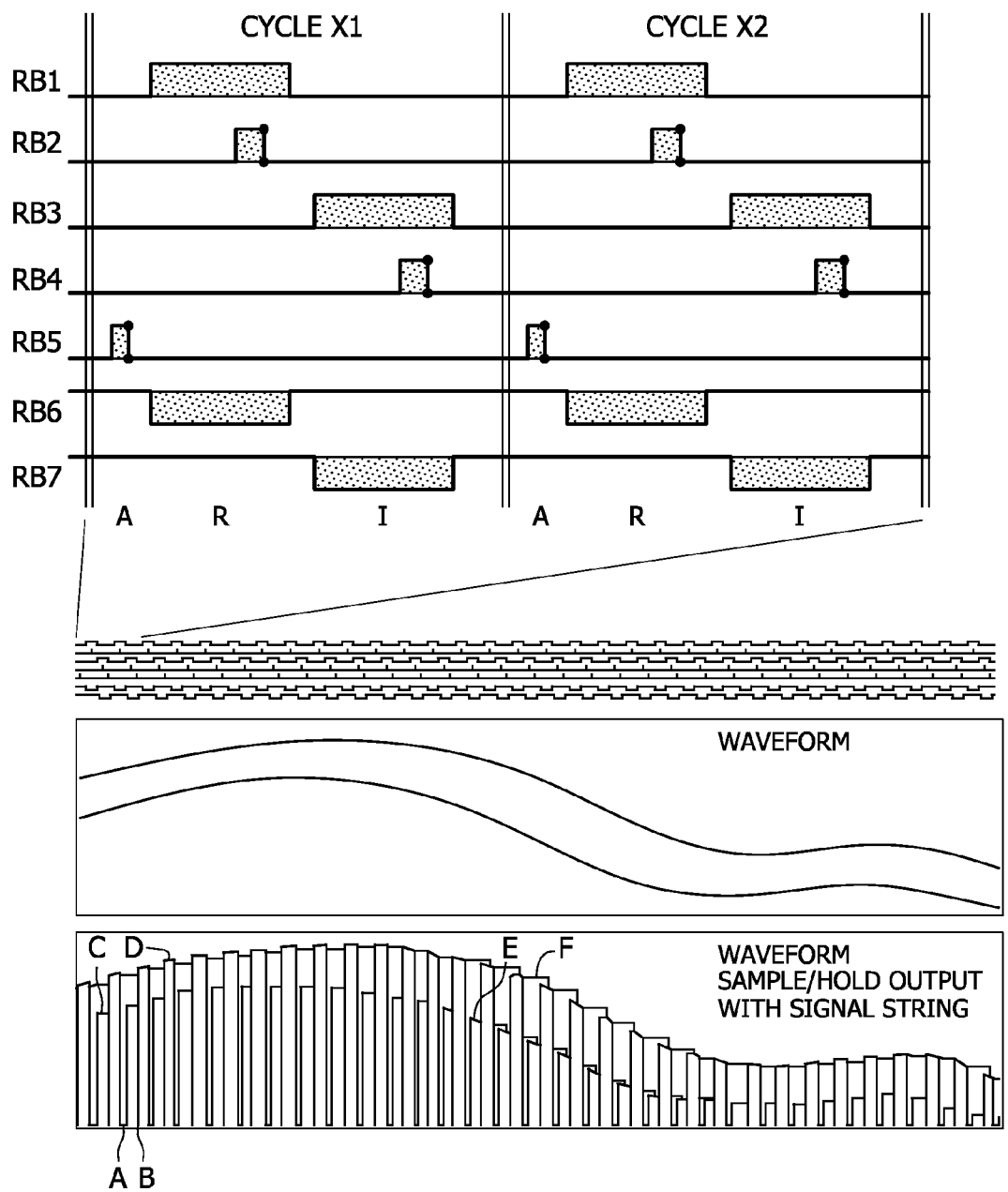
FIG. 7 is a timing diagram for the operation of the circuit shown in FIG. 5.

FIG. 6B illustrates an ambient light canceling circuit 82 that receives the output of transimpedance differential amplifiers 80. The ambient light canceling circuit operates as follows: when timing control circuit 78 has both the Red and IR LED's off, the ambient light is the only light the sensor has for an output. The Ambient light is sampled, and the value of the signal is held in a capacitor 84 tied to ground using a FET 86. When the FET is turned off, the value stored in the capacitor is used in the path of the Red and IR signal string. This stored value in the capacitor removes the error of the ambient light. The out put signal 88 now has a true value of the needed signals.

Now that the ambient light is removed from the circuit, the sensor signal needs to be adjusted for the user. This is done in a primary gain stage 90. See FIG. 6C. In a presently preferred configuration, the circuit can be adjusted between three different gains Low, Medium, and Hi. Primary gain stage 90 allows the circuit to accommodate patients with small hands or patients whose extremities are cold. In these situations, for example, too much light will be transmitted to the sensor, causing the LED in the finger probe to be forced. To prevent this, a low gain is used for the patients with small or cold hands, so that the LEDs can operate in the proper range. Detecting that the gain needs to be adjusted and providing the right gain can be accomplished automatically, via the main computer. The present invention also contemplates controlling these gains manually.

The signal from the primary gain stage is ready to be split between the RED and IR circuits. This splitting is accomplished in the present invention using a sample/hold circuit 96a and 96b. See FIGS. 6D and 6E. When the timing for the RED LED is on, a sample is taken of the signal from the sensor, and it is stored on a capacitor during the RED timing cycle. The same happens during an IR cycle, holding the value in time of the IR level from the sensor. Like points in a chart, the sample and hold circuits create the pulse plethysmograph waveforms that will be used to measure $SpO_2$. The signal from the RED LED is less than the IR signal. As a result, a gain stage is added to the Red S/H circuit.

The DC level of the signals are filtered using Low Pass Filters (LPF) 100a and 100b, e.g., a 19.9 Hz LPF, to remove switching noise from the sample/hold circuits. See FIG. 6F. The outputs 101a and 101b of the low pass filters are connected to the analog input CH03-pin8 (red) and CH04-pin 10 (IR) of the main computer, as well to a differential amplifier U3 102a and 102b. See FIG. 6G.

Each of the two Differential amplifiers (Red and IR) 102a and 102b used in this stage has two input signals, the output of the sample/hold filter 101a and 101b, and the Reference set by the main computer's analog output A0 (IR) 104a and A1 (RED) 104b. There are two functions for the analog outputs of the main computer. The first is to set up the light intensity. The main computer uses the differential amplifier to control the brightness of the finger probes LEDs. When the light is correct, the DC valve at the input of the differential amplifier equals the commanded analog signal of the main computer. The output of the differential amplifier will equal zero.

The other operation of the analog output of the computer is to keep the output of the differential amplifiers 102a and 102b inside a window of operation without adjusting the finger probes light intensity. This operation will lock out the light controller, but the voltage of the analog output will change to keep the output of the differential amplifier to zero if it should fall outside of a window range. This is like an AC coupled circuit without the delays of a capacitor and the ability to know the value of the change made.

As shown in FIGS. 4 and 5, outputs 106*a* and 106*b* of differential amplifiers 102*a* and 102*b* accomplish two functions: a light controller operation, and an AC gain and filter operation, referred to as the AC signal conditioning, to provide the input to the main computer.

During the light adjustment for brightness of the LEDs (the light controller operation), the error voltage of the DC signals (DCX (Red or IR) and the DC Ref (from computer for the red or IR)) is compared in a respective comparing circuit 110*a* or 110*b*. See FIG. 6H. The difference out of the differencing amplifier is the error voltage needed to correct the LED intensity. During this needed change of brightness, the main computer closes the switch to the integrator, causing it to adjust the control voltage of the drive circuit so that the DC value of the red or IR LED's will equal the reference voltage. At the end of this operation, the computer opens the switch and controller will freeze with the last value out.

The output of the comparing circuit 110*a* and 110*b* is provided to a Proportional level shift gain/mixing circuit 112. See FIG. 6I. To understand the operation of this circuit, it should first be noted that the LED drive circuits 78 need a voltage level of 0-1 volt to operate the LEDs. The drive circuit also needs the voltage of both LEDs set into a timing string to match its output between the RED and IR circuits. The mixing part of the circuit uses two analog switches to select between the two integrators, making a control string for the drive circuit. Because the output of the integrator is between −5 to +5 volts, the gain will need to be divided by 10 to provide the needed plus and minus 0.5 volts. The circuit will then level shift that voltage by 0.5 volts giving the needed 0-1 volt for the next stage.

The final stage 114 of the control loop (the light controller operation) is in two parts: the voltage-to-current converter, and the inverting output stage. See FIG. 6J. The current converter uses a 10-ohm sample resistor in the path of the LEDs output drive circuit. The voltage drop across the resistor should equal 10× the current or 1 Volt will equal 100 mA. Using this voltage and comparing it to the output of the control voltage, the amplifier will adjust its output voltage to adjust the current to be equal to the commanded current string.

Part two of the drive breaks down the string so that it can control the proper LED to the timing used in the other circuits. In the illustrated exemplary embodiment, NPN transistors (2N3904) (X4-X7) are used to set the current. FETs 116*a* and 116*b* (2N7002) at the base of the transistor, when turned on, will shut down the current of that leg of the H Bridge drive circuit. The PNP transistors at the top of the H Bridge drive (2N3906) also are used to shut down or enable the current to flow in the proper direction with the proper timing. For example, during the Red Drive time, the control voltage is 0.6 volts (60 mA command RED timing) RB6 will go low RB7 will remain high. Because RB6 is low, the left 2N3906 is on, allowing current to pass in that leg. The right transistor is off if RB7 is high, and no current will flow in the other leg. With RB6 low, the right 2N7002 FET will be turned off, and the control voltage of the U6 amplifier will feed the right 2N3904 transistor. The current then flows from 5 VDC down the left leg PNP transistor into the probes RED LED down the right NPN transistor and into the 10-ohm current sample resistor for the feedback for current correction of the U6 amplifier. The operation is the same for the IR LED, only RB6 is high and RB7 is low, and the other path of the H drive is used.

As noted above, the outputs of differential amplifiers 102*a* and 102*b* are provided to AC gain circuits 120*a* and 120*b* and filter circuit 124*a* and 124*b* to perform AC signal conditioning on the Red and IR signals. This is done prior to providing these signals to the main computer. These operations are discussed below with reference to FIG. 6K.

Signals from differential amplifiers 102*a* and 102*b*, which originated from the probe, contain information that can determine $SpO_2$, heart rate, and other information about the person wearing the probe. The signals also have high frequency noise, low frequency offsets, and low or high signal levels. The conditioning circuits can be broken down into three parts: (1) differential offset control, (2) gain circuits, and (3) low pass filter. Each of these three parts are discussed in turn below. Conditioned waveforms for the RED and IR are then sent to the main computer via interface module 64.

Because the system of the present invention does not use a high pass filter in the hardware, offsets can cause signals to go into the operating rail. The computer looks for this offset and adjusts the Ref. Voltage. (Note: this voltage is entered into the previous stage). This lets the computer adjust the offset correctly. Knowing the value of the offset, the data internal to the computer, can be spliced. Because the computer works in a virtual world it can simulate voltages outside of the range in which the circuit can operate.

Gain stages 120*a* and 120*b* are used to adjust the gain or peak-peak value of the signal to keep it inside a window of operation. Too much gain and the waveform will run out of voltage, distorting the peeks of signal. Too little, and the final signal will not be able to resolve the values of the waveform, reducing the accuracy of the system. In this stage, the main computer will provide the correct window of operation by adjusting the gain.

Low pass filters 124*a* and 124*b* are used to pass signals less than the chosen cutoff frequency, blocking noise and other interference signals. The 19.9 Hz low pass used has a cutoff frequency of just above the heart rate range. This means noise variations above 19.9 Hz, or frequencies above the breathing range, are reduced/removed from the waveforms that are being conditioned.

Timing for the circuit is important. A small PIC controller is used to provide the timing signals RB1 to RB7 (output pin names of the PIC control). FIG. 7 is a raw diagram of the timing and waveform creation method.

Starting with RB5 in the timing chart shown in FIG. 7 shows that the ambient light sample starts the timing for each cycle of the PIC controller. The dots illustrate when the error voltage created by the ambient light is stored. Also note that the Red and IR LEDs are off. The signal string from the probe also will show a lower or no signal, as indicate at point A at the lower end of the timing chart. (Signal waveform string is for theory only.)

The next phase of the timing cycle, is the RED timing. Setting RB6 low turns on the transistor circuit used in the drive stage to allow current through the RED LED. Next, the correct current command is passed to the output circuit by setting RB I high. The LED turns on and light stabilizes almost instantly. A delay is set to insure the LED is on and stable then RB2 is turned on sampling the waveform (see point C of the lower portion of the timing chart showing part of the waveform that is being sampled). When RB2 goes low, the voltage value is stored on the hold capacitor for the red (point E of lower cart shows one of many held voltage points). RB1 and RB6 go to their output off for the Red LED.

During the IR phase of the timing cycle, the transistor circuit used in the drive current through the IR LED is turned on by setting RB7 low. Next, the correct current command is passed to the output circuit by setting RB3 high. The LED turns on and light stabilizes almost instantly. A delay is set to insure the LED is on and stable then RB4 is turned on sampling the waveform (point D of the lower chart of FIG. 7 showing part of the waveform that is being sampled). When RB4 goes low, the voltage value is stored on the hold capacitor for the red (point F of lower cart shows one of many held voltage points). RB3 and RB7 go to their output off status for the Red LED.

II. NON-INVASIVE VESSEL DISTENSION MONITORING

Figure 8:
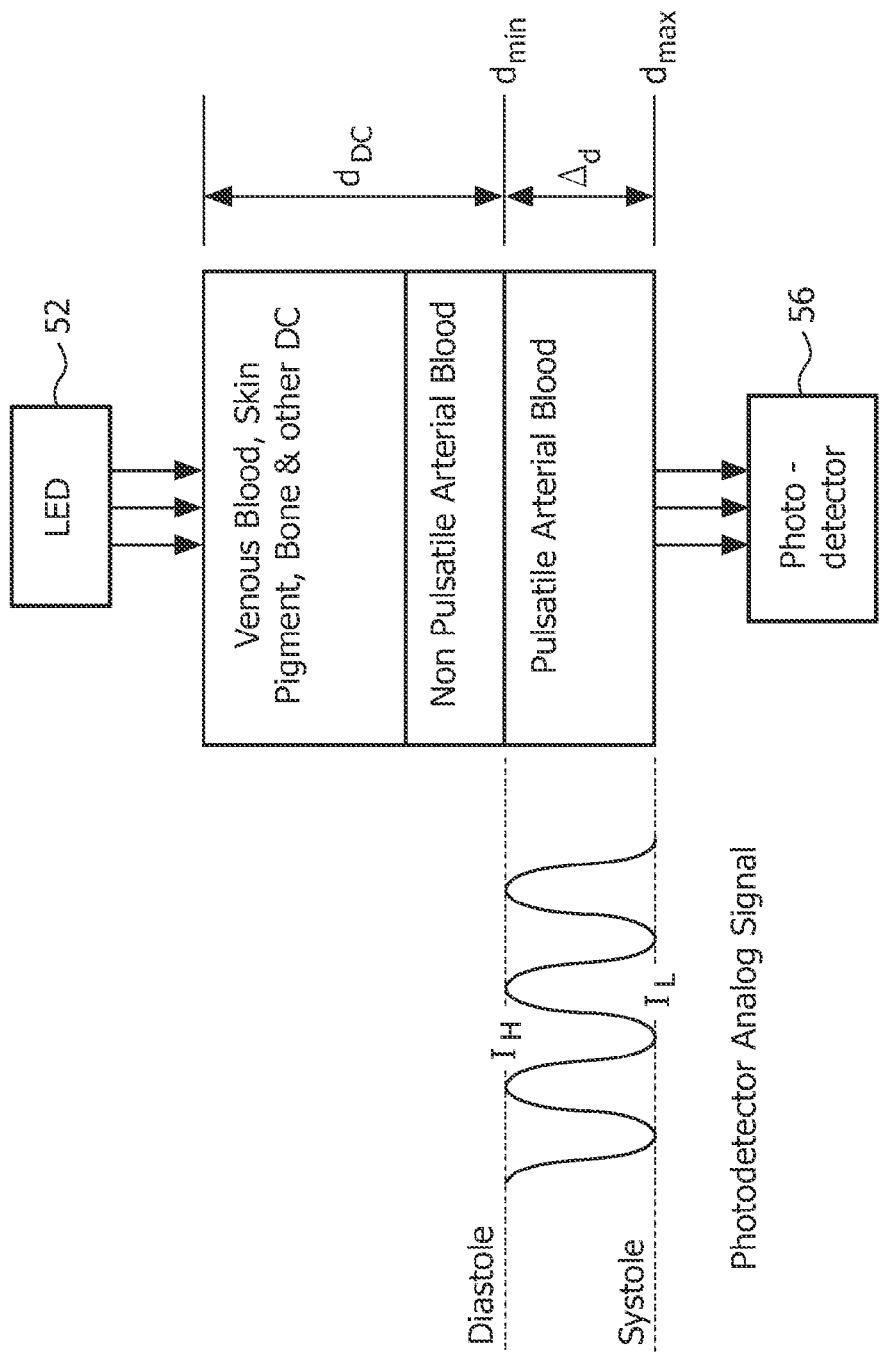
FIG. 8 is a schematic diagram of a user's tissue disposed between a photoemitter and a photodetector of the present invention.

As noted above, the present invention contemplates monitoring the patient by non-invasively monitoring the patient's vessel distension (NIVD). This is accomplished by measuring the intensity of light transmitted through the patient's tissue. FIG. 8 is a schematic diagram of the user's tissue disposed between a photoemitter 52 and a photodetector 56 of the present invention. This figures illustrates the tissues that affect the absorbance of light passing through the tissues. It can be appreciated that there are two components associated with the absorbance of light: a DC component that does not change with each heartbeat or breath; and an AC component $\Delta d$ that is the result of arterial blood pulsates due to the heart beating or breathing. FIG. 8 illustrates only changes in path length due to the cardiac activity. It can be appreciated that changes in path length due to respiration will be similar, except that $d_{min}$ ($I_H$) will coincide with the lowest pressure occurring through one respiratory cycle, and $d_{max}$ ($I_L$) will coincide with the highest pressure occurring through one respiratory cycle.

The present inventors determined that the change in path length $\Delta d$ can be determined if $SpO_2$ and the concentration of total functional hemoglobin are known. The change in path length, $\Delta d$, due to breathing, which is referred to as the Thoracic $\Delta d$ or $NIVD_{Thoracic}$, and the change in path length to the heart stroke volume, which is referred to as the Cardiac $\Delta d$ or $NIVD_{Cardiac}$, are determined using the following formula:

$$NIVD = \Delta d = \frac{-\ln\left(\frac{I_X}{I_H}\right)}{\left\{\left[(\varepsilon_{HbO_2})(\lambda_{IR}) \cdot \frac{SpO_2}{100}\right] + \left[\varepsilon_{Hb}(\lambda_{IR}) \cdot \left(1 - \frac{SpO_2}{100}\right)\right]\right\} c_{TotHb}}. \quad (1)$$

Where:

$I_X$ is the intensity of light transmitted through the tissue at any given time;

$I_H$ is the peak intensity of light transmitted through the tissue at any given time;

$\varepsilon_{HbO2}$ is the extinction coefficient for oxygenated hemoglobin, i.e., functional hemoglobin that is fully saturated with oxygen;

$\varepsilon_{Hb}$ is the extinction coefficient for reduced hemoglobin, i.e., functional hemoglobin that is not fully saturated with oxygen;

$\lambda$ is the wavelength of light being directed into the user; and $c_{TotHb}$ is the total concentration of functional hemoglobin ($c_{Hb}+c_{HbO2}$).

The total concentration of functional hemoglobin in whole blood ($c_{TotHb}$) is given by a number of sources, some to varying degrees of accuracy. The extra-thoracic monitoring system of the present invention assumes a total concentration of 2.265 milli-mole per liter (mM/L), based on a patient with normal amounts of dyshemoglobin. Other errors exist. For example, cigarette smoking temporarily "steals" small amounts of hemoglobin, creating dyshemoglobins that absorb light differently. By limiting the degree of accuracy of the total concentration of hemoglobin to 2.265 mM/L, any actual changes are so small they are most likely insignificant.

The other parameters in Equation (1) are either computed ($SpO_2$), or given ($\lambda$). In a presently preferred embodiment, an average $SpO_2$, such as an average $SpO_2$ over 2.5 seconds, is used in equation (1) to prevent a single errant event from providing unreliable results. The method for finding $I_L/I_H$, and over what time frame, becomes the main difference between the two different vascular distension measurements. All NIVD measurements are converted to micrometers by multiplying the result of equation 11 by 10,000.

Cardiac $\Delta d$ ($NIVD_{Cardiac}$) is a measure of the change in path length from one heartbeat to the next, and, by normalizing this signal over a breath, generates a percent change. Equation (1) is used to determine Cardiac $\Delta d$ by letting $I_X$ correspond to the intensity of light transmitted through the tissues at any given time, x, during one cardiac cycle, and by letting $I_H$ correspond to the peak intensity of light transmitted through the tissues during one cardiac cycle. As a result, Cardiac $\Delta d$ represents the change in diameter of the arterial vessels from their minimum value (diastole) to their value at time, x, during one cardiac cycle.

Thoracic $\Delta d$ ($NIVD_{Thoracic}$) is a measure of the effect of thoracic pressure swings on the effective path length seen at the probe site. Thoracic $\Delta d$ is an alternative to the awkward, invasive conventional technique of swallowing an esophageal balloon catheter in order to monitor thoracic pressure swings. Equation (1) is used to determine Thoracic $\Delta d$ by letting $I_X$ correspond to the intensity of light passing through the tissues at any given time, x, during one breath, and by letting $I_H$ correspond to the peak intensity of light passed through the tissues during one breath. The diameter of the arterial vessels are at a minimum when the lung pressure is at atmospheric pressure and ignoring any effect on vessel distension due to cardiac function. As a result, Thoracic $\Delta d$ represents the change in diameters of the arterial vessels from their minimum value to their value at time, x, during one breath;

III. OPERATION OF THE SYSTEM

Figure 9:
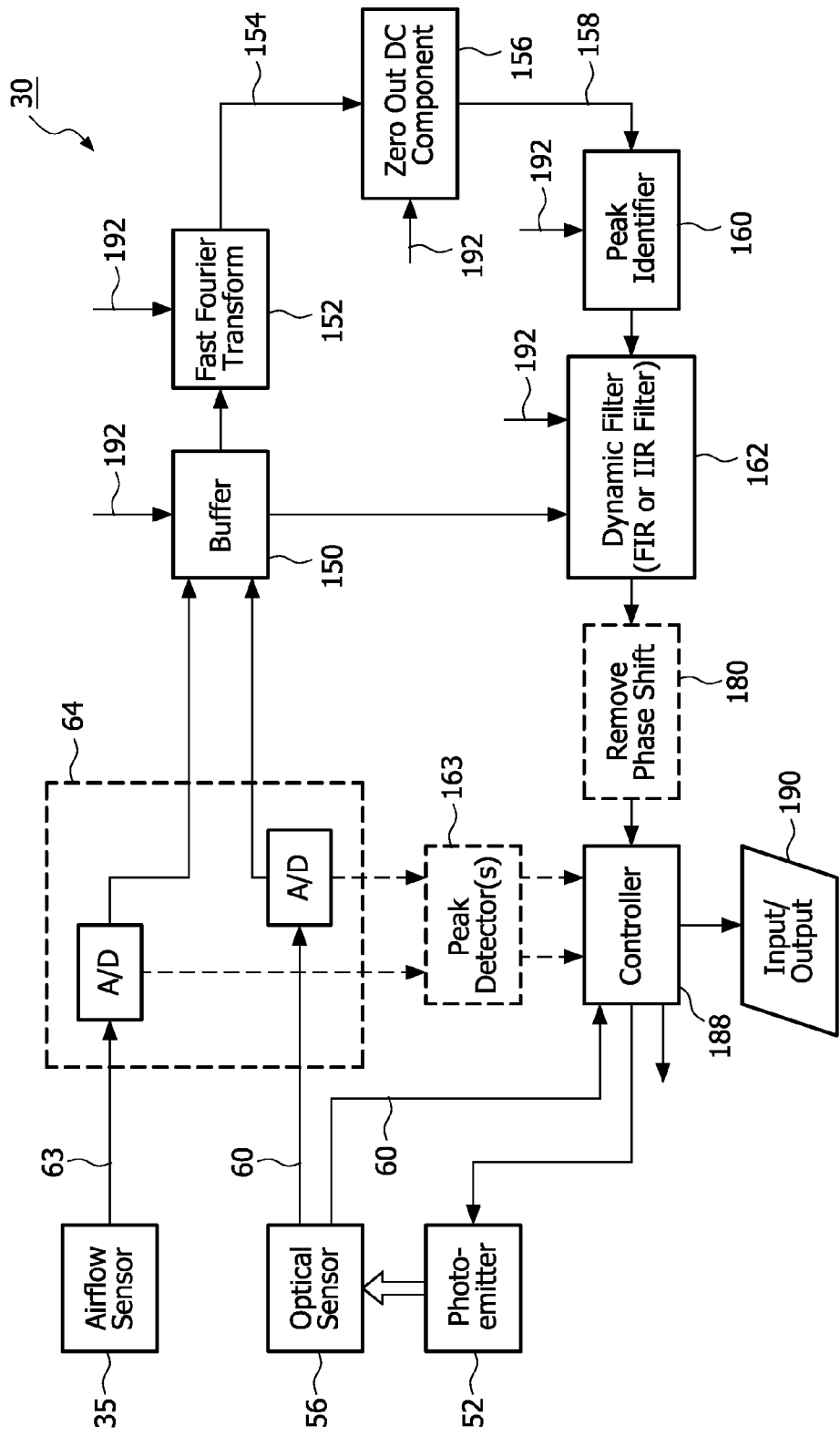
FIG. 9 is a schematic diagram illustrating an exemplary embodiment of the extra-thoracic monitoring system according to the principles of the present invention.
Figure 11:
FIG. 11 is a graph of a respiratory component contained in the raw plethysmograph signal of FIG. 10.

FIG. 9 is a schematic diagram of an exemplary embodiment of the extra-thoracic monitoring system 30 according to the principles of the present invention. Signals 60 from photodetector 56 are provided to an A/D converter, which is equivalent to interface module 64 of FIG. 3. FIG. 10 illustrates a raw hypothetical plethysmograph signal 60 detected by the photodetector, which forms the plethysmograph monitoring portion of the extra-thoracic monitoring system and is equivalent to $SpO_2$ module 68 and patient interface 42 of FIG. 3. A respiratory sensor 35 monitors a characteristic of the patient indicative of respiration, such as airflow, and provides a respiratory signal 63 indicative thereof. FIG. 11 is a graph of respiratory signal 63, which is also a component of the raw plethysmograph signal of FIG. 10.

Figure 12A:
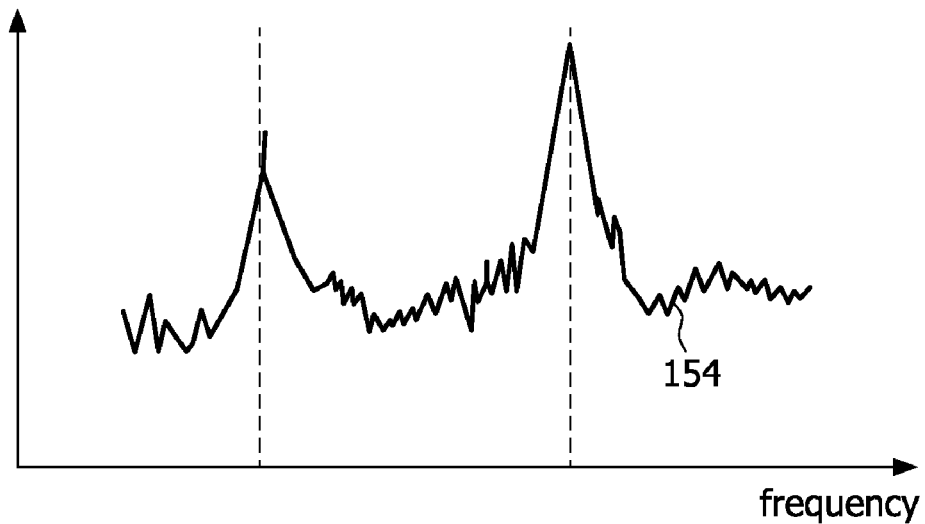
FIGS. 12A and 12B are graphs illustrating an exemplary Fourier transform of the signal of FIG. 10.
Figure 12B:
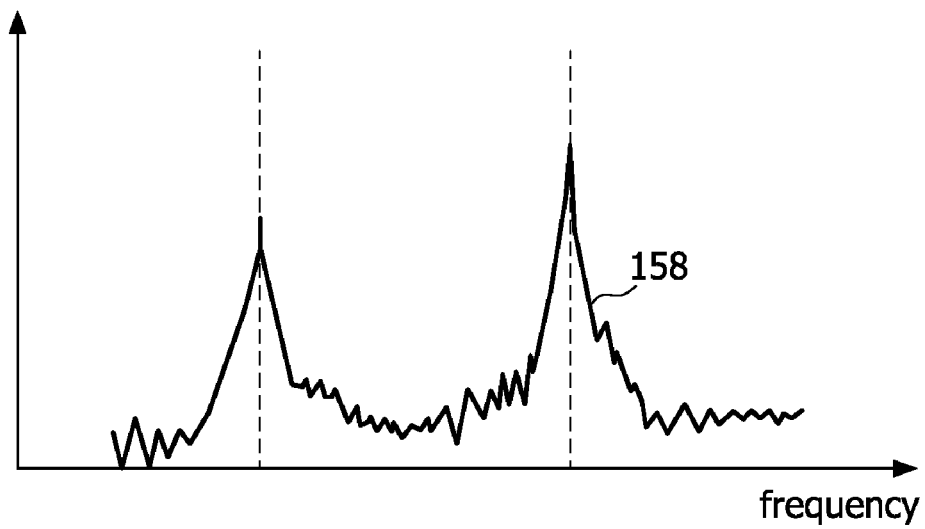

The signal from the $SpO_2$ module and the pressure card (airflow sensor 35) are provided to buffer 150 for use by the main computer and in subsequent processing steps. The plethysmograph signal 60 is provided to a Fast Fourier Transform operator 152. An example of the resulting output frequency spectrum signal 154 from Fast Fourier Transform operator 152 is shown in FIG. 12A. If necessary, an offset is removed by a zero out DC component module 156 to produce a frequency spectrum signal 158 without any DC bias. See FIG. 12B.

The peaks of the frequency spectrum signal 158 are detected by peak detector 160. Detecting the peaks is necessary to select the proper filtering frequencies to be applied to plethysmograph signal 60 in dynamic filter 162.

The present invention contemplates that the Cardiac Δd or the Thoracic Δd can be monitored using the extra-thoracic monitoring system of the present invention. The determination of which one of these variables (or both) is to be monitored is based on the filtering applied to the plethysmograph signal by dynamic filter 162.

Determining the vessel distention due to respiration ($NIVD_{Thoracic}$) involves isolating the respiratory rate frequency component ($f_{RR}$) from the frequency components of frequency spectrum signal 158, which is accomplish by dynamic filter 162. The plethysmograph signal 60 is then filtered so as to isolate the respiratory rate frequency component $f_{RR}$, thereby producing a vessel distention signal which is a surrogate for an intra-thoracic pressure measurement.

Figure 13A:
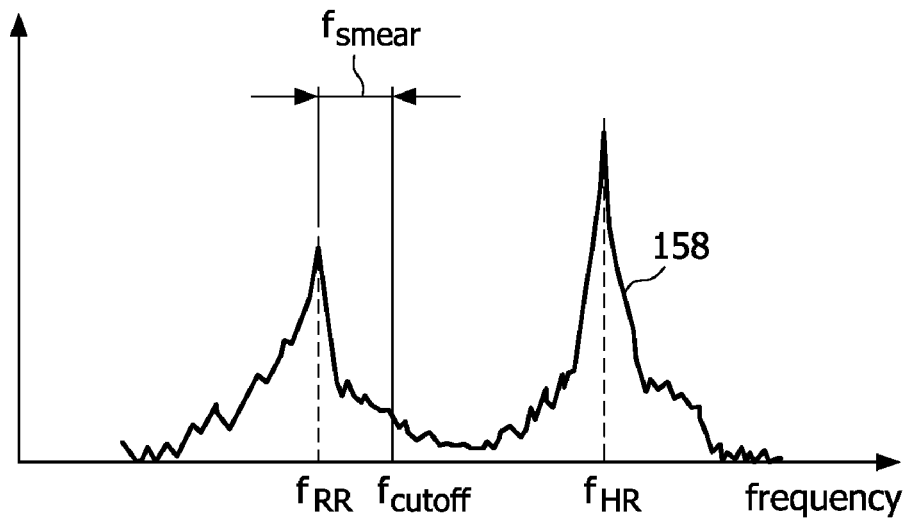
FIGS. 13A and 13B are graphs illustrating an exemplary Fast Fourier Transform (FFT) of the signal of FIG. 10 showing the selection of cutoff frequencies used in processing the plethysmograph signals according to the principles of the present invention.
Figure 13B:
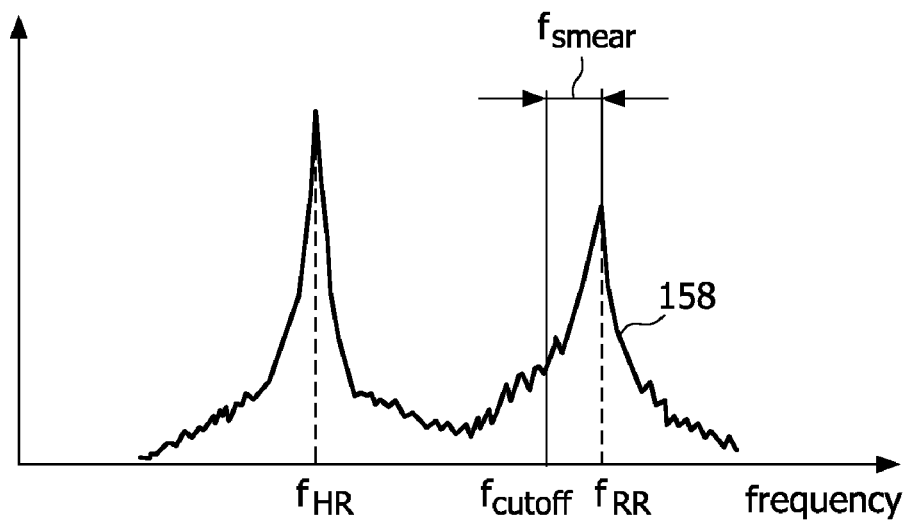

In one embodiment of the present invention, the peak in the frequency spectrum signal 158 corresponding to the breathing rate is detected based on the monitored respiratory rate from sensor 35, which is determined, at least in part by peak detector 163. Once the respiratory rate frequency component $f_{RR}$ is identified, a cutoff frequency $f_{cutoff}$ is determined. See FIG. 13A. In this embodiment, if the respiratory rate frequency component $f_{RR}$ is less than the heart rate frequency component $f_{HR}$, the dynamic filter sets the cutoff frequency ($f_{cutoff}$) as $f_{RR}+f_{smear}$. Filter 162 then low pass filters plethysmograph signal 60 at the cutoff frequency $f_{cutoff}$. If the respiratory rate frequency component $f_{RR}$ is deemed to be greater than the heart rate frequency component $f_{HR}$, the dynamic filter sets the cutoff frequency ($f_{cutoff}$) as $f_{RR}-f_{smear}$. See FIG. 13B. Filter 162 then high pass filters plethysmograph signal 60 at the cutoff frequency $f_{cutoff}$. In this embodiment, $f_{smear}$ is a predetermined threshold frequency.

In another embodiment of the present invention, the peak in the frequency spectrum signal 158 corresponding to the heart rate is detected using conventional techniques, such as that used in pulse oximetry or in EKG monitoring. This is determined, at least in part, by peak detector 163. Of course, other techniques for detecting heart rate can be used. Once the heart rate frequency component $f_{HR}$ is identified, a cutoff frequency $f_{cutoff}$ is determined in a manner similar to that discussed above. More specifically, if the respiratory rate frequency component $f_{RR}$ is less than the heart rate frequency component $f_{HR}$, the dynamic filter sets a cutoff frequency ($f_{cutoff}$) as $f_{HR}-f_{smear}$. Filter 162 then low pass filters plethysmograph signal 60 at the cutoff frequency $f_{cutoff}$. If the respiratory rate frequency component $f_{RR}$ is greater than the heart rate frequency component $f_{HR}$, and sets the cutoff frequency ($f_{cutoff}$) as $f_{RR}+f_{smear}$. The filter then high pass filters plethysmograph signal 60 at the cutoff frequency $f_{cutoff}$. In this embodiment, $f_{smear}$ is a predetermined threshold frequency.

The present invention also contemplates that the size of $f_{smear}$ can be adjusted. An example of this is discussed below. In any event, whether or not $f_{smear}$ is adjustable or fixed, $f_{smear}$ should be large enough to ensure that sidelobes contributing to the main peak in the frequency band of interest are captured, so that adequate filtering is performed.

Determining the vessel distention due to cardiac function ($NIVD_{Cardiac}$) involves isolating the heart rate frequency component ($f_{HR}$) from the frequency components of frequency spectrum signal 158, using a process similar to that discussed above. As with the previous embodiment, the cutoff frequency can be determined from the respiratory rate frequency component $f_{RR}$ or from the heart rate frequency component $f_{HR}$.

If the respiratory rate frequency component $f_{RR}$ is known, and if the respiratory rate frequency component $f_{RR}$ is less than the heart rate frequency component $f_{HR}$, the dynamic filter sets the cutoff frequency ($f_{cutoff}$) as $f_{RR}+f_{smear}$, thereby isolating the heart rate frequency component $f_{HR}$. Filter 162 then high pass filters plethysmograph signal 60 at the cutoff frequency $f_{cutoff}$. If the respiratory rate frequency component $f_{RR}$ is deemed to be greater than the heart rate frequency component $f_{HR}$, dynamic filter 162 sets the cutoff frequency ($f_{cutoff}$) as $f_{RR}-f_{smear}$. See FIG. 13B. Filter 162 then low pass filters plethysmograph signal 60 at the cutoff frequency $f_{cutoff}$. In this embodiment, $f_{smear}$ is a predetermined threshold frequency.

If the heart rate frequency component $f_{HR}$ is known, and if the respiratory rate frequency component $f_{RR}$ is less than the heart rate frequency component $f_{HR}$, the dynamic filter sets the cutoff frequency ($f_{cutoff}$) as $f_{HR}-f_{smear}$, thereby isolating the heart rate frequency component $f_{HR}$. Filter 162 then high pass filters plethysmograph signal 60 at the cutoff frequency $f_{cutoff}$. If the respiratory rate frequency component $f_{RR}$ is deemed to be greater than the heart rate frequency component $f_{HR}$, dynamic filter 162 sets the cutoff frequency ($f_{cutoff}$) as $f_{HR}+f_{smear}$. See FIG. 13B. Filter 162 then low pass filters plethysmograph signal 60 at the cutoff frequency $f_{cutoff}$. In this embodiment, $f_{smear}$ is a predetermined threshold frequency.

The present invention also contemplates using a band-pass filter centered on the frequency component of interest to isolate that component from the frequency spectrum signal. For example, if the respiratory rate frequency component $f_{RR}$ is known and the $NIVD_{Thoracic}$ is being monitored, an upper cutoff frequency for the band pass filter can be set as $f_{RR}+f_{smear}$ and a lower cutoff frequency for the band pass filter can be set as $f_{RR}-f_{smear}$. Filter 162 then band pass filters plethysmograph signal 60 at these upper and lower cutoff frequencies. If the heart rate frequency component $f_{HR}$ is known and the $NIVD_{Cardiac}$ is being monitored, an upper cutoff frequency for the band pass filter can be set as $f_{HR}+f_{smear}$ and a lower cutoff frequency for the band pass filter can be set as $f_{HR}-f_{smear}$. Filter 162 then band pass filters plethysmograph signal 60 at these upper and lower cutoff frequencies.

The present invention contemplates that the cutoff frequency is recalculated for each breath, thereby providing a very fast response to any changes in the patient, which provides a more accurate measurement of $NIVD_{Thoracic}$ or $NIVD_{Cardiac}$. Of course, the cutoffs can also be calculated less frequently or the frequency by which the cutoffs are recalculated can be determined based on the monitored condition of the patient, thereby maximizing system efficiency. For example, if the patient is relatively stable, the cutoffs can be recalculated less frequently than when the patient is not.

Figure 14:
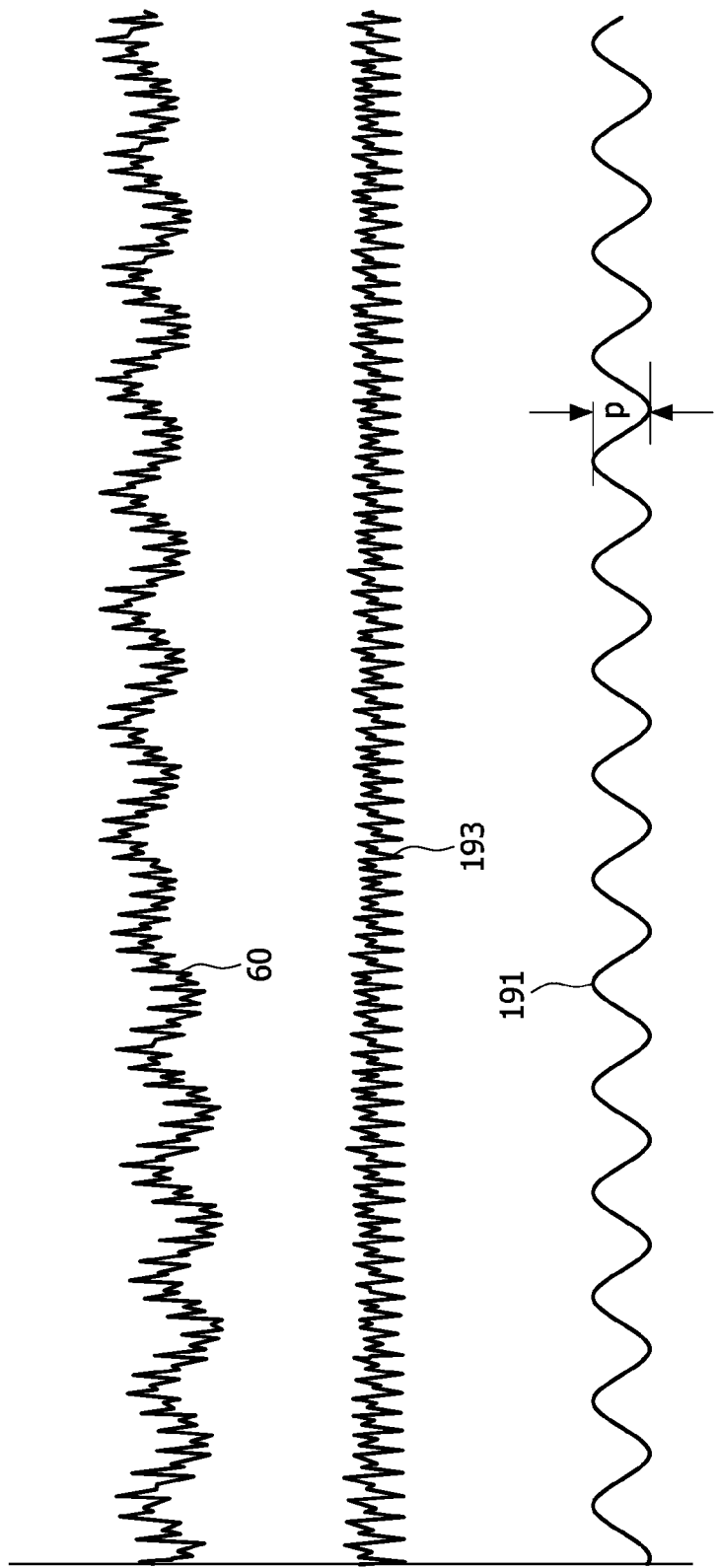
FIG. 14 is a graph illustrating a raw NIVD waveform, an $NIVD_{Thoracic}$ waveform, and an $NIVD_{Cardiac}$ waveform.

An example of the $NIVD_{Thoracic}$ output waveform 191 and $NIVD_{Cardiac}$ output waveform 193 produced by the present invention is shown in FIG. 14. This figure also shows a total or raw NIVD signal 60. The output of dynamic filter 162 ($NIUVD_{Thoracic}$ signal 191 and/or $NIVD_{Cardiac}$ signal 193), which is the filtered plethysmograph signal, can be used in a variety of ways. For example, the present invention contemplates removing any phase shifts, if desired, via a phase shift removal component 180. The signals can be displayed, transmitted, stored, or operated upon in any manner by controller 188 and input/output device 190. It should be noted that the present invention contemplates that each component 150-180 operates under the control of controller 188. Arrows 192 signify this aspect of the invention.

It can be appreciated that other physiological characteristics that manifest themselves as a pressure or volume change in the patient's arterial circulatory system can be monitored by the extra-thoracic monitoring system of the present invention. This is accomplished by setting the frequency cutoff to select or isolate the frequencies associated with these characteristics in the frequency spectrum signal. For example, Burton's Waves or Traub-Herring Waves, which are relatively slow changes in the patient's circulatory pressure or volume, can be detected by selecting the frequency cutoff to remove the higher frequency signals, such as breathing and heart rate.

The two primary parameters for calculating blood flow from the heart are stroke volume and heart rate. Because blood flow equals stroke volume times the heart rate, the flow changes as a result of altering stroke volume, heart rate, or both. In order to assess the change in blood flow, the present invention contemplates plotting the heart rate and pathlength changes that occur for each heartbeat within each breath.

IV. PHYSIOLOGICAL ROLL-OFF

Figure 15:
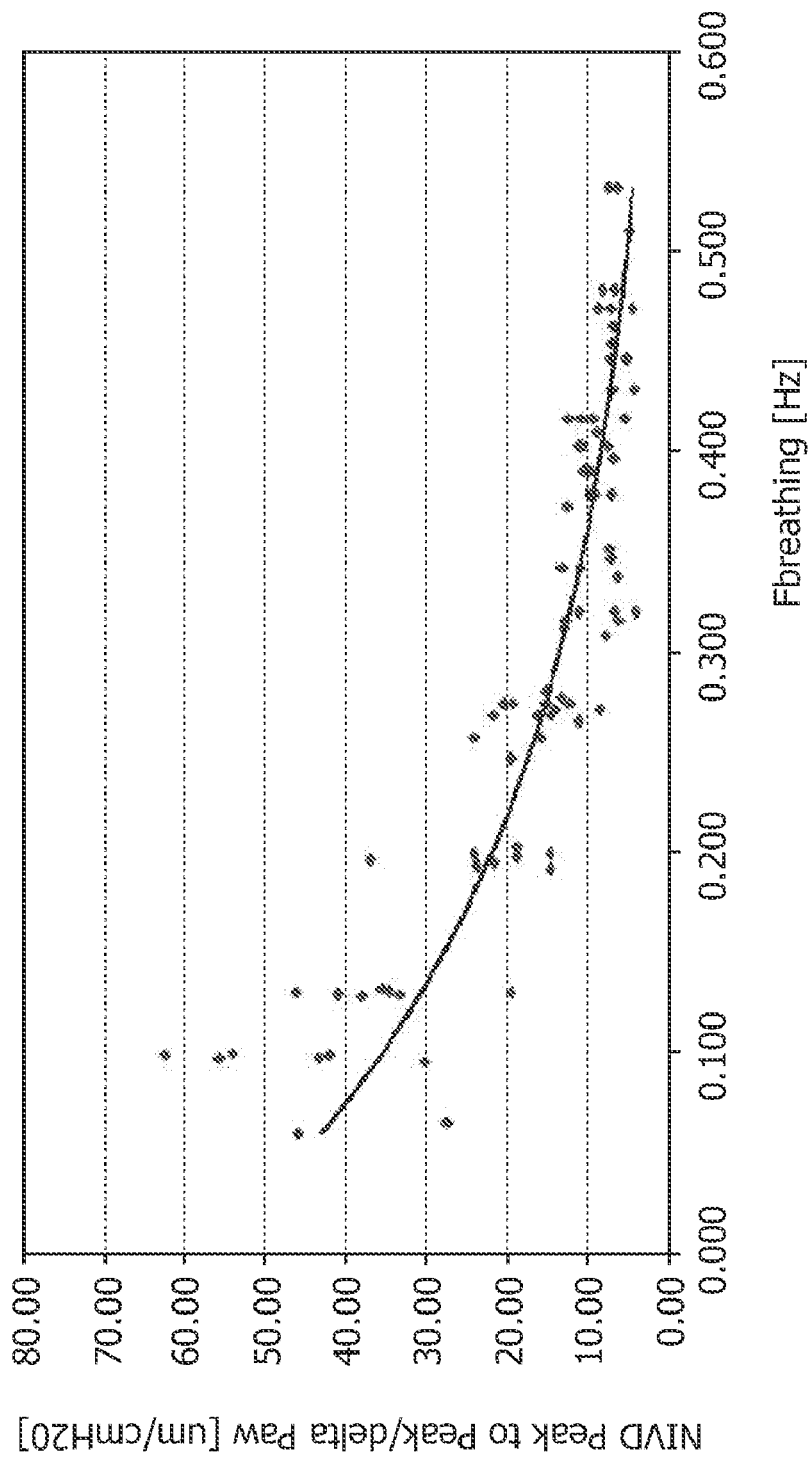
FIG. 15 is a graph showing a relationship between the raw NIVD signal peak-to-peak values and breathing frequency.
Figure 16:
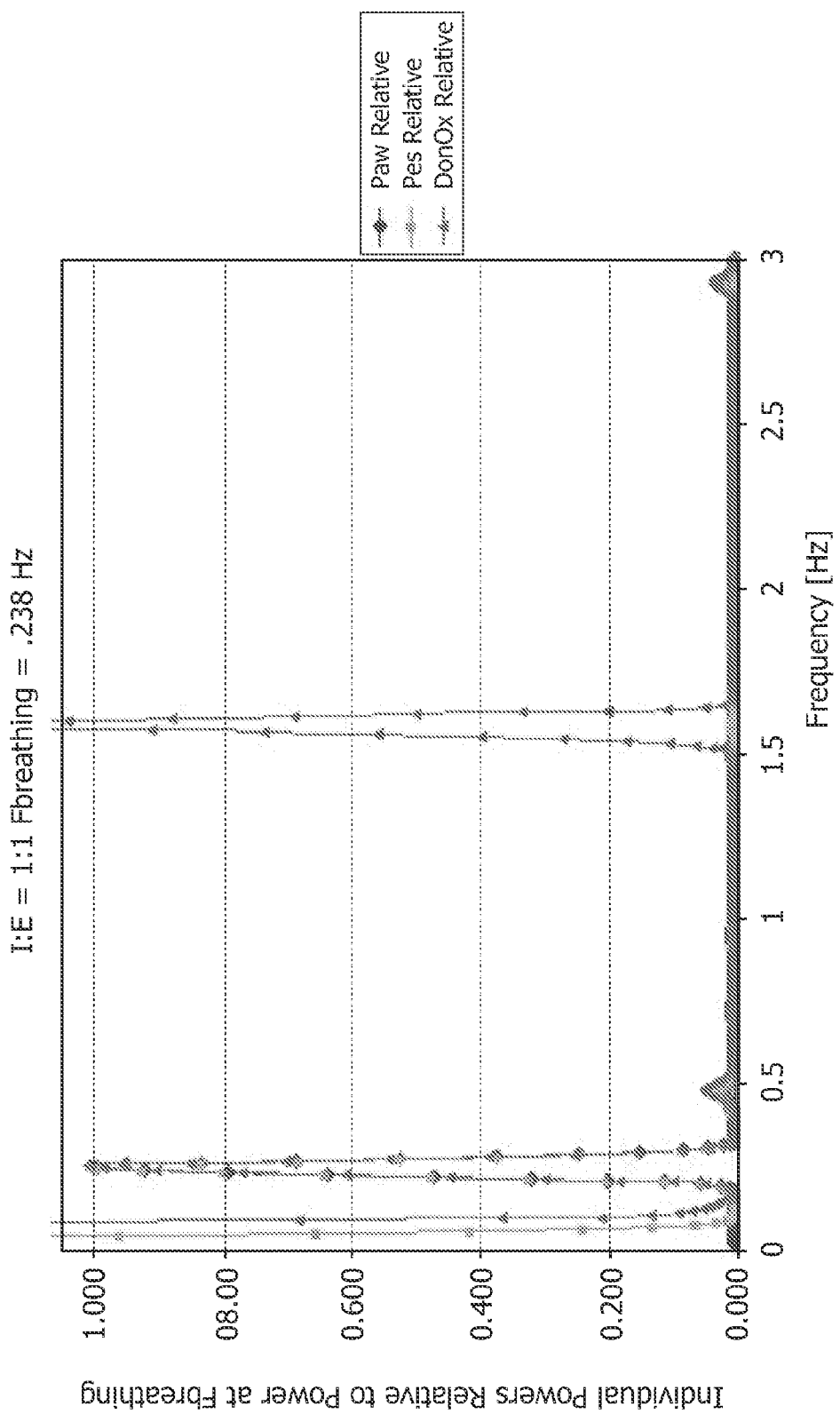
FIGS. 16-19 are graphs showing an impact of a patient's inspiratory-to-expiratory ratio on the FFT frequency spectrum signal.

The inventors became aware that the raw NIVD signal, as well as the $NIVD_{Thoracic}$ or $NIVD_{Cardiac}$ signal, are attenuated as the patient's breathing frequency increases. The "roll-off" of the raw NIVD signal's peak-to-peak values as the breathing frequency increases is shown by line 159 in FIG. 15. Line 159 is a trend line for the peak-to-peak NIVD measurements taken over a range of breathing rates. The present invention contemplates using this roll-off to correct or compensate for the raw NIVD signal (Δd), $NIVD_{Thoracic}$ (Cardiac Δd), $NIVD_{cardiac}$, (Thoracic Δd) signals, or any combination thereof based on the monitored breathing rate. For example, once an NIVD value is determined, the patient's breathing frequency at that time is also determined from respiratory sensor 35. The NIVD peak-to-peak value can then be corrected based on the known $NIVD_{(peak\ to\ peak)}$ versus breathing frequency relationship F. This correction can be done using any conventional signal processing technique. For example, a look-up table can be generated and used to provide a breathing frequency correction factor or an equation can be determined that represents the relationship between a measured NIVD value and breath rate. Such an equation would correspond, in general, to line 159.

It should also be noted that the resistance (R) and compliance (C) of the circulatory system (from the thorax to the location of the plethysmography sensor) can be determined empirically, for example through the testing of a number of patients, or can be estimated using standard indices, such as pulse transit time. If R and C are known, the NIVD versus breathing frequency relationship can be determined beforehand and used to correct the NIVD value for the measured breathing frequency.

V. INSPIRATORY TO EXPIRATORY RATIO

Figure 19:
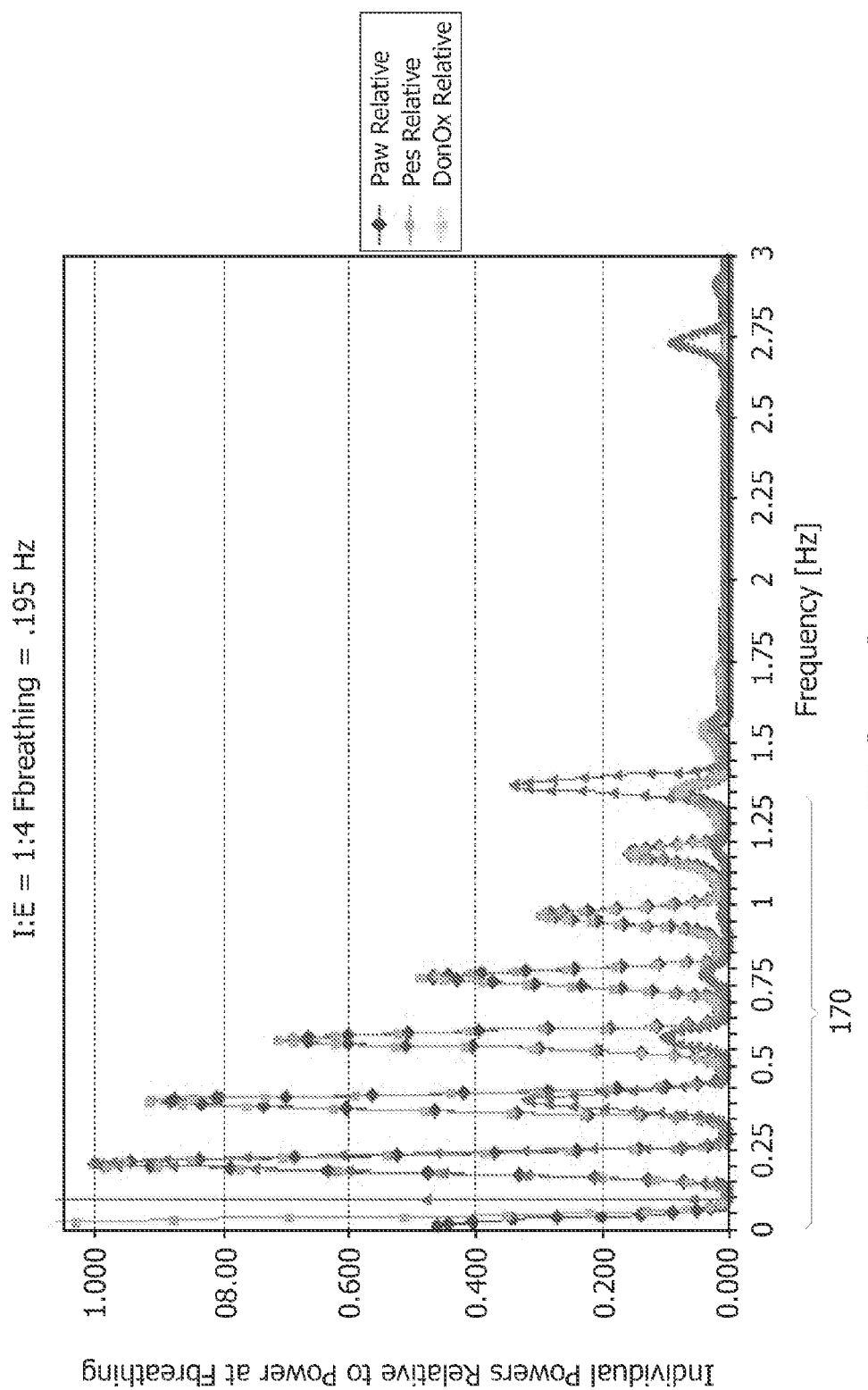

The inventors also became aware that a patient's inspiratory-to-expiratory (I:E) ratio impacts frequency spectrum signal 158. Namely, the present inventors determined that a decrease in the I:E ratio introduces additional harmonics in the frequency spectrum signal produced by the FFT. This phenomena is shown in FIGS. 16-19. These figures illustrate the additional harmonic frequencies, generally indicated at 170, that appear in the frequency spectrum signal as the I:E ratio goes from 1:1 (FIG. 16) to 1:4 (FIG. 19). It should be noted that certain patient populations have an I:E ratios that deviate from a 1:1 ratio. In fact, the I:E ratio for a normal individual is in the range of 1:2-1:3. However, for some people, such as patients with asthma, Pickwickian syndrome, congestive heart failure, pulmonary fibrosis, pneumonia or experiencing a drug overdose, the I:E ratio has been determined to have an I:E ratio much less than 1:1.

Knowing that harmonics in the frequency spectrum signal near the breathing frequency $f_{RR}$ are created as the I:E ratio deviates from 1:1, the present invention contemplates accounting for these additional harmonics in setting the cut-off frequency. For example, in determining Thoracic Δd ($NIVD_{Thoracic}$) using $f_{RR}$ as the base point, the value for $f_{smear}$ can be increased as the I:E deviation from 1:1 decreases, assuming that $f_{RR} < f_{HR}$. Using $f_{HR}$ as the base point, the value for $f_{smear}$ can be decreased as the I:E deviation from 1:1 decreases, again assuming that $f_{RR} < f_{HR}$.

VI. INTRA-BREATH CHANGES IN HEART RATE

Blood is delivered from the heart to the systemic circulation in pulses. The average amount of blood flow leaving the heart within each cardiac cycle is known as cardiac output. Cardiac output is the product of the volume of blood leaving the heart with each ejection portion of the cardiac cycle and the rate at which the heart is beating. This relationship can be summarized as follows:

Total Average Blood Flow=Cardiac Output (mL/min)=Heart Rate (beats/min)×Stroke Volume (mL/beat).

Similarly, the average blood flow to an appendage, such as a finger, is the product of the volume of blood delivered to the appendage within each cardiac cycle (a.k.a. pulse volume) and the rate at which it is delivered (pulse rate). This relationship can be summarized as follows:

Average Blood Flow to Appendage (mL/min)=Pulse Rate (beats/min)×Pulse Volume (mL/beat).

As described above, a change in vessel distention arises due to a change in blood flow. The extra-thoracic monitoring system of the present invention provides the ability to illustrate changes in vessel distention of an appendage, such as a finger. Arterial vessel distention happens during each heart cycle and each breath cycle. The average change in distention that occurs throughout each breath is the result of the average vessel distention that happens during each of the heart beats that take place within the each breath. Because the average blood flow to an appendage is a product of the average pulsed volume of blood delivered and the pulse rate, the extra-thoracic monitoring system provides the ability to view and plot changes in pulse rate in addition to changes in distention.

Figure 20:
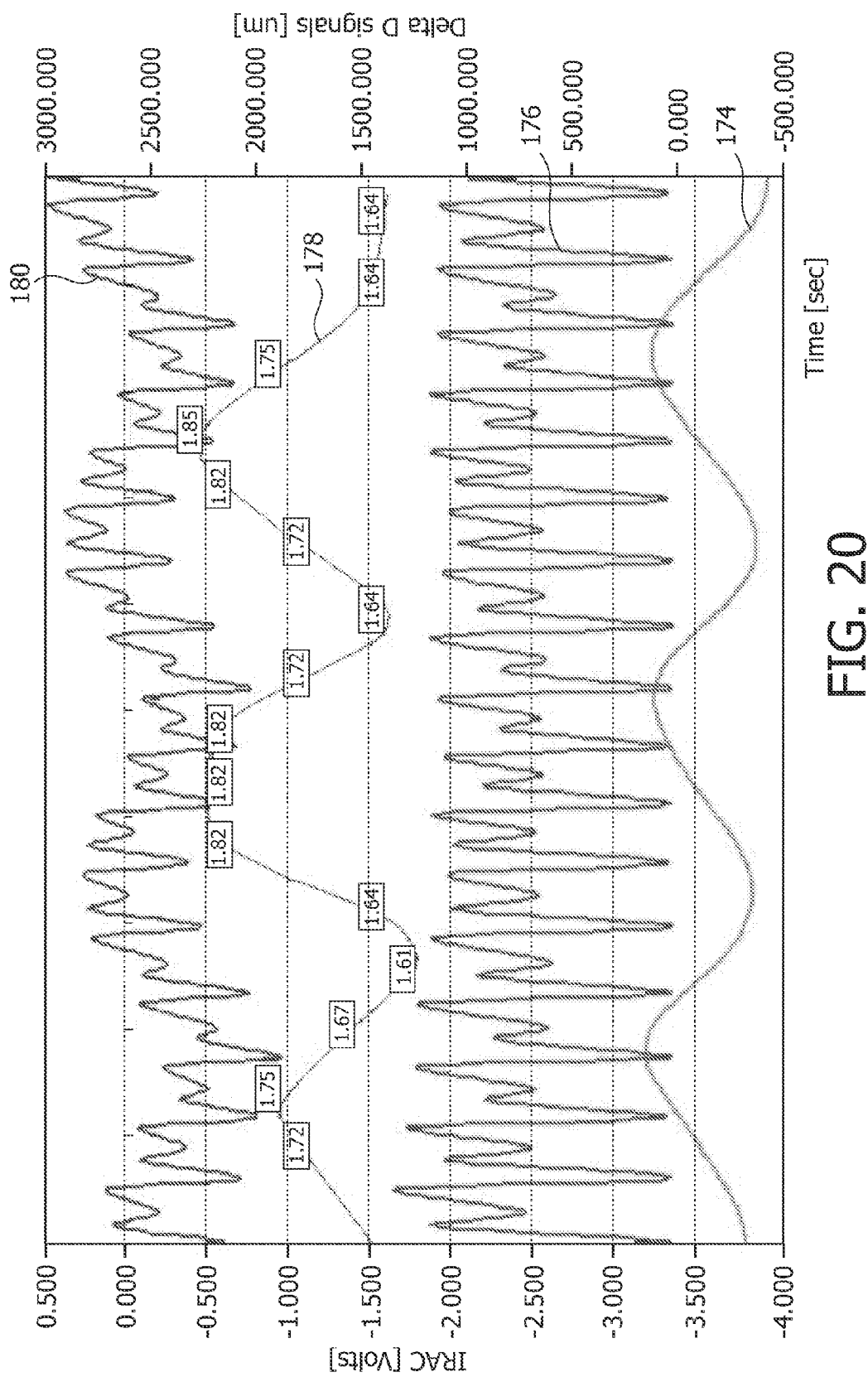
FIG. 20 is a graph illustrating intra-breath pulse rate variations.

FIG. 20 depicts the extra thoracic monitoring system's ability to display the mean change in distention that occurs within each breath (waveform 174), as well as the changes in distention that occur within each cardiac cycle (waveform 176) and the change in cardiac cycle rate (waveform 178). Waveform 180 in FIG. 20 illustrates the raw NIVD (Δd) signal, which includes both the Cardiac Δd and Thoracic Δd components, and, thus, represents a total NIVD waveform. As can be seen in this illustration, in this patient, for example, the distention that occurs during each cardiac cycle remains relatively the same throughout the three breaths. However, the heart rate varies quite a bit. During the first breath, the heart rate varies from 1.61 to 1.75 Hz (approximately 8.4 beats/min variation). During the second breath, the heart rate varies by approximately 10.8 beats/min, and, during the third breath, the heart rate varies by approximately 12.6 beats/min.

VII. FURTHER PROCESSING

As shown in FIG. 14, if the mean vessel distention of the arterial vessels that occurs due to each heartbeat is plotted over the course of at least one breath, the peak minus the valley of that mean (distance P) is a reflection of the pleural pressure change that occurred for the given breath(s). The present invention contemplates producing waveform 191 from the raw NIVD signal 60 using the signal processing techniques discussed above. An alternative embodiment of the present invention also contemplates producing waveform 191 by passing total or raw NIVD signal 60 through a low pass filter. Any conventional peak-to-peak detection technique can be used to determine distance P.

Another method of finding the mean vessel distention is to read a large number of samples of total signal 60 into an array. Then, the FFT is used to determine the heart rate. Once the heart rate is know, the present invention contemplates dividing the number of samples in the array by the heart rate to create sub-arrays. Each resulting sub-array holds one period's worth of heart beats. Next, simply determine the mean for each sub-array and then plot the mean of each sub array. The plot will produce a waveform similar to that of signal 191. The advantage that such a digital filter offers over finding the mean for each heartbeat is improved resolution. Finding the mean for each heartbeat will only produce one point per heartbeat, whereas the digital filter will produce many.

The present inventor also recognized that the NIVD signals may include an undesirable amount of noise. To account for this noise, the present invention contemplates rejecting the NIVD signal for a particular breath based on the signal to noise ratio (SNR) for the NIVD signal for that breath.

Figure 21:
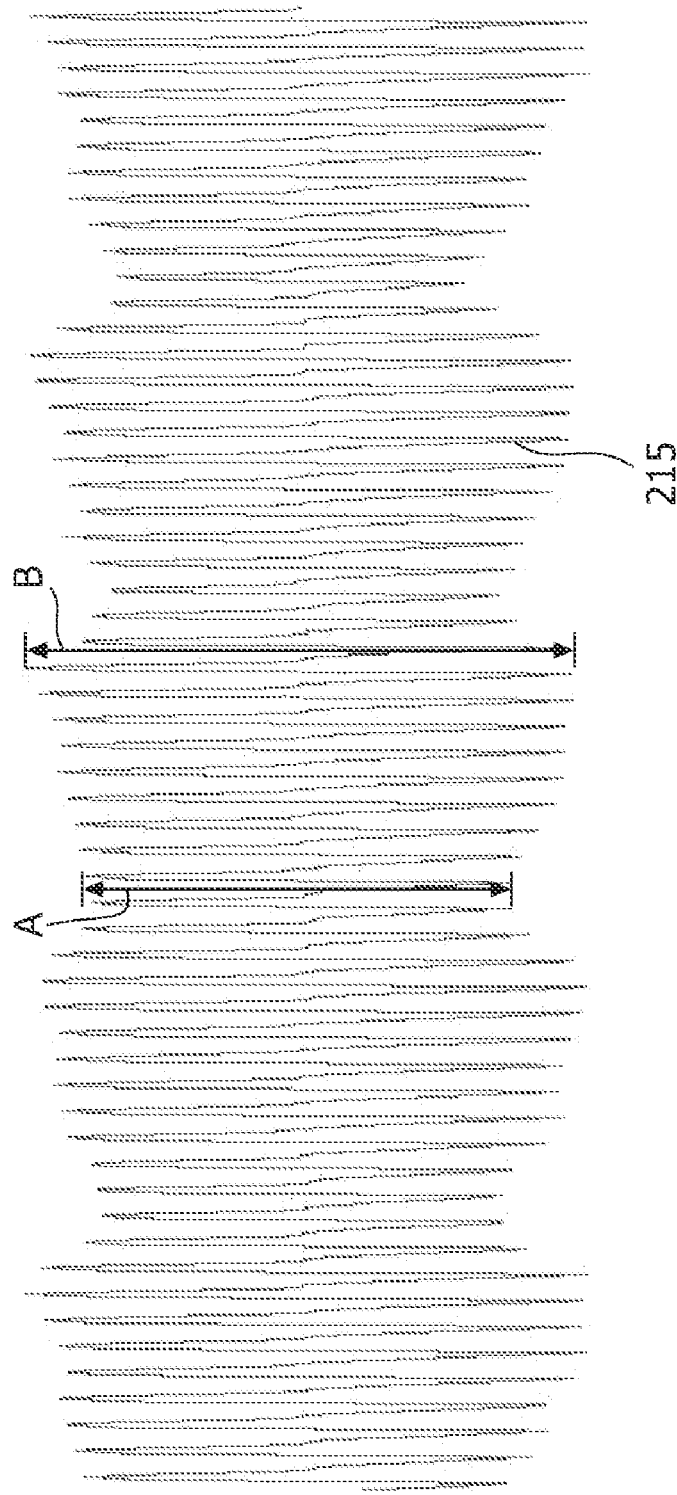
FIG. 21 is a graph illustrating a technique for determining the pulsus paradoxis of a patient using the extra-thoracic monitoring system of the present invention.

FIG. 21 illustrates a technique by which the present invention determines a patient's pulsus paradoxis, which is the change in the envelope of the pulse pressure (Cardiac Δd) throughout one breath. This figures shows a raw NIVD (Δd) signal 215 produced by the extra-thoracic monitoring system of the present invention over a plurality of breathings. As shown by arrows A and B, the percent change in the pulse pressure (Cardiac Δd) over one respiratory cycle can be determined. For example, this figure shows an approximately 32% change in pulse pressure over one breath. It can be appreciated that any technique for calculating the change in pulse pressure, difference between the length of arrows A and B, can be used in the system of the present invention.

VIII. OTHER FEATURES OF THE EXTRA-THORACIC MONITORING SYSTEM

A. Other Sources for the Plethysmograph Signal

In the embodiment described above, the plethysmograph signal is obtained optically via a photodetector so that the plethysmography signal is a photoplethysmography signal. It is to be understood that the present invention contemplates that other sensors can be used to monitor the changes in the patient's circulatory system due to pressure or volume changes in that system. For example, a blood pressure cuff that is deflated is capable of detecting changes in vessel distention by detecting the volume change in the vessel bed encompassed by the cuff. The pressure in the circulatory system can also be monitored directly by use of an invasive pressure sensor, such as an arterial line, disposed in the patient. In short, any sensor that is capable of monitoring a physiological characteristic of a patient associated with pressure changes in such a patient's circulatory system is suitable to provide plethysmography signal 60 used by the processing system of the present invention.

B. Fractional Concentration of Inspired Oxygen

The present invention contemplates that the extra-thoracic monitoring system can include other functionalities and features. An example of a feature that can be added to the system is the capability to measure the fractional concentration of oxygen inhaled by a patient ($FO_2$) and the fractional concentration of oxygen inhaled by a patient over one breath ($FIO_2$). This measurement technique can be used alone or in conjunction with the cardio-pulmonary monitoring system discussed above.

Figure 22:
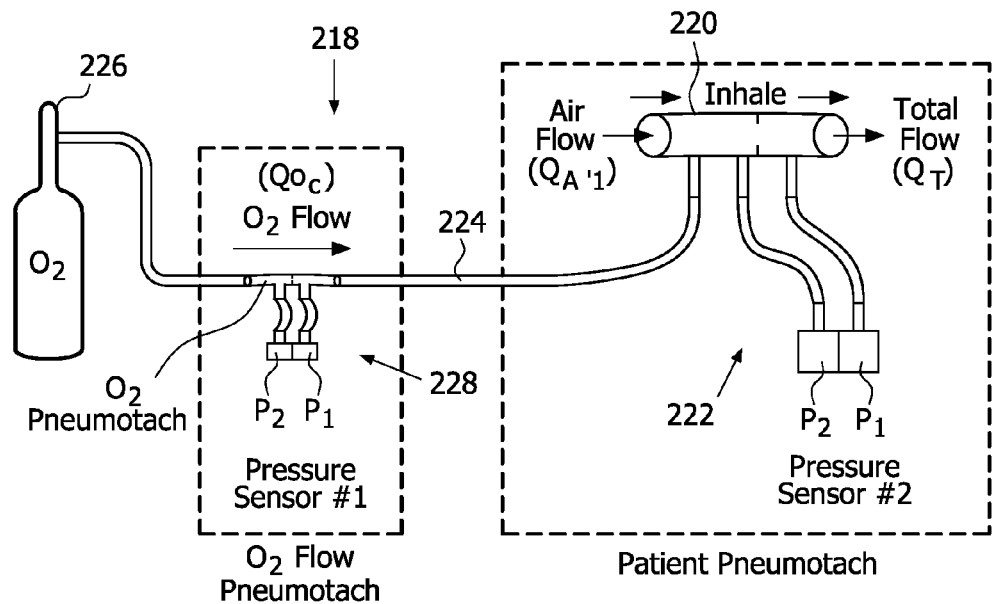
FIGS. 22 and 23 are schematic diagrams of two embodiments of systems for measuring the fractional concentration of oxygen inhaled by a patient suitable for use with the extra-thoracic monitoring system of the present invention.

As shown in FIG. 22, the $FO_2$ monitoring system 218 includes a patient circuit 220 adapted to communicate a flow of breathing gas to an airway of a patient. A first flow sensor 222 associated with the patient circuit quantitatively measures a flow of gas ($Q_T$) inhaled, exhaled, or inhaled and exhaled by a patient. The $FO_2$ monitoring system also includes an oxygen conduit 224 adapted to be coupled to an oxygen source 226 and to the patient circuit to communicate oxygen from the oxygen source to such a patient. A second flow sensor 228 associated with the oxygen conduit quantitatively measures a flow of the oxygen ($Q_{O2}$) in the oxygen conduit. In an exemplary embodiment, the pressure sensors that are used in flow sensors 222 and 228 are provided on pressure card 66 of FIG. 3. A processing system (not shown) receives the signals from the flow sensors and determines the $FO_2$ based on the output of the first flow sensor and the second flow sensor.

In one embodiment of the present invention, $FO_2$ at any given time is calculated by the processor as follows:

$$FO_2 = \frac{1.0(Q_{O2}) + 0.21(Q_T - Q_{O2})}{Q_T}.$$

This assumes that 100% oxygen is being delivered to the patient. If the oxygen concentration is less than 100%, the multiplier on $Q_{O2}$ is adjusted to that concentration.

The processor calculates a fractional concentration of oxygen inhaled by a patient over one breath cycle ($FIO_2$) as follows:

$$FIO_2 = \frac{\int_{t_1}^{t_2} (FO_2) dt}{t_2 - t_1},$$

where $t_1$ corresponds to a time at a start of an inhalation phase of a breath cycle, and $t_2$ corresponds to a time at an end of the inhalation phase.

The present invention also contemplates determining $FO_2$ as follows:

$$FO_2 = \frac{VO_2}{V_T},$$

where $VO_2$ is the volume of oxygen delivered to the patient and is determined based on an output or the first and the second sensors as follows:

$$VO_2 = \int_{t_1}^{t_2} (Q_{O2}) dt + \int_{t_1}^{t_2} (0.21(Q_T - Q_{O2})) dt,$$

where $t_1$ corresponds to a time at a start of an inhalation phase of a breath cycle, and $t_2$ corresponds to a time at an end of the inhalation phase, and where $V_T$ is the volume of gas delivered to the patient and is determined based on an output of first sensor 222 as follows:

$$V_T = \int_{t_1}^{t_2} Q_T \, dt.$$

The processor calculates a fractional concentration of oxygen inhaled by a patient over one breath cycle ($FIO_2$) as discussed above.

Figure 23:
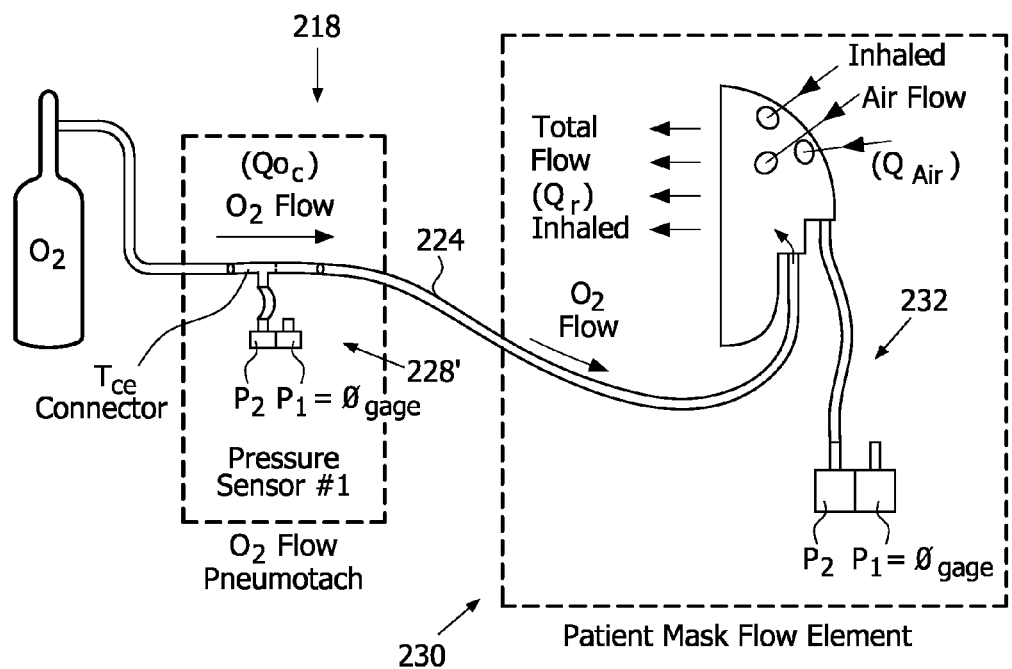

FIG. 23 illustrates an $FO_2$ monitoring system 230 that is similar in many respects to the monitoring system shown in FIG. 22. The primary differences between monitoring system 230 and monitoring system 218 lies in the technique used to measure the flow of gas ($Q_T$) inhaled, exhaled, or inhaled and exhaled by the patient. In place of the pneumotach 222 shown in FIG. 22, monitoring system 230 in FIG. 23 uses a flow sensing system 232 disclosed in U.S. Pat. Nos. 6,544,192; 6,342,040; and 6,017,315 all to Starr et al., the contents of each of which are incorporated herein by reference, to measure the flow of gas inhaled and exhaled by the patient. In the embodiment, flow sensing system 232 measures the inhaled and exhaled air flow $Q_{air}$ rather than $Q_T$. Thus calculating $FO_2$ is rewritten as:

$$FO_2 = \frac{1.0(Q_{O2}) + 0.21(Q_{air})}{Q_T}.$$

The $FIO_2$ is calculated as discussed above based on the measured $FO_2$.

C. Shunt Index Active Nomogram

Another example of a feature that can be added to the extra-thoracic monitoring system is a system for displaying a nomograph that is used to estimate the percentage of a patient's shunt, also referred to as the shunt index. This display and estimation technique is used with the $FIO_2$ measurement discussed above and the $SpO_2$ measurement that is obtained from the photoplethysmography signal.

Figure 24:
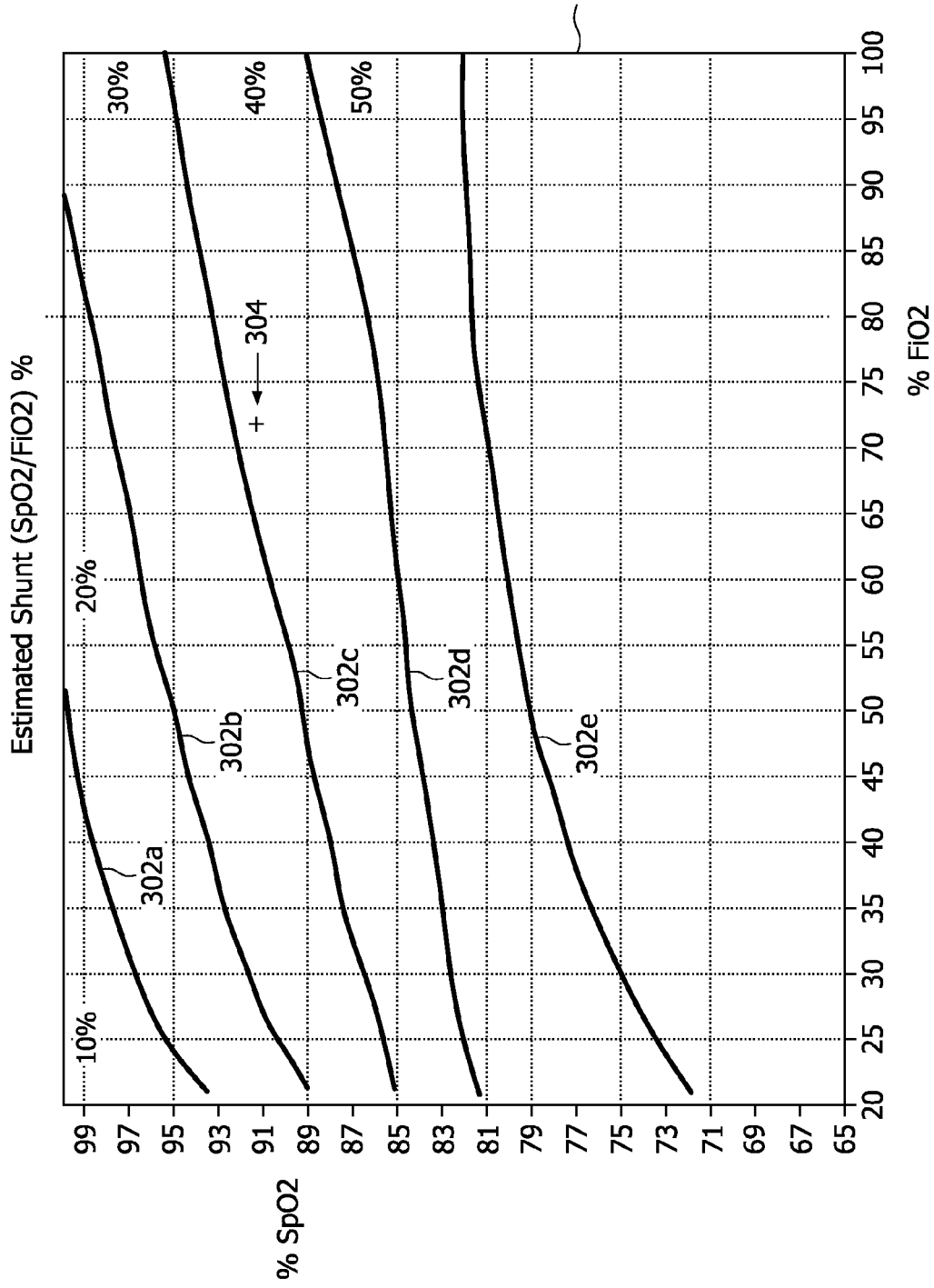
FIG. 24 illustrates an exemplary nomograph display according to the principles of the present invention.

FIG. 24 illustrates an exemplary display 300 that can be shown, for example, on display area 44 of monitoring system 30. A display controller, such as the processor or the main computer shown in FIG. 1 or 3, controls the display such that the display shows, in a first field on the display area, a nomogram illustrating a relationship between the measured $SpO_2$, the $FIO_2$, and an estimated shunt. More specifically, the nomogram shows the $SpO_2$ on a first axis, the $FIO_2$ on a second axis, and a plurality of curves 302a-302e such that each curve corresponds to a common estimated shunt percentage.

This is an "active" nomogram in that the display controller causes an indicator 304 to be displayed on the nomogram at a location defined by coordinates corresponding to a current value of the $SpO_2$ and the $FIO_2$. That is, once the $SpO_2$ and the $FIO_2$ are determined, indicator 304 is placed at the coordinates corresponding to these $SpO_2$ and the $FIO_2$ values. This enables the user to quickly visualize which shunt index curve the indicator is close to, thereby providing the user with an estimation of the patient's shunt. The present invention further contemplates that the position of the indicator on the nomogram is continuously updated each time a new value for the $SpO_2$ or the $FIO_2$ is determined. As a further feature, the processor can calculate the estimated shunt based on the $SpO_2$ and the $FIO_2$ measurement, and the calculated estimated shunt can be displayed as a numerical value in a second field on the display area.

The present invention also contemplates showing one or more past indicators on the nomogram along with the current indicator. The past indicator(s) is displayed in the nomogram at a location defined by coordinates of prior values for the $SpO_2$ and the $FIO_2$. This enables the user to see how the patient's condition, $SpO_2$, $FIO_2$, and shunt index has changed over time.

D. Device Screen Shots

FIGS. 25-33 are screen shots of a display in a user interface for use with the extra-thoracic monitoring system of the present invention. These screens are displayed, for example, on display area 44 of monitoring system 30.

Figure 25:
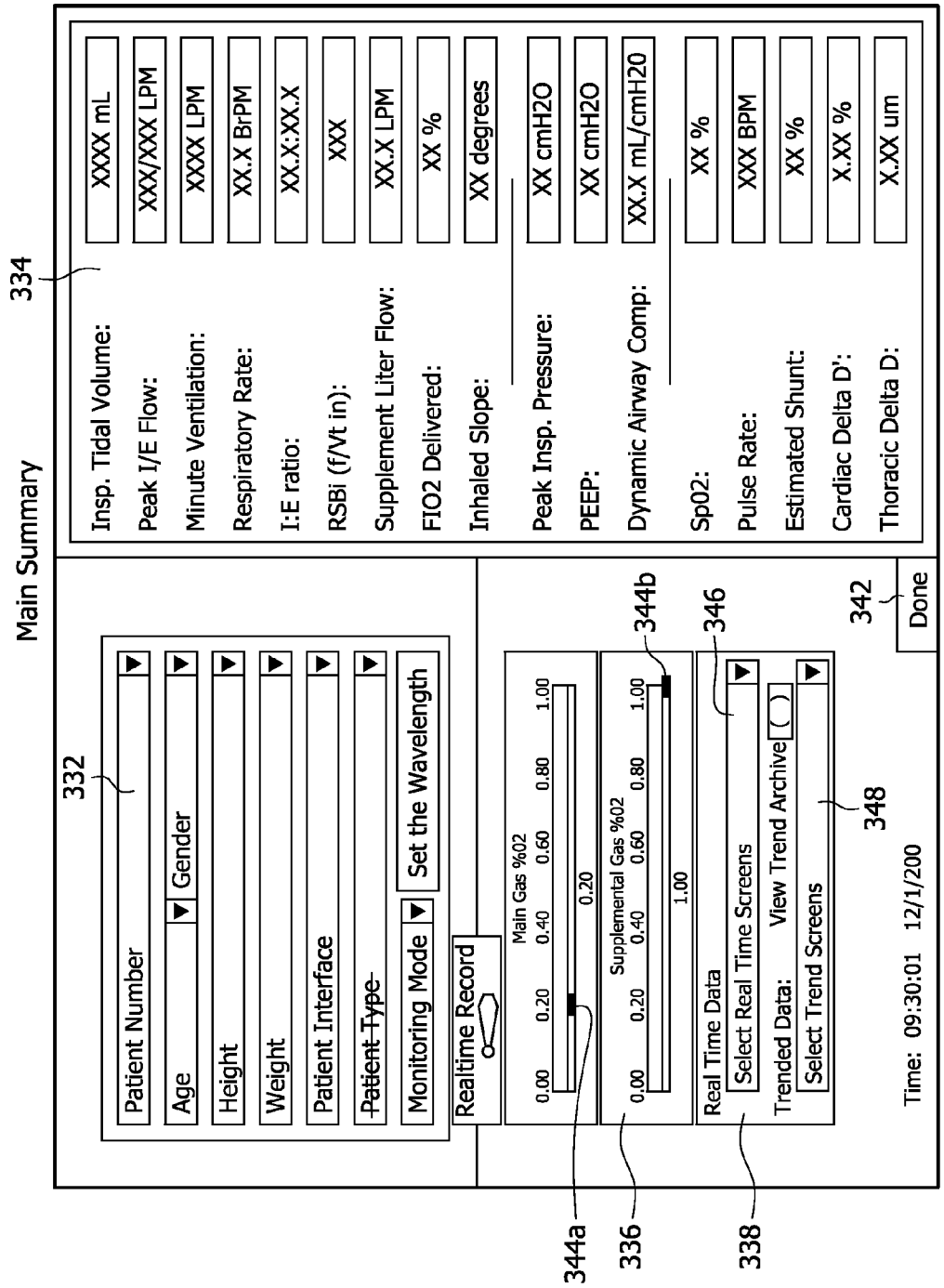
Figure 26:
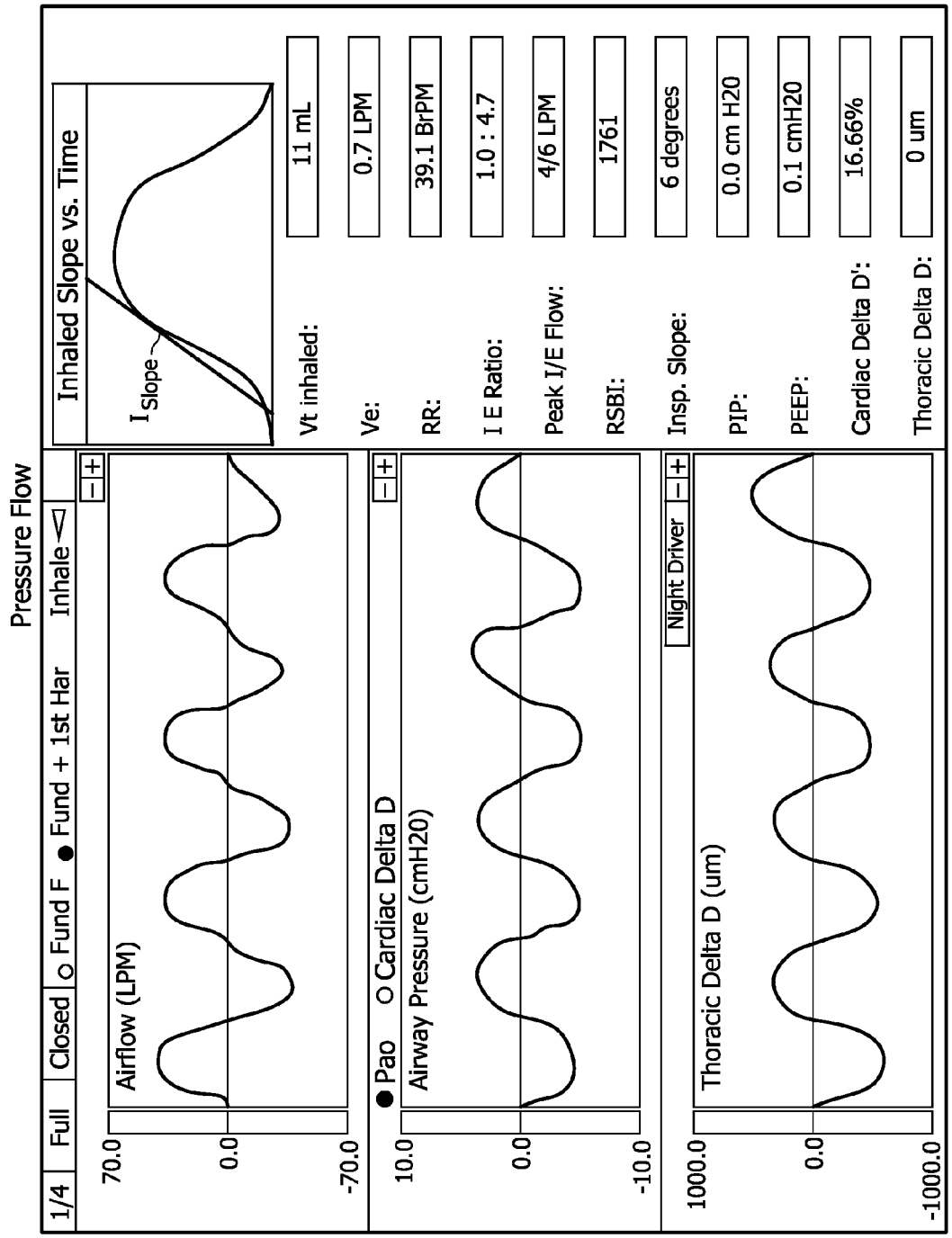
Figure 27:
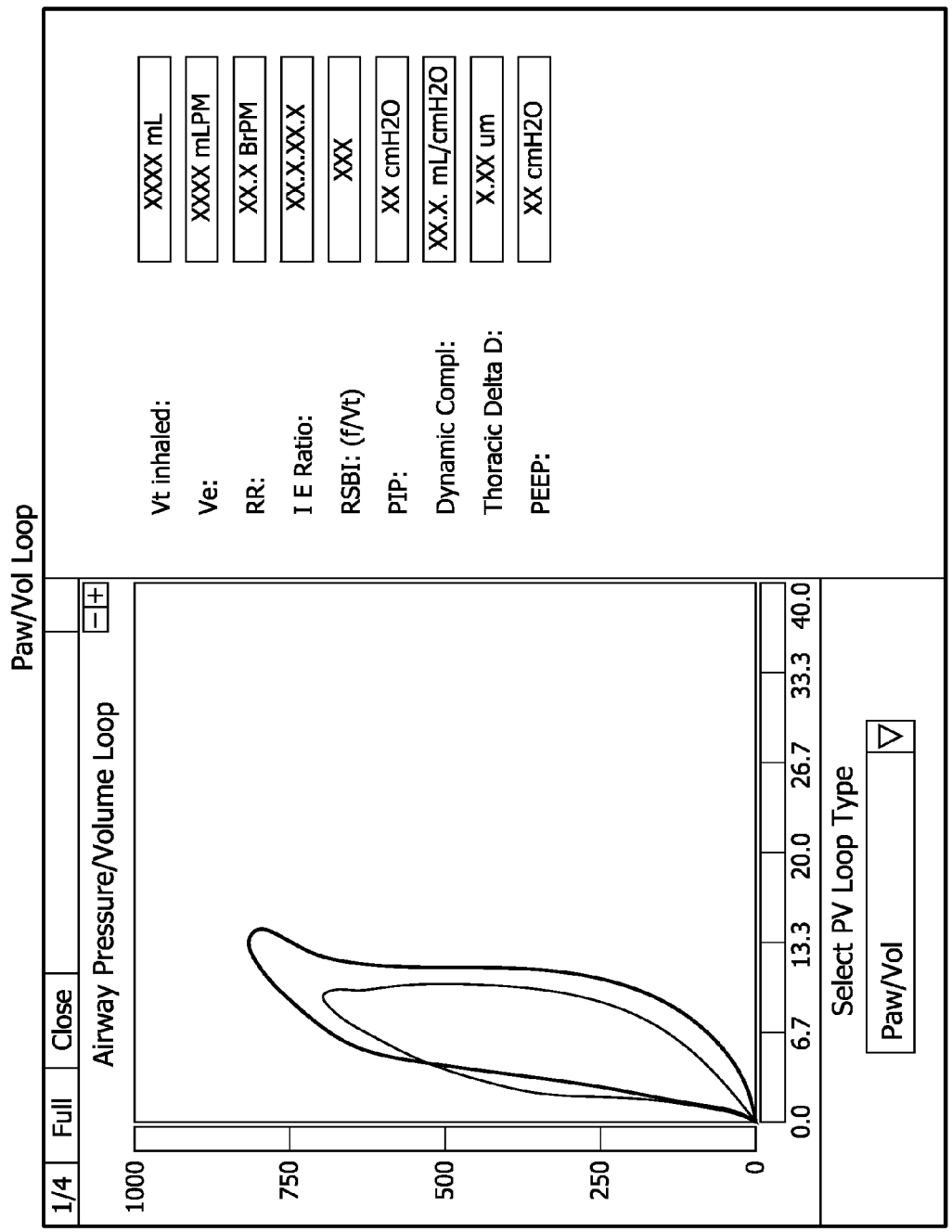
Figure 28:
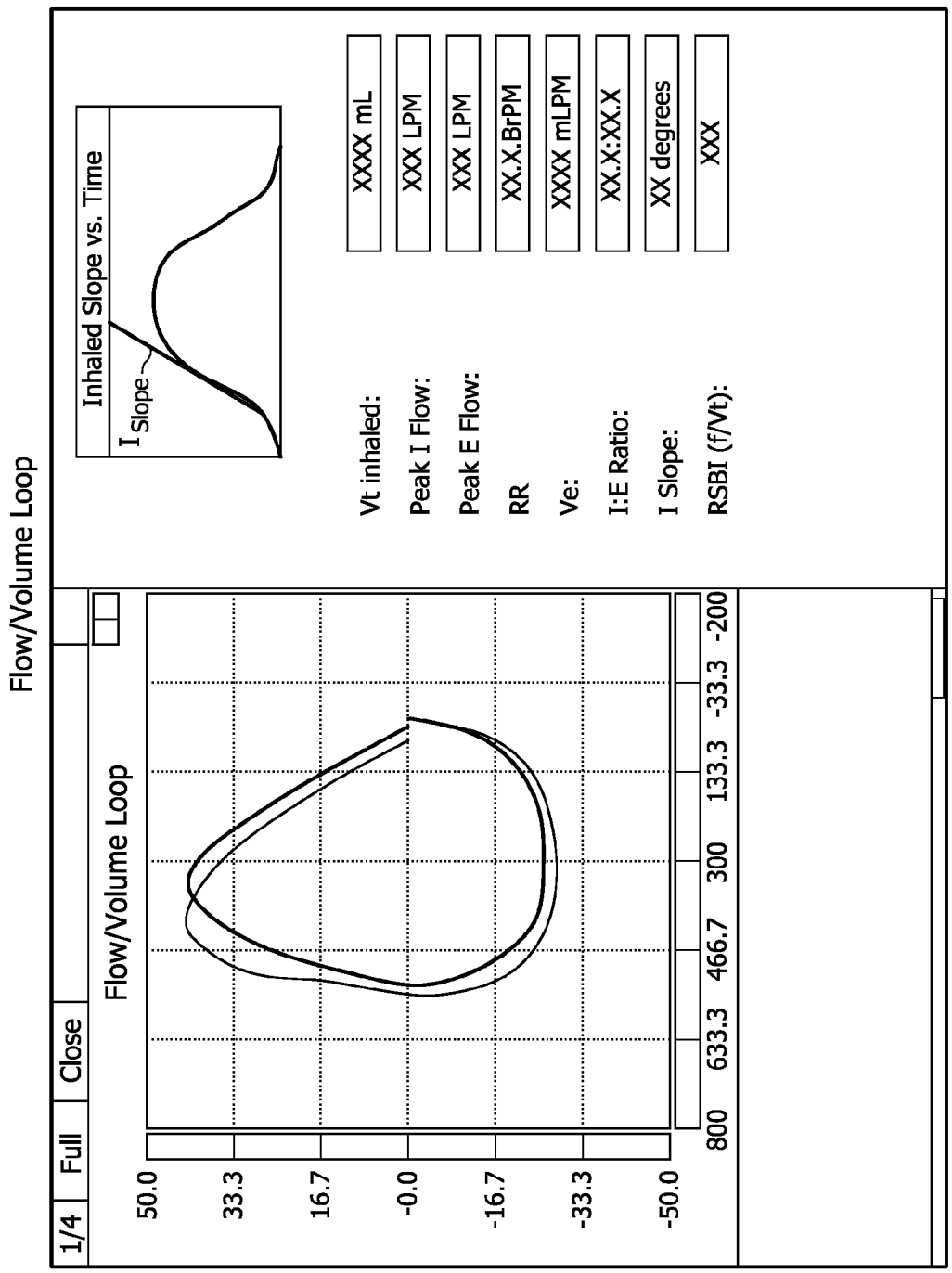

FIG. 25 illustrates a set up screen 330 that includes a patient data field 332, a monitored parameter display field 334, an oxygen concentration setting field 336, and a data display selection field 338. A note field (not shown) can also be provided. An exit selector 342 is an active field that allows the user to exit the set up screen. Patient data field 332 is also an active field that allows the user to set the characteristics of the patient, such as patient identification number, patient interface (type of interface being used by that patient, such as mask, cannula, or pneumotach), monitoring mode, age, gender, weight, height, and patient type.

Figure 17:
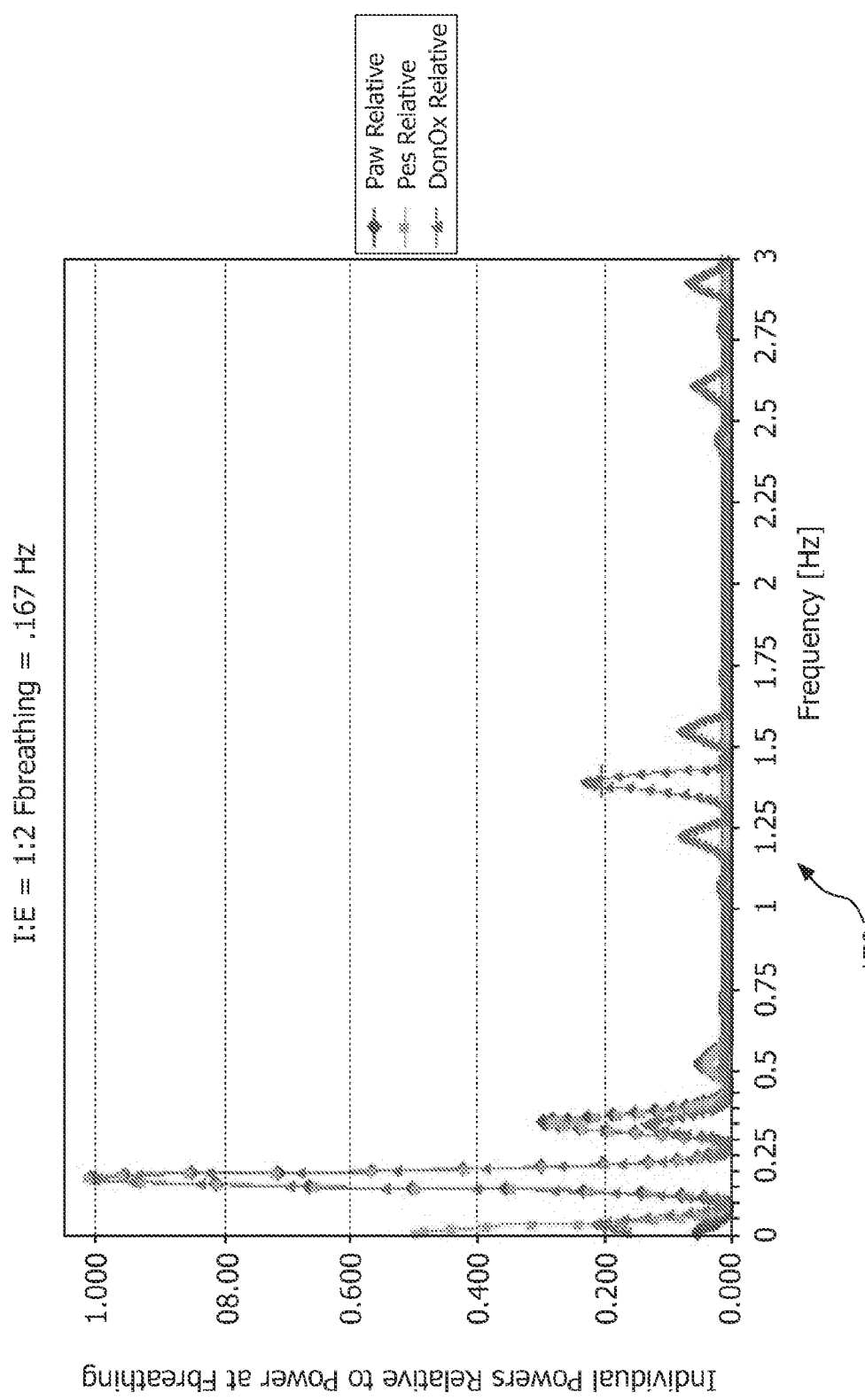
Figure 18:
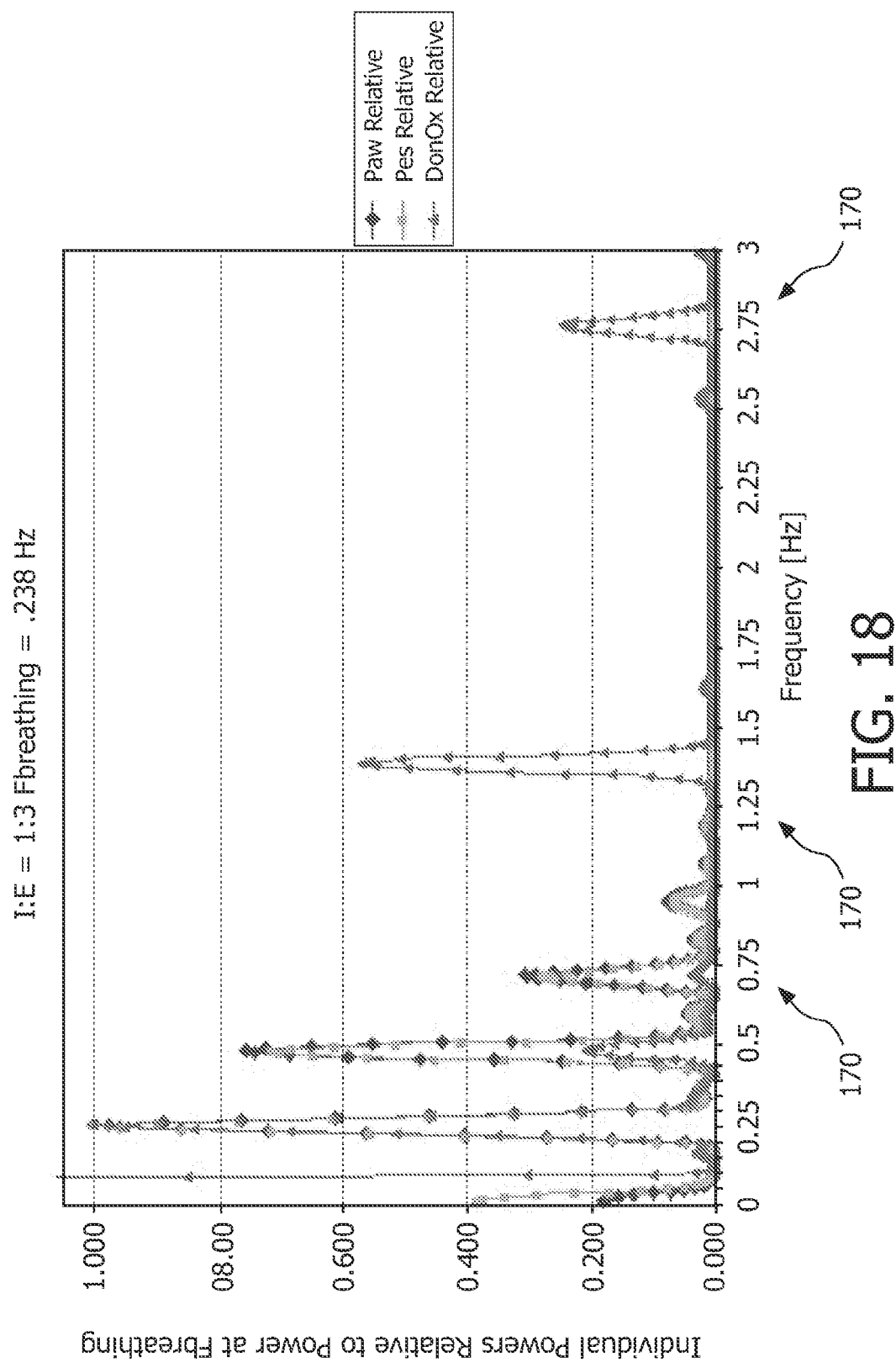

Monitored parameter display field 334 displays the parameters monitored by the extra-thoracic monitoring system. These parameters can be updated continuously or only as desired. The parameters include the following:

(1) Inspiratory Tidal Volume—volume of gas inspired by a patient during the inspiratory phase of the breathing cycle (measured via a flow sensor);

(2) Peak Inspiratory Flow—peak flow during the inspiratory phase of the breathing cycle (measured via a flow sensor);

(3) Peak Expiratory Flow—peak flow during the expiratory phase of the breathing cycle (measured via a flow sensor);

(4) Minute Ventilation—volume of gas inspired by the patient during one minute (measured via a flow sensor);

(5) Respiratory Rate—breathing rate or breathing frequency—how many breaths per minute the patient takes (measured via a flow sensor);

(6) I:E Ratio—duration of inspiration versus duration of inspiration for a breath (measured via a flow sensor);

(7) RSBI—breathing frequency versus tidal volume (calculated value);

(8) Supplemental Liter Flow—($Q_{O2}$) flow rate supplement gas, such as oxygen, being delivered to the patient in addition to the primary gas flow (measured via an oxygen flow sensor);

(9) $FIO_2$ Delivered—fractional concentration of oxygen inhaled by a patient over one breath (calculated as discussed above);

(10) Inhaled Slope—slope of rise portion of inspiratory flow (an example of this is shown in FIG. 17);

(11) Peak Inspiratory Pressure—(PIP) measured by a pressure sensor;

(12) PEEP—Positive End Expiratory Pressure (measured via a pressure sensor).

(13) Dynamic Airway Compliance—calculated from pressure and flow;

(14) $SpO_2$—Oxygen saturation (measured from pulse oximeter (IR) signal);

(15) Pulse Rate—heart rate (measured from pulse oximeter (IR) signal);

(16) Estimated Shunt—calculated as discussed above;

(17) Cardiac Delta D—$NIVD_{cardiac}$ calculated as discussed above;

(18) Thoracic Delta D—$NIVD_{Thoracic}$ calculated as discussed above; and

(19) Expiratory Tidal Volume—volume of gas expired by a patient during the expiratory phase of the breathing cycle (measured via a flow sensor);

Oxygen concentration setting field 336 is used to set the concentration of oxygen of the gas being delivered to the patient. This is accomplished according to one embodiment of the present invention by moving triangular pointers 344a and 344b to the oxygen concentration setting. The upper setting 344a is used to set the main gas oxygen concentration, and the lower gas setting 344b is used to set the supplemental gas oxygen concentration. For example, if the patient is breathing air without any supplemental oxygen, upper setting 344a is set to 0.21 and lower setting 344b is set to 0.21. If the patient is then given pure oxygen supplemental to the main flow of air, the lower setting is moved to 1.00. These settings are used, for example, in calculating $FIO_2$.

Figure 30:
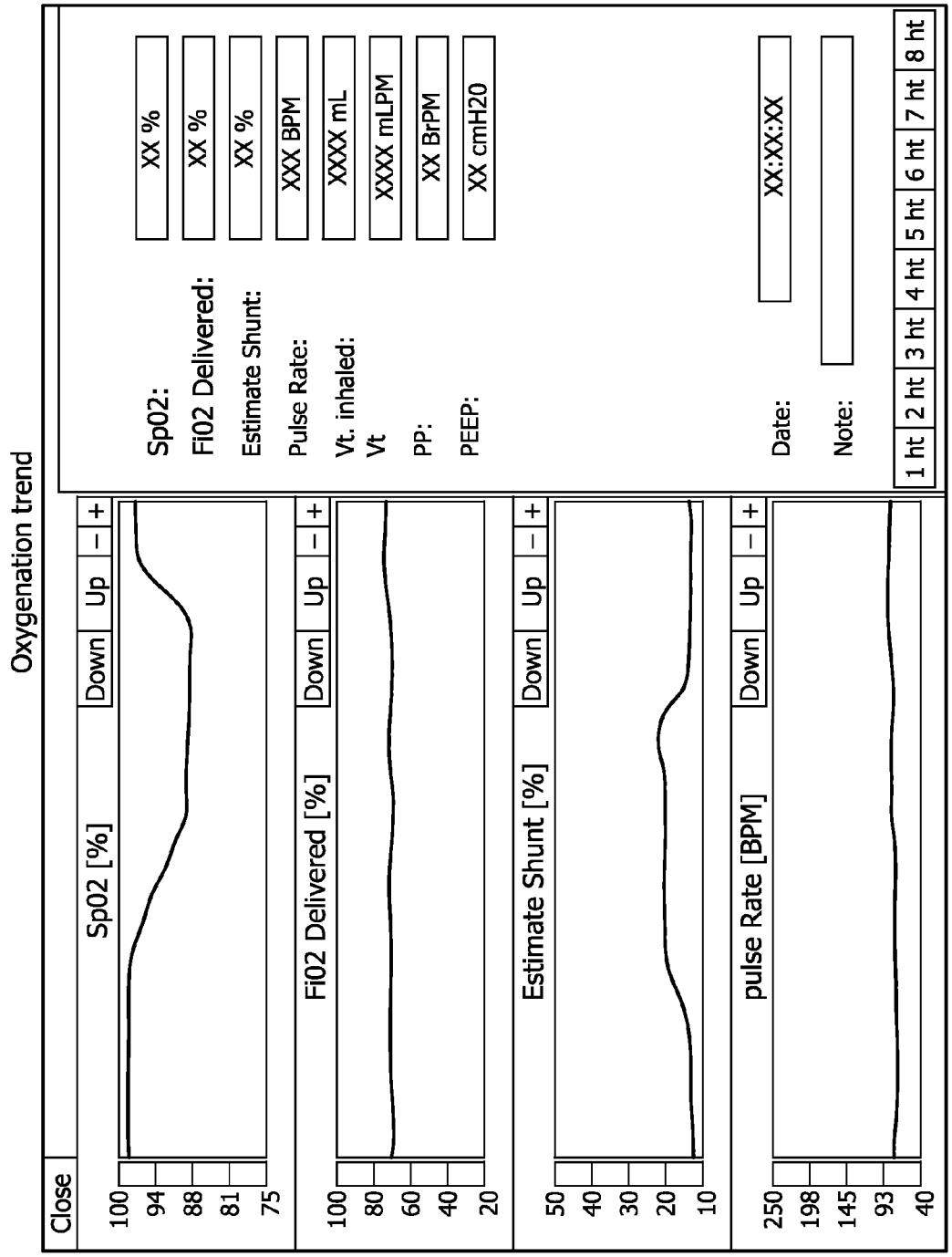
Figure 31:
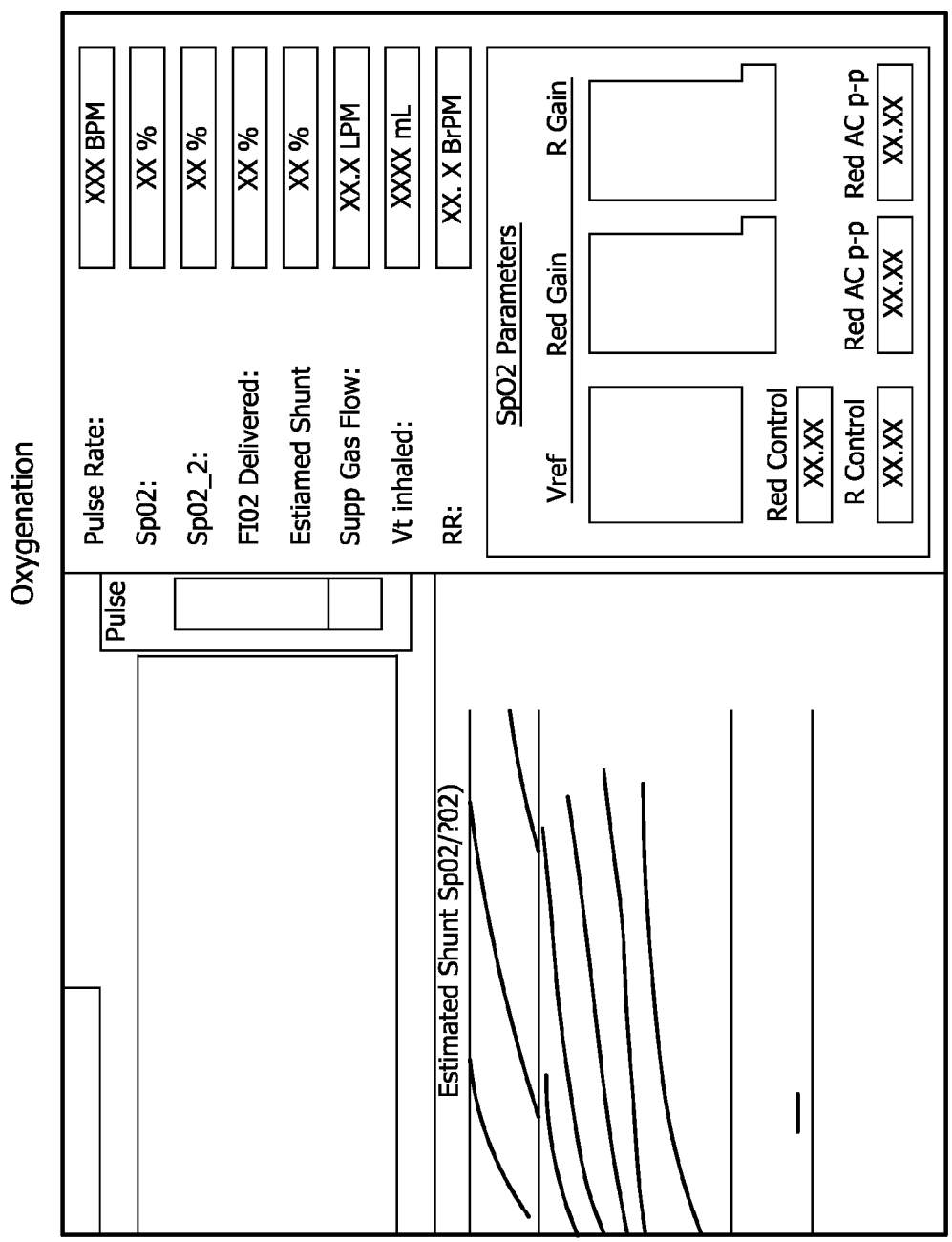
Figure 32:
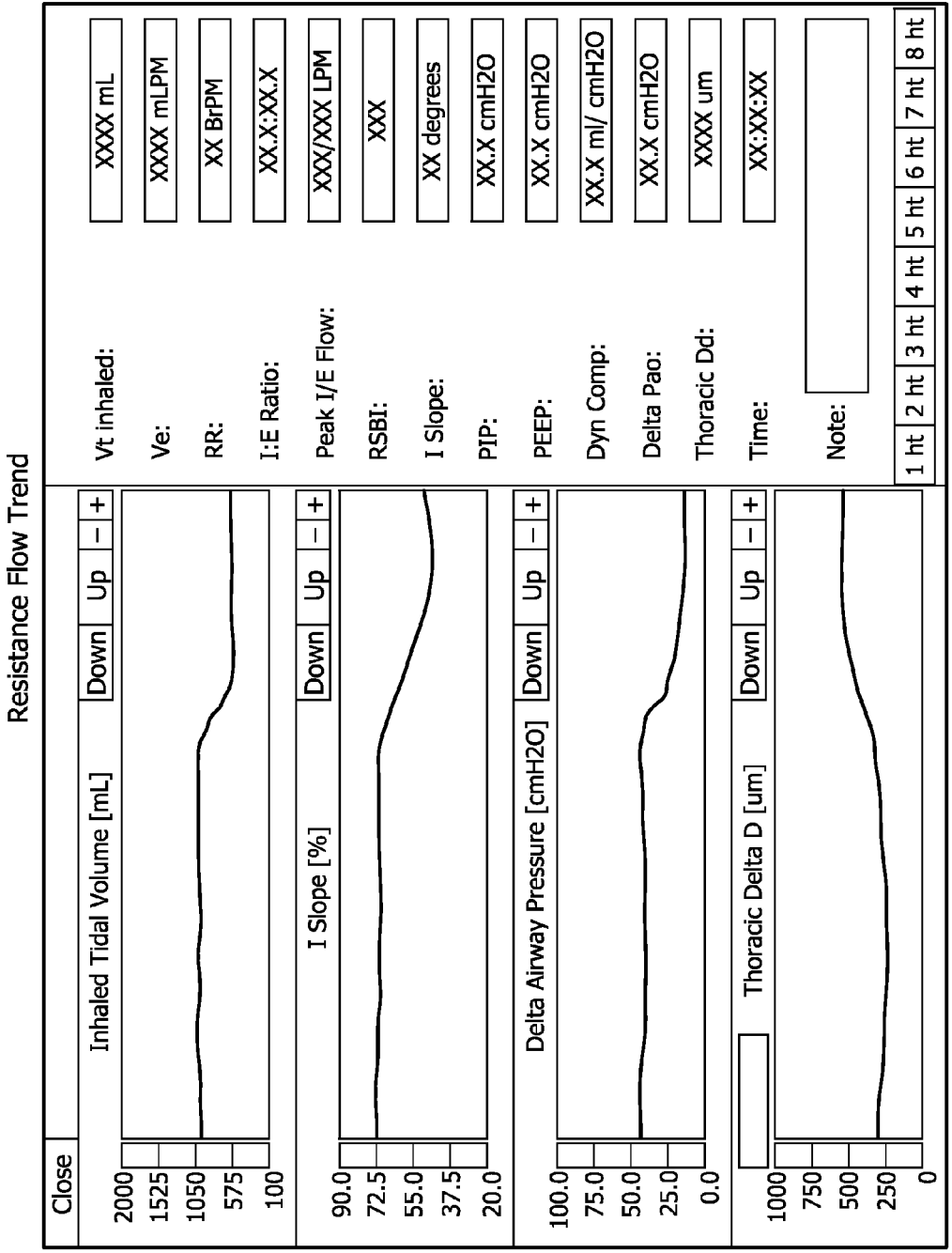
Figure 33:
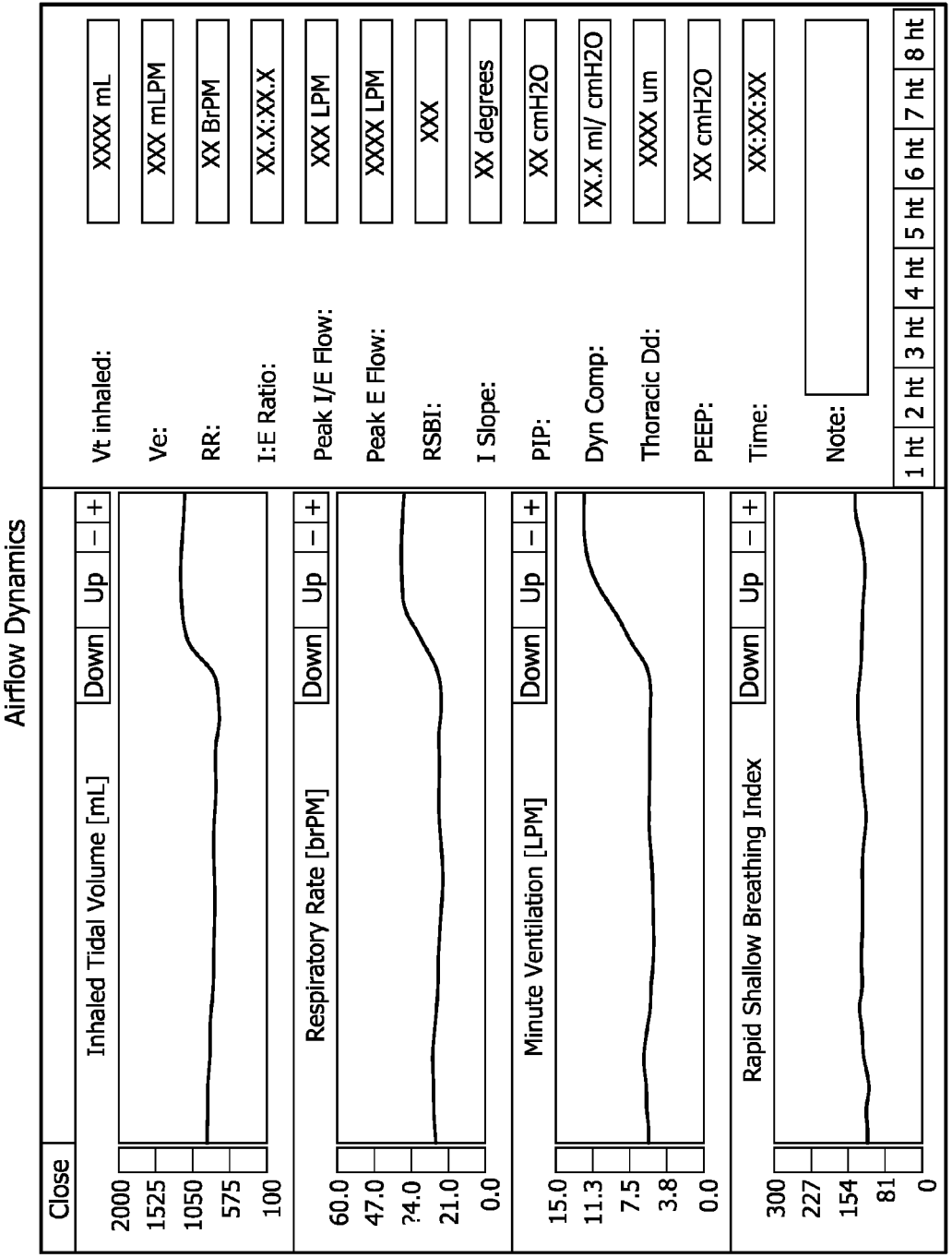

Data display selection field 338 is used to allow the user to select other screens for display. There are two types of data displays: real time displays, which show data as it's continuously monitored and calculated, and trend displays, which show monitored or calculated data over a period of time, such as over eight hours, accumulated on a breath-by-breath basis. Examples of real time displays are shown in FIGS. 26-29 and 31. Examples of trend displays are shown in FIGS. 30, 32 and 33. Displaying these other data display screens in the display area is accomplished according to one exemplary embodiment of the present invention by providing a real time data pull-down menu 346 that contains each real time data screen selection and a trended data pull-down menu 348 that contains each trended data screen selection.

As noted above, FIGS. 26-33 illustrate various screens that are used to display the information gathered and/or calculated by the monitoring system of the present invention in real time and as trended data accumulated over a period of time. It should be noted that these other screens allow the monitored variables and the calculated variables to be displayed quantitatively and graphically. The graphical presentation of this information is believed to be more easily perceived and understood by a user than a simple quantitative display. It also allows changes in the information, i.e., data trends, to be visualized clearly.

E. Wavelength Selection

One embodiment of the present invention uses the following two frequencies of light: Red having a wavelength of approximately 660 nm, and Infrared having a wavelength of approximately 940 nm. However, the present invention contemplates that a single wavelength, at the isosbestic point of approximately 805 nm, can be used in place of these two frequencies.

Figure 34:
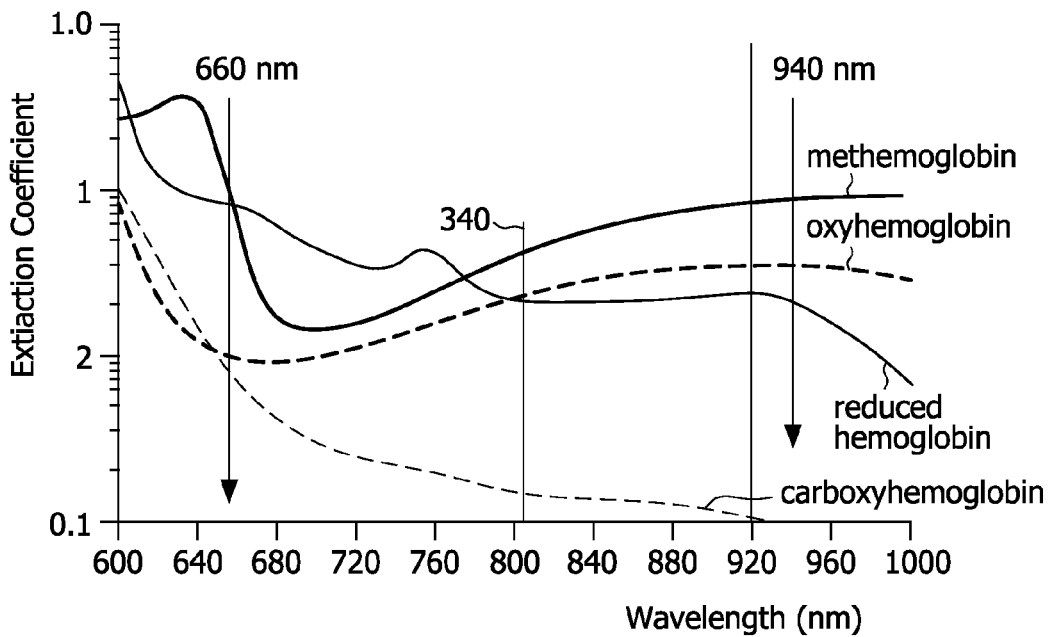
FIG. 34 is a graph illustrating the relationship between extinction coefficients and wavelengths of light

If a wavelength of light is chosen that is not affected by oxygen saturation, the calculation for Δd is simplified. As shown in FIG. 34, isosbestic point 340 occurs at a wavelength of light where the extinction coefficients for oxyhemoglobin $\epsilon_{HbO2}$ and reduced hemoglobin $\epsilon_{Hb}$ are equal. ($\epsilon_{HbO2}=\epsilon_{Hb}$). The isosbestic point is at the wavelength 805 nm. Because oxygen saturation ($SpO_2$) does not affect this wavelength, equation (1) can be simplified as follows:

$$NIVD = \Delta d = \frac{-\ln\left(\frac{I_X}{I_H}\right)}{\varepsilon_{THb}(\lambda) \cdot 2.265}, \quad (2)$$

where $\epsilon_{THb}$ is the extinction coefficient at the isosbestic point. It should be noted that $C_{TOtHb}$ represents the total hemoglobin concentration of 2.265 milli-mole per liter (mM/L), which is based on a patient with the normal amounts of dyshemoglobin.

F. Identifying Respiratory Disorders

Figure 35:
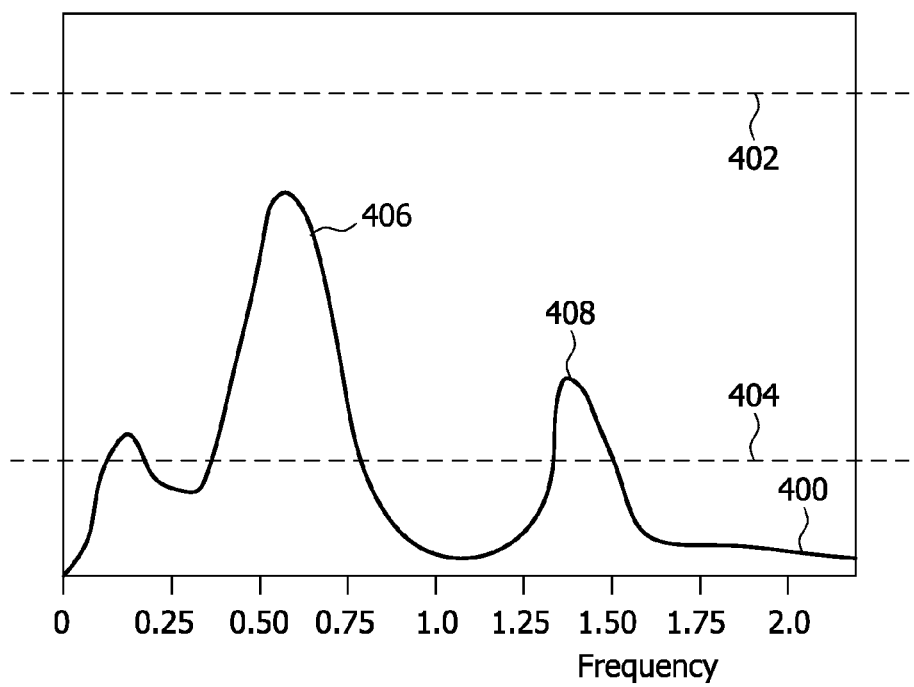
FIG. 35 is a graph illustrating a technique for identifying respiratory disorders using the extra-thoracic monitoring system of the present invention.

The FFT signal, i.e., the output of FFT transform 152 in FIG. 9, contains information that is useful in determining whether the patient suffers from a respiratory disorder, such as obstructive apneas and central apneas. FIG. 35 illustrates a frequency spectrum signal 400 that corresponds, in general, to frequency spectrum signal 158 in FIG. 12B, and which is output from zero-out component 192. FIG. 35 also illustrates a first threshold 402 and a second threshold 404 that are used to determine whether the patient suffers from a respiratory disorder.

Frequency spectrum signal 400 shown in FIG. 35 includes a first peak 406 that corresponds to the breath rate component of the frequency spectrum signal and a second peak 408 that corresponds to the heart rate component. First threshold 402 corresponds to a threshold that, if met or exceeded by first peak 406 indicates that the patient suffers from an obstructive apnea. In other words, if the amplitude of the first peak 4-6 meets or exceeds the first threshold, the patient is deemed to be suffering an obstructive apnea. An obstructive apnea is characterized by a high work of breathing, i.e., a high magnitude in first peak 406, but a minimal flow through the airway due to the obstruction of the airway. The patient is deemed to be suffering from no apneas if the amplitude of the respiratory portion 406 of FFT signal 400 is between the thresholds 402 and 404.

A central apnea is declared if the amplitude of respiratory portion 406 of FFT signal 400 meets or crosses below second threshold 404. A central apnea is characterized by little or no work of breathing, but a minimal flow through the airway due to the central apnea. In an exemplary embodiment of the present invention, first and second thresholds 402 and 404 are calculated based on the FFT of a patient's normal breathing. For example, the present invention contemplates setting the first and second thresholds based on an average of the previous peaks of the FFTs.

IX. CONCLUSION

It can be appreciated that the present invention provides a system for monitoring changes in the intra-thoracic pressure of a patient due to the patient's respiratory activity or cardiac function in real time and on a continuous basis. For example, pleural pressure changes due to respiratory effort are monitored based on changes in pressure in the extra-thoracic arterial circulatory system to allow the caregiver to estimate work of breathing. The patient's blood pressure can also be monitored continuously and non-invasively.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A pulmonary monitoring system comprising:
sensing means for detecting a physiological characteristic of a patient associated with pressure changes in such a patient's extra-thoracic arterial circulation and for outputting a first signal indicative of such pressure changes wherein the sensing means comprises a photoemitter adapted to direct light through a portion of the patient, and a photodetector adapted to receive light after having been directed through such a patient, and wherein the photoemitter emits light at a wavelength that is relatively insensitive to an oxygen saturation level of such a patient while relatively sensitive to changes in path length between the photoemitter and photodetector; and processing means for producing a pulmonary pressure signal as a measure of such a patient's intra-thoracic pressure due to respiration by isolating breath related pressure variations in the first signal.

2. The system according to claim 1, further comprising outputting means for providing the pulmonary pressure signal in a human perceivable format.

3. The system according to claim 1, further comprising photoemitter controlling means for controlling an intensity of light emitted by the photoemitter so as to compensate for non-breath related variations in the first signal.

4. The system according to claim 1, wherein the sensing means further includes at least one of an invasive blood pressure sensor adapted to be disposed within a patient's extra-thoracic arterial circulation or a non-invasive pressure sensor adapted to monitor pressure fluctuations of a patient's extra-thoracic arterial circulation.

5. A pulmonary monitoring system comprising:
sensing means for detecting a physiological characteristic of a patient associated with pressure changes in such a patient's extra-thoracic arterial circulation and for outputting a first signal indicative of such pressure changes; and processing means for producing a pulmonary pressure signal as a measure of such a patient's intra-thoracic pressure due to respiration by isolating breath related pressure variations in the first signal, and wherein the processing means comprises:

frequency analyzing means for determining frequency components of the first signal;

respiratory rate frequency component identifying means for identifying a respiratory rate frequency component ($f_{RR}$) from the frequency components of the first signal; and dynamic filtering means for filtering the first signal based on the respiratory rate frequency component $f_{RR}$ so as to isolate the respiratory rate frequency component $f_{RR}$ from the first signal to produce the pulmonary pressure signal.

6. The system according to claim 5, wherein the frequency analyzing means is a means for performing a Fourier transform that generates the frequency components of the first signal.

7. The system according to claim 5, wherein the processing means further comprises offset removing means for removing any offset in the frequency components of the first signal.

8. The system according to claim 5, further comprising respiratory rate monitoring means for determining a respiratory rate of such a patient, and wherein the respiratory rate frequency component identifying means selects the respiratory rate frequency component $f_{RR}$ from the frequency components of the first signal based on the output of the respiratory rate monitoring means.

9. The system according to claim 8, wherein the respiratory rate monitoring means is a flow sensor adapted to detect a flow of gas to or from such a patient.

10. A pulmonary monitoring system comprising:
sensing means for detecting a physiological characteristic of a patient associated with pressure changes in such a patient's extra-thoracic arterial circulation and for outputting a first signal indicative of such pressure changes; and processing means for producing a pulmonary pressure signal as a measure of such a patient's intra-thoracic pressure due to respiration by isolating breath related pressure variations in the first signal, and wherein the processing means comprises:

frequency analyzing means for determining frequency components of the first signal;

heart rate frequency component identifying means for identifying a heart rate frequency component $f_{HR}$ from the frequency components of the first signal; and dynamic filtering means for filtering the physiologic signal based on the heart rate frequency component $f_{HR}$ so as to remove the heart rate frequency component $f_{HR}$ from the physiologic signal, thereby isolating a respiratory rate frequency component $f_{RR}$ of the first signal to produce the pulmonary pressure signal.

11. The system according to claim 10, further comprising heart rate monitoring means for determining a heart rate of such a patient, and wherein the heart rate frequency component identifying means selects the heart rate frequency component $f_{HR}$ from the frequency components of the first signal based on the output of the heart monitoring means.

12. The system according to claim 11, wherein the heart rate monitoring means comprises a pulse oximeter.

13. A pulmonary monitoring system comprising:
sensing means for detecting a physiological characteristic of a patient associated with pressure changes in such a patient's extra-thoracic arterial circulation and for outputting a first signal indicative of such pressure changes; and processing means for producing a pulmonary pressure signal as a measure of such a patient's intra-thoracic pressure due to respiration by isolating breath related pressure variations in the first signal, and wherein the processing means comprises:

frequency analyzing means for determining frequency components of the first signal, including a respiratory rate frequency component $f_{RR}$ and a heart rate frequency component $f_{HR}$;

respiratory rate frequency component $f_{RR}$ identifying means for identifying the respiratory rate frequency component $f_{RR}$ from the frequency components of the first signal;

heart rate frequency component $f_{HR}$ identifying means for identifying the heart rate frequency component $f_{HR}$ from the frequency components of the first signal; and dynamic filtering means for filtering the first signal based on the respiratory rate frequency component $f_{RR}$ and the heart rate frequency component $f_{HR}$ so as to isolate the respiratory rate frequency component $f_{RR}$ from the first signal to produce the pulmonary pressure signal.

14. The system according to claim 13, wherein the dynamic filtering means (1) sets a cutoff frequency ($f_{cutoff}$) as $f_{RR}+f_{smear}$ responsive to the respiratory rate frequency component $f_{RR}$ being less than the heart rate frequency component $f_{HR}$, (2) sets the cutoff frequency ($f_{cutoff}$) as $f_{RR}-f_{smear}$ responsive to the respiratory rate frequency component $f_{RR}$ being greater than the heart rate frequency component $f_{HR}$, where $f_{smear}$ is a predetermined threshold frequency, and (3) low pass filters the first signal at the cutoff frequency $f_{cutoff}$.

15. The system according to claim 14, further comprising:
respiratory rate monitoring means for determining a respiratory rate of such a patient, and wherein the respiratory rate frequency component identifying means selects the respiratory rate frequency component $f_{RR}$ from the frequency components of the first signal based on the output of the respiratory rate monitoring means; and heart rate monitoring means for determining a heart rate of such a patient, and wherein the heart rate frequency component identifying means selects the heart rate frequency component $f_{HR}$ from the frequency components of the first signal based on the output of the heart monitoring means.

16. The system according to claim 1, further comprising a first flow sensor adapted to quantitatively measure a flow of gas inhaled by a patient, exhaled by a patient, or both inhaled and exhaled by a patient.

17. The system according to claim 16, wherein the processing means also determines at least one of the following physiological characteristics of a patient based on the output of the first flow sensor:
 (a) inspiratory tidal volume;
 (b) expiratory tidal volume;
 (c) inspiratory peak flow;
 (d) expiratory peak flow;
 (e) minute ventilation;
 (e) respiratory rate;
 (f) inspiratory/expiratory ratio;
 (g) rapid shallow breathing index; and
 (h) slope of a flow waveform during inhalation.

18. The system according to claim 16, further comprising means for delivering a supplemental flow of a supplemental gas to such a patient.

19. The system according to claim 18, further comprising a second flow sensor adapted to quantitatively measure a flow of the supplemental gas delivered to such a patient.

20. The system according to claim 19, wherein the processing means also determines the fractional concentration of supplemental gas inhaled by such a patient based on the output of the first flow sensor and the second flow sensor.

21. The system according to claim 20, wherein the sensing means forms a pulse oximeter adapted to measure a pulse oximetry arterial oxygen saturation $SpO_2$ of such a patient, wherein the supplemental gas is oxygen so that the processor determines a fractional concentration of oxygen inhaled by such a patient ($FIO_2$) based on the output of the first flow sensor and the second flow sensor, and wherein the processor determines an estimated shunt of such a patient based on the measured $SpO_2$ and $FIO_2$.

22. The system according to claim 21, further comprising a display, and wherein the processing means is programmed to cause a nomogram to be presented on the display illustrating a relationship between the measured $SpO_2$, the calculated $FIO_2$, and the estimated shunt.

23. The system according to claim 16, further comprising a pressure sensor adapted to measure a pressure at an airway of such a patient, wherein the processing means also determines at least one of the following based on an output of the pressure sensor or the output of the pressure sensor and the first flow sensor:
 (a) peak inspiratory pressure;
 (b) positive end expiratory pressure; and
 (c) dynamic airway compliance.

24. The system according to claim 1, wherein the sensing means forms a pulse oximeter adapted to measure a pulse oximetry arterial oxygen saturation $SpO_2$ of such a patient, wherein the processing means also determines a pulse rate of such a patient based on the output of the pulse oximeter.

25. A pulmonary monitoring method comprising:
 (a) providing a pulmonary monitoring system including a light emitter and light receiver;
 (b) using the pulmonary monitoring system to (a) detect a physiological characteristic of a patient associated with pressure changes in such a patient's extra-thoracic arterial circulation and (b) output a first signal indicative of such pressure changes, wherein detecting a physiological characteristic of a patient comprises:
  (1) passing light through a portion of the patient using the light emitter, and
  (2) receiving light using the light receiver after having been transmitted through such a patient, wherein the light has a wavelength that is relatively insensitive to an oxygen saturation level of such a patient while relatively sensitive to changes in path length between a photoemitter and photoreceiver;
 (c) producing, using a controller, a pulmonary pressure signal as a measure of such a patient's intra-thoracic pressure due to respiration by isolating breath related pressure variations in the first signal; and
 (d) outputting the pulmonary pressure signal in a human perceivable format.

26. The method according to claim 25, further comprising controlling an intensity of light emitted by the photoemitter so as to compensate for non-breath related variations in the first signal.

27. A pulmonary monitoring method comprising:
 detecting a physiological characteristic of a patient associated with pressure changes in such a patient's extra-thoracic arterial circulation and for outputting a first signal indicative of such pressure changes, and wherein detecting a physiological characteristic of a patient includes providing an invasive blood pressure sensor within a patient's extra-thoracic arterial circulation; and
 producing, using a controller, a pulmonary pressure signal as a measure of such a patient's intra- thoracic pressure due to respiration by isolating breath related pressure variations in the first signal.

28. The method according to claim 25, wherein detecting a physiological characteristic of a patient includes providing a non-invasive pressure sensor adapted to monitor pressure fluctuations of a patient's extra-thoracic arterial circulation.

29. A pulmonary monitoring method comprising:
 providing a pulmonary monitoring system including (a) a sensing system adapted to detect a physiological characteristic of a patient associated with pressure changes in such a patient's extra-thoracic arterial circulation, and (b) a controller;
 detecting such a physiological characteristic using the sensing system and outputting a first signal indicative of such pressure changes to the controller; and
 using the controller to produce a pulmonary pressure signal as a measure of such a patient's intra-thoracic pressure due to respiration by isolating breath related pressure variations in the first signal, and wherein producing the pulmonary pressure signal comprises:
  determining frequency components of the first signal;
  identifying a respiratory rate frequency component ($f_{RR}$) from the frequency components of the first signal; and
  filtering the first signal based on the respiratory rate frequency component $f_{RR}$ so as to isolate the respiratory rate frequency component $f_{RR}$ from the first signal to produce the pulmonary pressure signal.

30. The method according to claim 29, wherein determining frequency components of the first signal includes analyzing the first signal with a Fourier transform that generates the frequency components of the first signal.

31. The method according to claim 29, wherein producing a pulmonary pressure signal further comprises removing any offset in the frequency components of the first signal.

32. The method according to claim 29, further comprising determining a respiratory rate of such a patient via a respiratory rate monitor, and wherein identifying the respiratory rate frequency component $f_{RR}$ from the frequency components of the first signal is accomplished based on the output of the respiratory rate monitor.

33. The method according to claim 32, wherein the respiratory rate monitor is a flow sensor adapted to detect a flow of gas to or from such a patient.

34. A pulmonary monitoring method comprising:
providing a pulmonary monitoring system including (a) a sensing system adapted to detect a physiological characteristic of a patient associated with pressure changes in such a patient's extra-thoracic arterial circulation, and (b) a controller;
detecting such a physiological characteristic using the sensing system and outputting a first signal indicative of such pressure changes to the controller; and
using the controller to produce a pulmonary pressure signal as a measure of such a patient's intra-thoracic pressure due to respiration by isolating breath related pressure variations in the first signal, and wherein producing the pulmonary pressure signal comprises:
determining frequency components of the first signal;
identifying a heart rate frequency component $f_{HR}$ from the frequency components of the first signal; and
filtering the physiologic signal based on the heart rate frequency component $f_{HR}$ so as to remove the heart rate frequency component $f_{HR}$ from the physiologic signal, thereby isolating a respiratory rate frequency component $f_{RR}$ of the first signal to produce the pulmonary pressure signal.

35. The method according to claim 34, further comprising determining a heart rate of such a patient via a heart rate monitor, and wherein identifying the heart rate frequency component $f_{HR}$ from the frequency components of the first signal is accomplished based on the output of the heart rate monitor.

36. The method according to claim 35, wherein determining a heart rate of such a patient is accomplished using a pulse oximeter.

37. A pulmonary monitoring method comprising:
providing a pulmonary monitoring system including (a) a sensing system adapted to detect a physiological characteristic of a patient associated with pressure chances in such a patient's extra-thoracic arterial circulation, and (b) a controller:
detecting such a physiological characteristic using the sensing system and outputting a first signal indicative of such pressure changes to the controller; and
using the controller to produce a pulmonary pressure signal as a measure of such a patient's intra-thoracic pressure due to respiration by isolating breath related pressure variations in the first signal, and wherein producing a pulmonary pressure signal comprises:
determining frequency components of the first signal, including a respiratory rate frequency component $f_{RR}$ and a heart rate frequency component $f_{HR}$;
identifying a respiratory rate frequency component $f_{RR}$ from the frequency components of the first signal;
identifying a heart rate frequency component $f_{HR}$ from the frequency components of the first signal; and
filtering the first signal based on the respiratory rate frequency component $f_{RR}$ and the heart rate frequency component $f_{HR}$ so as to isolate the respiratory rate frequency component $f_{RR}$ from the first signal to produce the pulmonary pressure signal.

38. The method according to claim 37, wherein filtering the first signal includes:
(1) setting a cutoff frequency ($f_{cutoff}$) as $f_{RR}+f_{smear}$ responsive to the respiratory rate frequency component $f_{RR}$ being less than the heart rate frequency component $f_{HR}$,
(2) setting the cutoff frequency ($f_{cutoff}$) as $f_{RR}-f_{smear}$ responsive to the respiratory rate frequency component $f_{RR}$ being greater than the heart rate frequency component $f_{HR}$, where $f_{smear}$ is a predetermined threshold frequency, and
(3) low pass filtering the first signal at the cutoff frequency $f_{cutoff}$.

39. The method according to claim 37, further comprising:
determining a respiratory rate of such a patient via a respiratory rate monitor, and wherein identifying the respiratory rate frequency component $f_{RR}$ from the frequency components of the first signal is accomplished based on the output of the respiratory rate monitor; and
determining a heart rate of such a patient via a heart rate monitor, and wherein identifying the heart rate frequency component $f_{HR}$ from the frequency components of the first signal is accomplished based on the output of the heart rate monitor.

40. The method according to claim 25, further comprising quantitatively measuring a flow of gas inhaled by a patient, exhaled by a patient, or both inhaled and exhaled by a patient.

41. The method according to claim 40, further comprising determining at least one of the following physiological characteristics of a patient based on the measured flow:
(a) inspiratory tidal volume;
(b) expiratory tidal volume;
(c) inspiratory peak flow;
(d) expiratory peak flow;
(e) minute ventilation;
(e) respiratory rate;
(f) inspiratory/expiratory ratio;
(g) rapid shallow breathing index; and
(h) slope of a flow waveform during inhalation.

42. The method according to claim 40, further comprising delivering a supplemental flow of a supplemental gas to such a patient.

43. The method according to claim 42, further comprising quantitatively measuring a flow of the supplemental gas delivered to such a patient.

44. The method according to claim 43, further comprising determining a fractional concentration of supplemental gas inhaled by such a patient based on the output of the first flow sensor and the second flow sensor.

45. The method according to claim 43, further comprising measuring a pulse oximetry arterial oxygen saturation $SpO_2$ of such a patient, determining a fractional concentration of oxygen inhaled by such a patient ($FIO_2$) based on the output of the first flow sensor and the second flow sensor, and determining an estimated shunt of such a patient based on the measured $SpO_2$ and $FIO_2$.

46. The method according to claim 45, further comprising displaying a nomogram illustrating a relationship between the measured $SpO_2$, the calculated $FIO_2$, and the estimated shunt.

47. The method according to claim 40, further comprising measuring a pressure of gas at an airway of such a patient, and determining at least one of the following based on an output of the pressure sensor or the output of the pressure sensor and the first flow sensor:
- (a) peak inspiratory pressure;
- (b) positive end expiratory pressure; and
- (c) dynamic airway compliance.

48. The method according to claim 25, further comprising a pulse oximeter adapted to measure a pulse oximetry arterial oxygen saturation $SpO_2$ of such a patient, wherein the processing means also determines a pulse rate of such a patient based on the output of the pulse oximeter.

* * * * *